US008772281B2

(12) United States Patent
Fukuchi et al.

(10) Patent No.: US 8,772,281 B2
(45) Date of Patent: *Jul. 8, 2014

(54) REMEDY FOR DIABETES

(71) Applicant: Ajinomoto Co., Inc., Tokyo (JP)

(72) Inventors: Naoyuki Fukuchi, Kawasaki (JP);
Satoru Okamoto, Kawasaki (JP);
Wataru Miyanaga, Kawasaki (JP); Sen Takeshita, Kawasaki (JP); Masaru Takayanagi, Kawasaki (JP); Yumiko Fukuda, Kawasaki (JP); Takao Ikenoue, Kawasaki (JP); Naoyuki Yamada, Kawasaki (JP); Naoko Arashida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/709,798

(22) Filed: Dec. 10, 2012

(65) Prior Publication Data

US 2013/0130277 A1 May 23, 2013

Related U.S. Application Data

(60) Division of application No. 12/574,947, filed on Oct. 7, 2009, now Pat. No. 8,357,680, which is a continuation of application No. PCT/JP2008/057185, filed on Apr. 11, 2008.

(30) Foreign Application Priority Data

Apr. 11, 2007  (JP) ................................. 2007-104085

(51) Int. Cl.
*A01N 43/62* (2006.01)
*A61K 31/55* (2006.01)

(52) U.S. Cl.
USPC ......................................... 514/220; 540/557

(58) Field of Classification Search
USPC .......................................... 514/220; 540/557
See application file for complete search history.

(56) References Cited

U.S. PATENT DOCUMENTS

| | | | | |
|---|---|---|---|---|
| 7,153,850 | B2 * | 12/2006 | Iino et al. ...................... | 514/220 |
| 7,326,701 | B2 * | 2/2008 | Iino et al. ...................... | 514/220 |
| 7,632,830 | B2 * | 12/2009 | Iino et al. ...................... | 514/220 |
| 7,807,663 | B2 * | 10/2010 | Ikenoue et al. ............ | 514/211.11 |
| 7,834,006 | B2 * | 11/2010 | Hirama et al. ............... | 514/221 |
| 7,928,101 | B2 * | 4/2011 | Hirama et al. ............... | 514/220 |
| 7,951,799 | B2 * | 5/2011 | Tanaka et al. ................ | 514/220 |
| 2004/0048847 | A1 * | 3/2004 | Iino et al. .................. | 514/211.11 |
| 2005/0272641 | A1 * | 12/2005 | Ikenoue et al. .................... | 514/3 |
| 2006/0189597 | A1 * | 8/2006 | Ilno et al. ...................... | 514/215 |
| 2006/0194789 | A1 * | 8/2006 | Hirama et al. ................ | 514/215 |
| 2006/0258637 | A1 * | 11/2006 | Hirama et al. ............. | 514/211.1 |
| 2008/0096862 | A1 * | 4/2008 | Iino et al. .................... | 514/211.1 |
| 2008/0108604 | A1 * | 5/2008 | Tanaka et al. ................ | 514/220 |
| 2009/0041754 | A1 | 2/2009 | Endoh et al. | |
| 2010/0035892 | A1 * | 2/2010 | Kozmin et al. ........... | 514/253.04 |
| 2011/0034433 | A1 * | 2/2011 | Von Nussbaum et al. ........................ | 514/210.18 |
| 2011/0160191 | A1 * | 6/2011 | Hirama et al. ................ | 514/220 |

FOREIGN PATENT DOCUMENTS

| | | |
|---|---|---|
| WO | WO 01/53266 | 7/2001 |
| WO | WO 02/44180 | 6/2002 |
| WO | WO 2004/0469259 | 8/2004 |
| WO | WO 2005/042536 | 5/2005 |
| WO | WO 2005/068467 | 7/2005 |
| WO | WO 2006/118341 | 11/2006 |
| WO | WO 2007/020853 | 2/2007 |
| WO | WO 2008126920 A1 * | 10/2008 |

OTHER PUBLICATIONS

M. Sheehan, et al., "Current Therapeutic Options in Type 2 Diabetes Mellitus: A Practical Approach", Clinical Medicine & Research, vol. 1, No. 3, 2003, pp. 189-200.
E. Hajduch, et al., "Protein Kinase B (PKB/Akt)—A Key Regulator of Glucose Transport?", FEBS Letters, vol. 492, 2001, pp. 199-203.
N. Wettschureck, et al., "Mammalian G Proteins and Their Cell Type Specific Functions", Physical Rev., vol. 85, 2005, pp. 1159-1204.
U. Maier, et al., "Roles of Non-Catalytic Subunits in Gβγ-inducted Activation of Class I Phosphoinositide 3-Kinase Isoforms βand γ", The Journal of Biological Chemistry, vol. 274, No. 41, Oct. 8, 1999, pp. 29311-29317.
J. Scott, et al., "Evidence That a Protein-Protein Interaction "Hot Spot" On Heterotrimeric G Protein βy subunits Is Used for Recognition of a Subclass of Effectors", The EMBO Journal, vol. 20, No. 4, 2001, pp. 767-776.
T.Bonacci, et al., "Differential Targeting of Gβγ-Subunit Signaling with Small Molecules", SCIENCE, vol. 312, 2006, pp. 443-446.
T. Asano, et al., "p110β is Up-Regulated during Differentiation of 3T3-L1 Cells and Contributes to the Highly Insulin-Responsive Glucose Transport Activity*", The Journal of Biological Chemistry, vol. 275, No. 23, Jun. 9, 2000, pp. 17671-17676.
P. Sternweis, et al., "Isolation of Two Proteins with High Affinity for Guanine Nucleotides From Membranes of Bovine Brain*", The Journal of Biological Chemistry, vol. 259, No. 22, Nov. 25, 1984, pp. 13806-13813.
T. Kozasa, et al., "Purification of Recombinant G Proteins From Sf9 Cells by Hexahistidine Tagging of Associated Subunits", The Journal of Biological Chemistry, vol. 270, No. 4, Jan. 27, 1995, pp. 1734-1741.
K. Kerchner, et al., "Differential Sensitivity of Phosphatidylinositol 3-Kinase p110γ to Isoforms of G Protein βγ Dimers*", The Journal of Biological Chemistry, vol. 279, No. 43, Oct. 22, 2004, pp. 44554-44562.

(Continued)

*Primary Examiner* — Deepak Rao
*Assistant Examiner* — Alexander R Pagano
(74) *Attorney, Agent, or Firm* — Oblon, Spivak, McClelland, Maier & Neustadt, L.L.P.

(57) ABSTRACT

A method of screening a compound having a hypoglycemic effect (hereinafter referred to as "hypoglycemic compound"), a remedy for diabetes which contains a compound having a novel function mechanism, etc. More specifically speaking, a method of screening a hypoglycemic compound capable of binding to the β subunit of a trimeric GTP-binding protein, a remedy for diabetes comprising a hypoglycemic compound, which is characterized by being capable of binding to the β subunit of a trimeric GTP-binding protein, as the active ingredient, etc.

10 Claims, 16 Drawing Sheets

(56) References Cited

OTHER PUBLICATIONS

D. Leopold, et al., "Gβγ Stimulates Phosphoinositide 3-Kinase-γ by Direct Interaction with Two Domains of the Catalytic p110 Subunit*", The Journal of Biological Chemistry, vol. 273, No. 12, Mar. 20, 1998, pp. 7024-7029.

S. Dowler, et al., "Protein Lipid Overlay Assay", Science's STKE, L6, 2002, pp. 1-10.

W. Cho, et al., "Membrane-Protein Interactions in Cell Signaling and Membrane Trafficking", Annual Reviews of Biophysical Biomolecular Structure, vol. 34, 2005, pp. 119-1951.

I. Simpson, et al., "Hormonal Regulation of Mammalian Glucose Transport[1]", Annual Reviews of Biochemistry, vol. 55, 1986, pp. 1059-1089.

T. Davis, et al., "Structural and Molecular characterization of a Preferred Protein Interaction Surface of G Protein βγ Subunits", Biochemistry, vol. 44, 2005, pp. 10593-10604.

J. Zhang, et al., "A Simple Statistical Parameter for Use in Evaluation and Validation of High Throughput Screening Assays", Journal of Biomolecular Screening, vol. 4, No. 2, 1999, pp. 67-73.

Y. Kanoh, et al., "Effect of Pertussis Toxin Insulin-Induced Signal Transduction in Rat Adipocytes and Soleus Muscles", Cellular Signalling, vol. 12, No. 4, 2000, pp. 223-232.

O. Hazeki, et al., "Activation of PI 3-Kinase by G Protein βγ Subunits", Life Science, vol. 62, No. 17/18, 1998, pp. 1555-1559.

H. Kubo, et al., "Specific Role of p85/p110β in GTP-Binding Protein-Mediated Activation of Akt-1", DAI 78 KAI The Japanese Biochemical Society Taikai Happyo Shorokushu, Aug. 25, 2005, p. 931, Abstract No. 3P-368.

H. Chen, et al., "Insulin signaling in Vascular Endothelial Cells: A Key Role for Heterotrimeric G Proteins Revealed by siRNA-Mediated Gβ1 Krockdown", Biochemistry, vol. 45, 2006, pp. 8023-8033.

European Office Action dated Aug. 2, 2012 in corresponding European Patent Application No. 08 740 282 (4 pp.).

Kowluru A et al: "A novel regulatory mechanism for trimeric GTP-binding proteins in the membrane and secretory granule fractions of human and rodent beta cells". Biochemical Journal. vol. 313, Jan. 1, 1996. pp. 97-108. XP002269285.

International Search Report issued in PCT/JP2008/057185 on May 27, 2008.

* cited by examiner

Fig. 10
a) Gβ1γ2-Myc
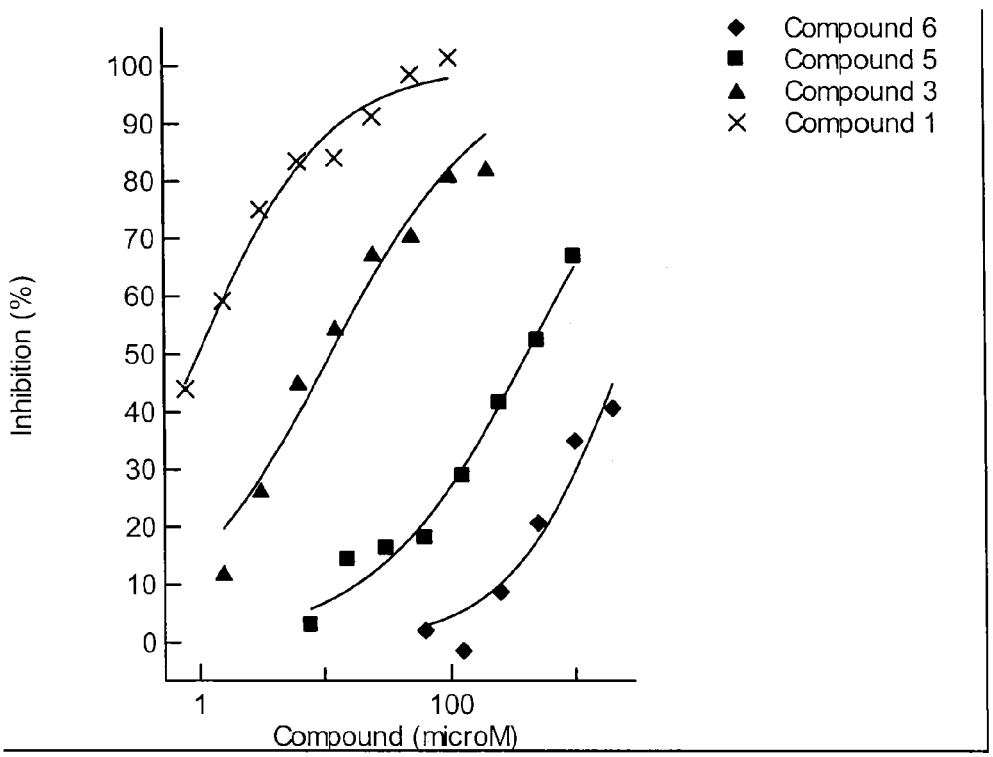
b) Gβ4γ2-Myc
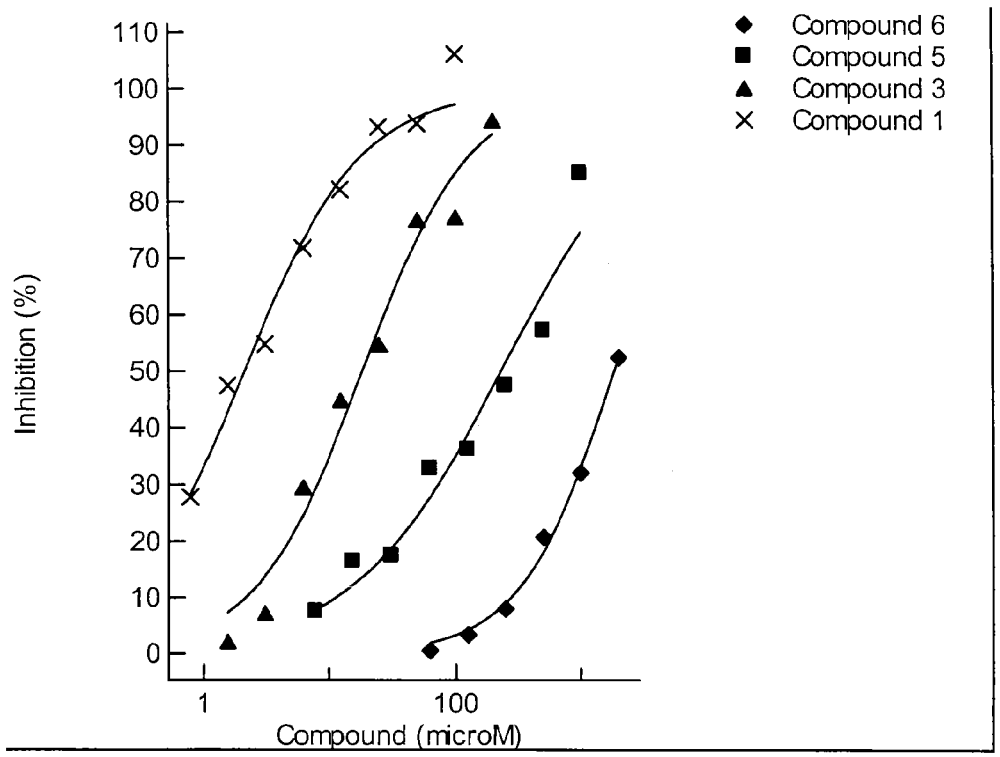

Fig. 14
a) Activity in absence of Gβ
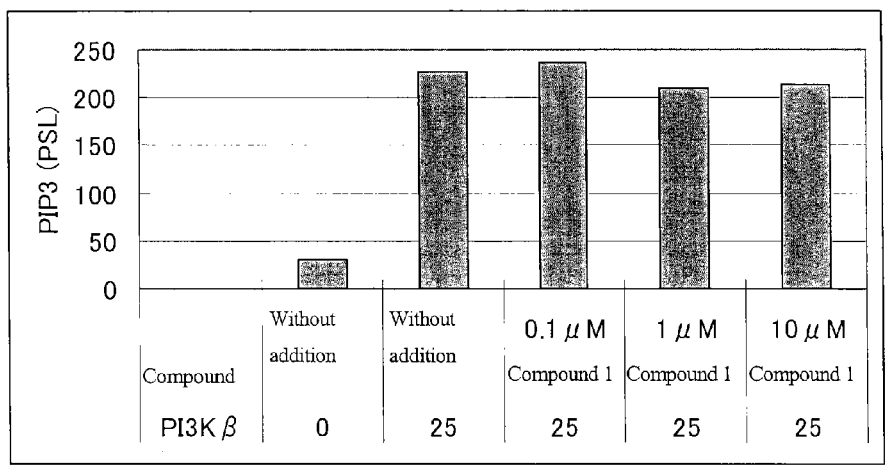
b) Activity in presence of Gβ
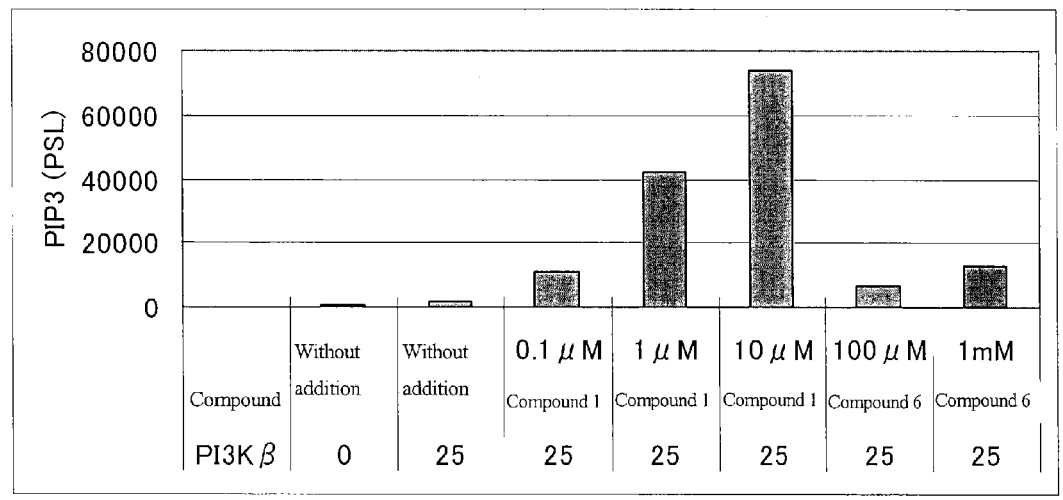

REMEDY FOR DIABETES

CROSS REFERENCES TO RELATED APPLICATIONS

This application is a Divisional Application of U.S. patent application Ser. No. 12/574,947, filed on Oct. 7, 2009, which was a continuation of International patent Application No. PCT/JP2008/057185, filed on Apr. 11, 2008, and claims priority to Japanese Patent Application No. 2007-1104085, filed on Apr. 11, 2007.

FIELD OF THE INVENTION

The present invention relates to a method for screening a compound having a hypoglycemic effect (hereinafter referred to as the hypoglycemic compound), an antidiabetic agent containing a compound having a novel mechanism of action, etc. The invention relates more specifically to a method for screening a hypoglycemically effective substance capable of binding to a trimeric GTP-binding protein β subunit, an antidiabetic agent containing as an active ingredient a hypoglycemic compound capable of binding to the trimeric GTP-binding protein β subunit, etc.

BACKGROUND OF THE INVENTION

Diabetes is such a clinical condition that blood glucose level is increased due to increase of insulin resistance in a peripheral tissue or reduction of insulin secretion. The disease leads to various serious complications, and thus the diabetes has to be treated with a medicament. Conventionally, sulfonylurea agents, phenylalanine derivatives, α-glucosidase inhibitors, biguanides, thiazolidine derivatives, insulin, etc. have been used as antidiabetic agents (Non-Patent Document 1: Sheehan et al., *Clinical Medicine & Research*, 1, 189, (2003)).

In recent years, compounds capable of enhancing the glucose uptake activity of a peripheral cell such as a adipocyte (hereinafter referred to as the glucose uptake enhancers) have been known (Patent Document 1: WO 02/44180; Patent Document 2: WO 2005/068467; Patent Document 3: WO 2005/042536; Patent Document 4: WO 2006/118341). These compounds are indicated to enhance the glucose uptake activity of a adipocyte, etc. even in the absence of insulin, and further to exhibit a hypoglycemic effect in a diabetic model animal. The above medicaments other than insulin, conventionally used as the antidiabetic agent, cannot enhance the glucose uptake activity of a adipocyte, etc. in the absence of insulin. Thus, the glucose uptake enhancers described in Patent Documents 1 to 4 are considered to be useful as the antidiabetic agent. However, the mechanisms of action of these glucose uptake enhancers have not been known and reported.

It has been known that a protein Akt has to be phosphorylated (in Ser473) to achieve the glucose uptake effect of insulin (Non-Patent Document 2: Hajduch et al., *FEBS Letters*, 492, 199, (2001)). However, the relationship between the effects of the above glucose uptake enhancers and the Akt phosphorylation has not been known.

Patent Document 1: WO 02/44180
Patent Document 2: WO 2005/068467
Patent Document 3: WO 2005/042536
Patent Document 4: WO 2006/118341
Non-Patent Document 1: Sheehan et al., *Clinical Medicine & Research*, 1, 189, (2003)
Non-Patent Document 2: Hajduch et al., *FEBS Letters*, 492, 199, (2001)

DISCLOSURE OF THE INVENTION

Problems that the Invention is to Solve

As described above, unlike the conventional antidiabetic agents, the glucose uptake enhancer can enhance the glucose uptake activity of a adipocyte, etc. like insulin, and thereby is expected to be a novel useful antidiabetic agent. However, the mechanism of action of the glucose uptake enhancer is not known.

Under such circumstances, the inventors have found an intracellular protein that binds to the glucose uptake enhancer to cause its effect (hereinafter referred to as the target molecule (of the effect)) and a molecular mechanism that produces the effect (hereinafter referred to as the mechanism of action). The present invention has been accomplished based on the findings. Thus, according to the invention, there are provided a compound and an antidiabetic agent having a hypoglycemic effect described below, a method for screening the compound or the antidiabetic agent, a probe compound usable in the screening method, etc.

(1) A method for screening a hypoglycemic compound, comprising using a compound represented by the following general formula (I) or a pharmaceutically acceptable salt thereof (herein after referred to as "said compound") and a trimeric GTP-binding protein β subunit (herein after referred to as "said protein"), by measuring an inhibitory activity of a test substance against binding of the said compound to the said protein:

[Chemical Formula 1]

General Formula (I)

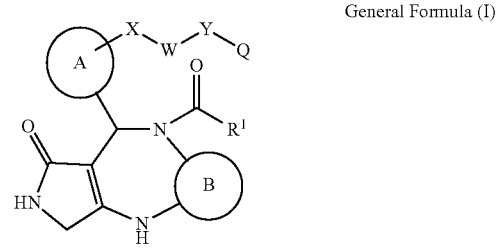

wherein in the general formula (I), A and B may be the same or different and independently represent an optionally substituted aromatic ring, an optionally substituted heterocyclic ring, or an optionally substituted aliphatic ring;

$R^1$ represents a lower alkyl group, a lower alkenyl group, a lower alkynyl group, or a lower alkoxy group, the groups being optionally substituted by 1 to 3 substituents;

—X— and —Y— may be the same or different and independently represent a hydrogen atom, —O—, —NR²—, —S—, —SO—, —SO₂—, —CH₂—, —CR³R⁴—, —COO—, —CONR²—, or —CO—, in which $R^2$ represents a hydrogen atom, an optionally substituted lower alkyl group, an optionally substituted acyl group, an optionally substituted alkoxycarbonyl group, an optionally substituted carbamoyl group, or an optionally substituted sulfonyl group, and $R^3$ and $R^4$ may be the same or different and independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group;

—W— represents an optionally substituted alkyl chain having 1 to 20 carbon atoms, and 1 to 10 carbon atoms in the alkyl chain may be replaced by —O—, —NR$^5$—, —S—, —SO—, —SO$_2$—, or —CO—, in which R$^5$ represents a hydrogen atom, an optionally substituted lower alkyl group, an optionally substituted acyl group, an optionally substituted alkoxycarbonyl group, an optionally substituted carbamoyl group, or an optionally substituted sulfonyl group;

Q represents a hydrogen atom, biotin, a fluorophore, a chromophore, a chemiluminescent functional group, an enzyme, a solid phase, a diazo group, or an azido group;

one or more atoms in the formula may be (a) radioisotope(s);

with the proviso that:

i) in the optionally substituted groups, each substituent is selected from the group consisting of halogen atoms, a hydroxyl group, alkyl groups, mercapto groups, alkoxy groups, alkylthio groups, alkylsulfonyl groups, acyl groups, acyloxy groups, amino groups, alkylamino groups, a carboxyl group, alkoxycarbonyl groups, carbamoyl groups, a nitro group, a cyano group, a trifluoromethyl group, aryl groups, heteroaryl groups, diazo groups, and azido groups (preferably halogen atoms, a hydroxyl group, amino groups, lower alkylamino groups, aryl groups, heteroaryl groups, lower alkyl groups, and lower alkoxy groups), and the substituent may be labeled with biotin, a fluorophore, a chromophore, a chemiluminescent moiety, or an enzyme;

ii) when —X— is a hydrogen atom, —W—, —Y—, and Q do not exist; and iii) when —Y— is a hydrogen atom, Q does not exist.

(2) A method according to (1), wherein in the lactam compound represented by the general formula (I), —X— and —Y— are other than a hydrogen atom, Q is biotin, a fluorophore, a chromophore, a chemiluminescent functional group, or an enzyme, and each substituent in the optionally substituted groups is not labeled with biotin, a fluorophore, a chromophore, a chemiluminescent moiety, or an enzyme.

(3) A method according to (1), wherein in the lactam compound represented by the general formula (I), —X— and —Y— are other than a hydrogen atom, Q is a hydrogen atom, a diazo group, or an azido group, and each substituent in the optionally substituted groups is not labeled with biotin, a fluorophore, a chromophore, a chemiluminescent moiety, or an enzyme.

(4) A method according to (1), wherein in the lactam compound represented by the general formula (I), X is a hydrogen atom, and at least one atom in the general formula (I) is a radioisotope.

(5) A method according to any one of (1) to (4), comprising the steps of: (A) contacting the compound represented by the general formula (I) or the pharmaceutically acceptable salt thereof (the said compound) with the trimeric GTP-binding protein β subunit (the said protein); (B) contacting the said compound with the said protein in the presence of the test substance; and (C) measuring the inhibitory activity of the test substance against the binding of the said compound to the said protein.

(5a) A method according to (5), wherein the method is for measuring the inhibitory activity of the test substance against the binding of the said compound to the said protein by measuring the amount of the said compound bonded to the solid phase after contacting the said compound with the said protein fixed to a solid phase, in the presence or absence of the test substance.

(5b) A method according to (5), wherein the method is for measuring the inhibitory activity of the test substance against the binding of the said compound to the said protein by measuring the amount of the said protein bonded to the solid phase after contacting the said protein with the said compound fixed to a solid phase, in the presence or absence of the test substance.

(5c) A method according to (5), wherein the method is for measuring the inhibitory activity of the test substance against the binding of the said compound to the said protein by measuring the binding amount of the said protein and the said compound after contacting the said protein with the said compound in the presence or absence of the test substance.

(5d) A method according to any one of (5a) to (5c), wherein the method is for measuring the inhibitory activity of the test substance against the binding of the said compound to the said protein by comparing a binding amount obtained by the contact in the presence of the test substance with a binding amount obtained by the contact in the absence of the test substance.

(5e) A method according to (5), further comprising the step of measuring the activity of the test substance in enhancing the enzymatic activity of phosphoinositide 3-kinase (particularly a subtype β) in the presence of the trimeric GTP-binding protein β subunit or in the binding state with the trimeric GTP-binding protein β subunit.

(5f) A method according to (5) or (5e), further comprising the step of measuring the activity of the test substance in phosphorylation of Akt.

(5g) A method according to (5), (5e), or (5f), further comprising the step of measuring the glucose uptake activity of the test substance.

(6) A method according to any one of (1) to (4), wherein the method for screening the hypoglycemic compound by measuring the inhibitory activity of the test substance against the binding of the compound represented by the general formula (I) or the pharmaceutically acceptable salt thereof (the said compound) to the trimeric GTP-binding protein β subunit uses a cell, a tissue, or an extract thereof containing the trimeric GTP-binding protein β subunit.

(7) A method for identifying a hypoglycemic compound, comprising the steps of: (A) fixing a trimeric GTP-binding protein β subunit (herein after referred to as "said protein") to a solid phase; (B) contacting a test substance with the said protein; and (C) eluting a compound bound to the said protein in the step of (B) by using a solution containing a compound represented by the general formula (I) or a pharmaceutically acceptable salt thereof (herein after referred to as "said compound"), an acid, a base, or a denaturant.

(8) An antidiabetic agent comprising, as an active ingredient, a hypoglycemic compound capable of binding to a trimeric GTP-binding protein β subunit.

(8a) A method for treating diabetes, comprising administering to a mammal an effective amount of a hypoglycemic compound capable of binding to a trimeric GTP-binding protein β subunit.

(8b) Use of a hypoglycemic compound capable of binding to a trimeric GTP-binding protein β subunit for the treatment of diabetes.

(8c) Use of a hypoglycemic compound capable of binding to a trimeric GTP-binding protein β subunit for the manufacture of an antidiabetic agent.

(9) An antidiabetic agent comprising, as an active ingredient, a hypoglycemic compound having a main effect of binding to a trimeric GTP-binding protein β subunit and enhancing an enzymatic activity of phosphoinositide 3-kinase.

(9a) A method for treating diabetes, comprising administering to a mammal an effective amount of a hypoglycemic compound having a main effect of binding to a trimeric GTP-binding protein β subunit and enhancing an enzymatic activity of phosphoinositide 3-kinase.

(9b) Use of a hypoglycemic compound having a main effect of binding to a trimeric GTP-binding protein β subunit and enhancing an enzymatic activity of phosphoinositide 3-kinase for the treatment of diabetes.

(9c) Use of a hypoglycemic compound having a main effect of binding to a trimeric GTP-binding protein β subunit and enhancing an enzymatic activity of phosphoinositide 3-kinase for the manufacture of an antidiabetic agent.

(10) An antidiabetic agent comprising, as an active ingredient, a compound capable of binding to the same site of a trimeric GTP-binding protein β subunit, where the compound represented by the general formula (I) binds to.

(10a) A method for treating diabetes, comprising administering to a mammal an effective amount of a compound capable of binding to the same site of a trimeric GTP-binding protein β subunit, where the compound represented by the general formula (I) binds to.

(10b) Use of a compound capable of binding to the same site of a trimeric GTP-binding protein β subunit, where the compound represented by the general formula (I) binds to, for the treatment of diabetes.

(10c) Use of a compound capable of binding to the same site of a trimeric GTP-binding protein β subunit, where a compound represented by the general formula (I) binds to, for the manufacture of an antidiabetic agent.

(10d) An antidiabetic agent comprising, as an active ingredient, a compound capable of binding to a trimeric GTP-binding protein β subunit in competition manner with the compound represented by the general formula (I).

(11) A method for screening a hypoglycemic compound, characterized by detecting a compound capable of further enhancing a phosphoinositide 3-kinase enzymatic activity-enhancing effect of a trimeric GTP-binding protein β subunit.

(12) A method for screening a hypoglycemic compound, characterized by detecting a compound capable of enhancing binding of phosphoinositide 3-kinase to a trimeric GTP-binding protein β subunit.

(13) A method according to (11) or (12), characterized in that the phosphoinositide 3-kinase is of subtype β.

(14) A compound represented by the following general formula (I) or a pharmaceutically acceptable salt thereof:

[Chemical Formula 2]

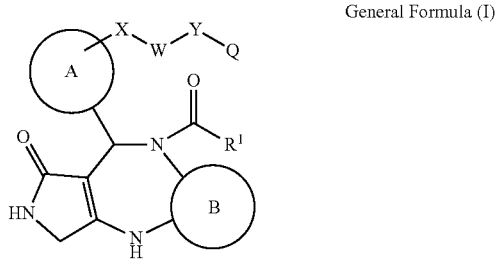

General Formula (I)

wherein in the general formula (I), A and B may be the same or different and independently represent an optionally substituted aromatic ring, an optionally substituted heterocyclic ring, or an optionally substituted aliphatic ring;

$R^1$ represents a lower alkyl group, a lower alkenyl group, a lower alkynyl group, or a lower alkoxy group, the groups being optionally substituted by 1 to 3 substituents;

—X— and —Y— may be the same or different and independently represent a hydrogen atom, —O—, —$NR^2$—, —S—, —SO—, —$SO_2$—, —$CH_2$—, —$CR^3R^4$—, —COO—, —$CONR^2$—, or —CO—, in which $R^2$ represents a hydrogen atom, an optionally substituted lower alkyl group, an optionally substituted acyl group, an optionally substituted alkoxycarbonyl group, an optionally substituted carbamoyl group, or an optionally substituted sulfonyl group, and $R^3$ and $R^4$ may be the same or different and independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group;

—W— represents an optionally substituted alkyl chain having 1 to 20 carbon atoms, and 1 to 10 carbon atoms in the alkyl chain may be replaced by —O—, —$NR^5$—, —S—, —SO—, —$SO_2$—, or —CO—, in which $R^5$ represents a hydrogen atom, an optionally substituted lower alkyl group, an optionally substituted acyl group, an optionally substituted alkoxycarbonyl group, an optionally substituted carbamoyl group, or an optionally substituted sulfonyl group;

Q represents a hydrogen atom, biotin, a fluorophore, a chromophore, a chemiluminescent functional group, an enzyme, a solid phase, a diazo group, or an azido group;

one or more atoms in the formula may be a radioisotope; with the proviso that:

i) in the optionally substituted groups, each substituent is selected from the group consisting of halogen atoms, a hydroxyl group, alkyl groups, mercapto groups, alkoxy groups, alkylthio groups, alkylsulfonyl groups, acyl groups, acyloxy groups, amino groups, alkylamino groups, a carboxyl group, alkoxycarbonyl groups, carbamoyl groups, a nitro group, a cyano group, a trifluoromethyl group, aryl groups, heteroaryl groups, diazo groups, and azido groups, and the substituent may be labeled with biotin, a fluorophore, a chromophore, a chemiluminescent moiety, or an enzyme;

ii) when —X— is a hydrogen atom, —W—, —Y—, and Q do not exist;

iii) when —Y— is a hydrogen atom, Q does not exist; and the compound of the general formula (I) satisfies one of the following conditions a) to f):

a) —X— and —Y— are other than a hydrogen atom, and Q is biotin, a fluorophore, a chromophore, a chemiluminescent functional group, or an enzyme;

b) —X— and —Y— are other than a hydrogen atom, and Q is a diazo group or an azido group;

c) —X— and —Y— are other than a hydrogen atom, and Q is a solid phase;

d) at least one atom is a radioisotope;

e) substituted with at least one substituent which is labeled with biotin, a fluorophore, a chromophore, a chemiluminescent moiety, or an enzyme; or f) substituted with at least one diazo group or azido group as a substituent.

(15) A compound or a pharmaceutically acceptable salt thereof according to (14), wherein —X— and —Y— are other than a hydrogen atom, and Q is biotin, a fluorophore, a chromophore, a chemiluminescent functional group, or an enzyme.

(16) A compound or a pharmaceutically acceptable salt thereof according to (15), wherein each substituent in the optionally substituted groups is not labeled with biotin, a fluorophore, a chromophore, a chemiluminescent moiety, or an enzyme.

(17) A compound or a pharmaceutically acceptable salt thereof according to (14), wherein —X— and —Y— are other than a hydrogen atom, and Q is a diazo group or an azido group.

(18) A compound or a pharmaceutically acceptable salt thereof according to (17), wherein each substituent in the optionally substituted groups is not labeled with biotin, a fluorophore, a chromophore, a chemiluminescent moiety, or an enzyme.

(19) A compound or a pharmaceutically acceptable salt thereof according to (14), wherein —X— and —Y— are other than a hydrogen atom, and Q is a solid phase.

(20) A compound or a pharmaceutically acceptable salt thereof according to (14), wherein at least one atom in the general formula (I) is (a) radioisotope(s).

(21) A compound or a pharmaceutically acceptable salt thereof according to (20), wherein X is a hydrogen atom.

(22) A compound or a pharmaceutically acceptable salt thereof according to (14), wherein the compound has at least one substituent which is labeled with biotin, a fluorophore, a chromophore, a chemiluminescent moiety, or an enzyme.

(23) A compound or a pharmaceutically acceptable salt thereof according to (14), wherein the compound has at least one diazo group or azido group as a substituent.

(24) A compound represented by the following general formula (I) or a pharmaceutically acceptable salt thereof:

[Chemical Formula 3]

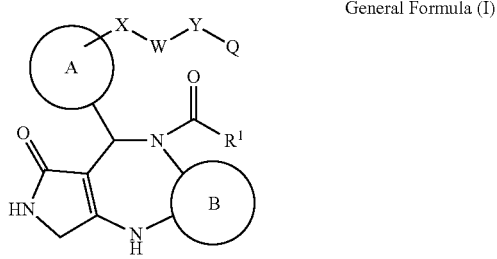

General Formula (I)

wherein in the general formula (I), A and B may be the same or different and independently represent an optionally substituted aromatic ring, an optionally substituted heterocyclic ring, or an optionally substituted aliphatic ring;

$R^1$ represents a lower alkyl group, a lower alkenyl group, a lower alkynyl group, or a lower alkoxy group, the groups being optionally substituted by 1 to 3 substituents;

—X— and —Y— may be the same or different and independently represent —O—, —$NR^2$—, —S—, —SO—, —$SO_2$—, —$CH_2$—, —$CR^3R^4$—, —COO—, —$CONR^2$—, or —CO—, in which $R^2$ represents a hydrogen atom, an optionally substituted lower alkyl group, an optionally substituted acyl group, an optionally substituted alkoxycarbonyl group, an optionally substituted carbamoyl group, or an optionally substituted sulfonyl group, and $R^3$ and $R^4$ may be the same or different and independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group;

—W— represents an optionally substituted alkyl chain having 1 to 20 carbon atoms, and 1 to 10 carbon atoms in the alkyl chain may be replaced by —O—, —$NR^5$—, —S—, —SO—, —$SO_2$—, or —CO—, in which $R^5$ represents a hydrogen atom, an optionally substituted lower alkyl group, an optionally substituted acyl group, an optionally substituted alkoxycarbonyl group, an optionally substituted carbamoyl group, or an optionally substituted sulfonyl group;

Q represents a hydrogen atom; and with the proviso that:

i) in the optionally substituted groups, each substituent is selected from the group consisting of halogen atoms, a hydroxyl group, alkyl groups, mercapto groups, alkoxy groups, alkylthio groups, alkylsulfonyl groups, acyl groups, acyloxy groups, amino groups, alkylamino groups, a carboxyl group, alkoxycarbonyl groups, carbamoyl groups, a nitro group, a cyano group, a trifluoromethyl group, aryl groups, heteroaryl groups, diazo groups, and azido groups.

SUMMARY OF THE INVENTION

According to the present invention, there are provided the compounds and the antidiabetic agents having a hypoglycemic effect, methods for screening the compounds and the antidiabetic agents, probe compounds usable in the screening methods, etc.

BRIEF DESCRIPTION OF THE DRAWINGS

FIG. 10 is a graph showing the evaluation results of the ability of a compound for binding to the Gβ in a Gβγ2-Myc-binding screening system;

FIG. 14 is a graph showing the effects of Compounds 1 and 6 on enhancing PI3-kinase β activity;

FIG. 15 is a view showing the effects of Compounds 1 and 6 on enhancing the binding of the Gβ1γ2-Myc to phosphoinositide 3-kinase (PI3-kinase) β;

FIG. 16 is a view showing the results of Gβ knockdown using a siRNA (the right part) and Akt phosphorylation by Compound 6 in a knocked-down cell (the left part)

DETAILED DESCRIPTION OF THE INVENTION

Figure 1:
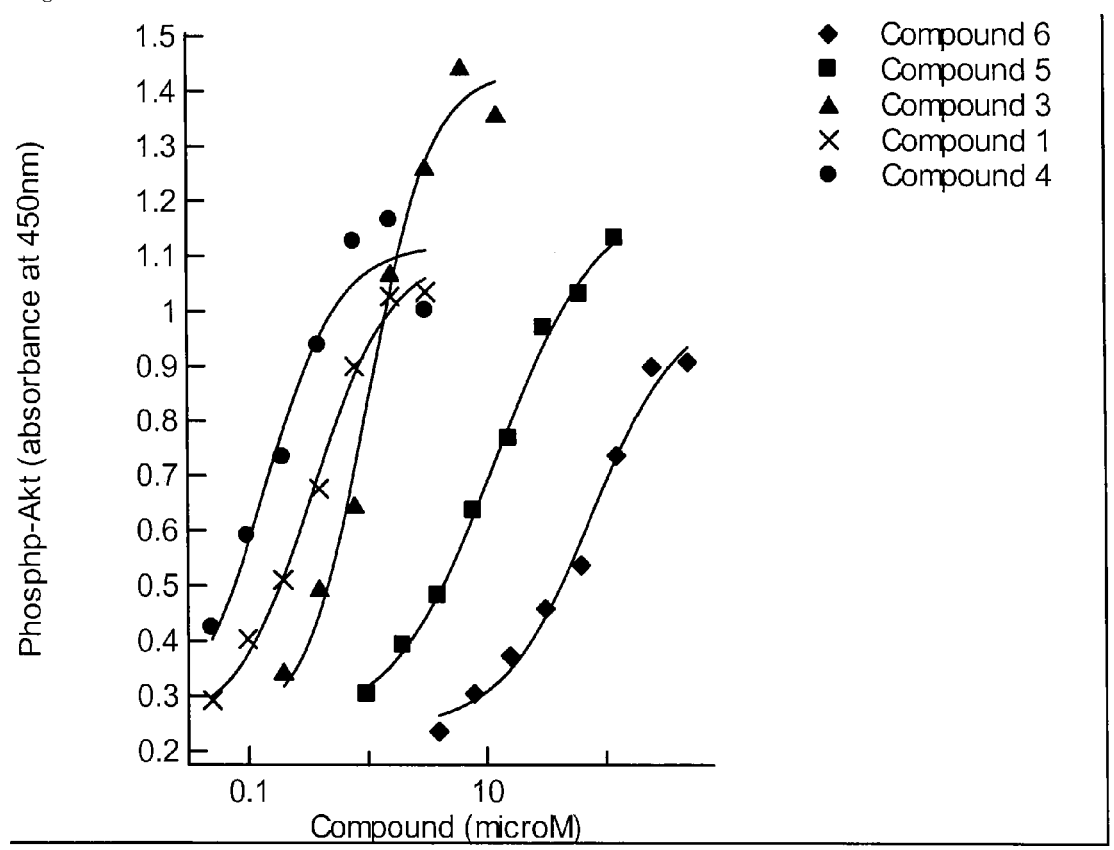
FIG. 1 is a graph showing the results of Akt phosphorylation activity measurement in Example 13.

In this description, the term "lower" means for example that a group has a 1 to 6 carbon atoms. The carbon numbers of the alkyl, alkenyl, alkynyl, alkoxy, and acyl groups are preferably up to 6, more preferably up to 3.

The term "aromatic ring" as used herein indicates a mono- or bi-cyclic, aromatic ring composed of carbon atoms, such as a benzene ring, a naphthalene ring, an indene ring, a fluorene ring, etc., and preferably are a benzene ring, a naphthalene ring, etc.

The term "heterocyclic ring" as used herein indicates heterocyclic ring of 1-3 rings each comprising 4-9 members which is composed of carbon and nitrogen, oxygen, sulfur, etc. The heterocyclic ring include, for example, a pyridine ring, a dihydropyran ring, a pyridazine ring, a pyrimidine ring, a pyrazine ring, a pyrrole ring, a furan ring, a thiophene ring, an oxazole ring, an isoxazole ring, a pyrazole ring, an imidazole ring, a thiazole ring, an isothiazole ring, a thiadiazole ring, a pyrrolidine ring, a piperidine ring, a piperazine ring, an indole ring, an isoindole ring, a benzofuran ring, an isobenzofuran ring, a benzothiophene ring, a benzopyrazole ring, a benzimidazole ring, a benzoxazole ring, a benzothiazole ring, a purine ring, a pyrazolopyridine ring, a quinoline ring, an isoquinoline ring, a naphthyridine ring, a quinazoline ring, a benzodiazepine ring, a carbazole ring, a dibenzofuran ring, etc., preferably a pyridine ring, a furan ring, a thiophene ring, a benzofuran ring, a benzothiophene ring, an indole ring, etc., more preferably a thiophene ring, a benzofuran ring, a benzothiophene ring, an indole ring, etc.

The term "aliphatic ring" as used herein indicates a mono- or bi-cyclic, aliphatic ring composed of carbon atoms and includes such as a cyclopropane ring, a cyclobutane ring, a cyclopentane ring, a cyclohexane ring, a cycloheptane ring, a cyclooctane ring, a decalin ring, a norbornane ring, etc., preferably a cyclohexane ring.

The lower alkyl group denotes a straight-chain, branched-chain, or cyclic alkyl group having 1 to 6 carbon atoms, preferably 1 to 3 carbon atoms. The lower alkyl group includes, for example a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a cyclopropyl group, a cyclobutyl group, a cyclopentyl group, a cyclohexyl group, etc., and preferably are a methyl group, an ethyl group, etc.

The lower alkoxy group is an alkoxy group containing a lower alkyl group.

The aryl group is a mono- or bi-cyclic aromatic substituent composed of 5 to 12 carbon atoms. Specifically, the aryl group includes, for example a phenyl group, an indenyl group, a naphthyl group, a fluorenyl group, etc., preferably a phenyl group, etc.

The halogen atom includes a fluorine atom, a chlorine atom, a bromine atom, or an iodine atom.

The alkyl group is a straight-chain, branched-chain, or cyclic alkyl group having 1 to 18 carbon atoms. Specifically, the alkyl group includes, for example a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a tert-octyl group, a cyclopropyl group, a cyclobutyl group, a cyclopentyl group, a cyclohexyl group, a 1-adamantyl group, etc., and preferably are an n-hexyl group, an n-heptyl group, an n-octyl group, an n-nonyl group, an n-decyl group, an n-undecyl group, an n-dodecyl group, an isopropyl group, an isobutyl group, a sec-butyl group, a tert-butyl group, an isopentyl group, a tert-pentyl group, a neopentyl group, a 2-pentyl group, a 3-pentyl group, a 3-hexyl group, a 2-hexyl group, a tert-octyl group, a cyclopropyl group, a cyclobutyl group, a cyclopentyl group, a cyclohexyl group, a 1-adamantyl group, etc., more preferably are an isopropyl group, a tert-butyl group, a tert-octyl group, a 1-adamantyl group, etc.

The alkenyl group is a straight-chain, branched-chain, or cyclic alkenyl group having 1 to 6 carbon atoms. Specifically, the alkenyl group includes, for example a vinyl group, a 1-propenyl group, a 2-propenyl group, an isopropenyl group, a 1-butenyl group, a 2-butenyl group, a 3-butenyl group, etc. The alkynyl group is a straight- or branched-chain alkynyl group having 1 to 6 carbon atoms. Specifically, the alkynyl group includes, for example an ethynyl group, a 1-propynyl group, a 2-propynyl group, a 1-butynyl group, a 2-butynyl group, a 3-butynyl group, etc.

The alkoxy group denotes an alkoxy group containing a straight-chain, branched-chain, or cyclic alkyl group having 1 to 18 carbon atoms, preferably 1 to 8 carbon atoms. The alkoxy group includes, for example a methoxy group, an ethoxy group, an n-propoxy group, an n-butoxy group, an n-pentyloxy group, an n-hexyloxy group, an n-heptyloxy group, an n-octyloxy group, an n-nonyloxy group, an n-decyloxy group, an n-undecyloxy group, an n-dodecyloxy group, an isopropoxy group, an isobutoxy group, a sec-butoxy group, a tert-butoxy group, a cyclopropyloxy group, a cyclobutoxy group, a cyclopentyloxy group, a cyclohexyloxy group, a cycloheptyloxy group, a 2-cyclohexylethoxy group, a 1-adamantyloxy group, a 2-adamantyloxy group, a 1-adamantylmethoxy group, a 2-(1-adamantyl)ethoxy group, a trifluoromethoxy group, etc., preferably a methoxy group, an ethoxy group, an n-propoxy group, an isopropoxy group, an n-butoxy group, a tert-butoxy group, an n-pentyloxy group, or an n-hexyloxy group.

The alkylthio group denotes an alkylthio group containing a straight-chain, branched-chain, or cyclic alkyl group having 1 to 12 carbon atoms, preferably 1 to 6 carbon atoms. The alkylthio group includes, for example a methylthio group, an ethylthio group, an n-propylthio group, an isopropylthio group, an n-butylthio group, an isobutylthio group, a sec-butylthio group, a tert-butylthio group, a cyclopropylthio group, a cyclobutylthio group, a cyclopentylthio group, a cyclobutylthio group, etc.

The alkylsulfonyl group denotes an alkylsulfonyl group containing a straight-chain, branched-chain, or cyclic alkyl group having 1 to 12 carbon atoms. Specifically, the alkylsulfonyl group includes, for example a methanesulfonyl group, an ethanesulfonyl group, a propanesulfonyl group, a butanesulfonyl group, a pentanesulfonyl group, a hexanesulfonyl group, a heptanesulfonyl group, an octanesulfonyl group, a nonanesulfonyl group, a decanesulfonyl group, an undecanesulfonyl group, a dodecanesulfonyl group, etc.

The acyl group denotes a formyl group, an acyl group containing a straight-chain, branched-chain, or cyclic alkyl group having 1 to 6 carbon atoms, an acyl group containing a straight-chain, branched-chain, or cyclic alkenyl group having 1 to 6 carbon atoms, an acyl group containing a straight-chain, branched-chain, or cyclic alkynyl group having 1 to 6 carbon atoms, or an acyl group containing an optionally substituted aryl group. The acyl group includes, for example a formyl group, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a benzoyl group, a naphthoyl group, etc.

The acyloxy group is a formyloxy group, an acyloxy group containing a straight-chain, branched-chain, or cyclic alkyl group having 1 to 6 carbon atoms, or an acyloxy group containing an optionally substituted aryl group. Specifically, the acyloxy group includes, for example a formyloxy group, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a methacryloyloxy group, a crotonoyloxy group, an isocrotonoyloxy group, a benzoyloxy group, a naphthoyloxy group, etc.

The alkylamino group denotes an amino group substituted with one or two alkyl groups. The alkyl group in the alkylamino group includes the same as the above-described alkyl group. The alkylamino group includes, for example an amino group, a methylamino group, an ethylamino group, a propylamino group, an isopropylamino group, a dimethylamino group, a diethylamino group, a dipropylamino group, a diisopropylamino group, a methylethylamino group, etc. The alkylamino group preferably has 1 to 6 carbon atoms.

The alkoxycarbonyl group denotes an alkoxycarbonyl group containing a straight-chain, branched-chain, or cyclic alkyl group having 1 to 8 carbon atoms. The alkoxycarbonyl group includes, for example a methoxycarbonyl group, an ethoxycarbonyl group, a propoxycarbonyl group, an isopropoxycarbonyl group, an n-butoxycarbonyl group, an isobutoxycarbonyl group, a sec-butoxycarbonyl group, a tert-butoxycarbonyl group, a benzyloxycarbonyl group, etc.

The carbamoyl group denotes a carbamoyl group containing a straight-chain, branched-chain, or cyclic alkyl group having 1 to 6 carbon atoms on the nitrogen. The carbamoyl group includes, for example a carbamoyl group, an N-methylcarbamoyl group, an N-ethylcarbamoyl group, an N,N-dimethylcarbamoyl group, an N-pyrrolidylcarbonyl group, an N-piperidylcarbonyl group, an N-morpholinylcarbonyl group, etc.

The sulfonyl group denotes a sulfonyl group containing a straight-chain, branched-chain, or cyclic alkyl group having 1 to 6 carbon atoms on the sulfur. The sulfonyl group includes, for example a methylsulfonyl group, an ethylsulfonyl group, a propylsulfonyl group, a butylsulfonyl group, etc.

The solid phase denotes a solid, a semisolid, or a solid solution to which the compound or protein can be fixed. The solid phase includes, for example, a container (such as a tube, a well, or a plate), a carrier (such as a resin or a gel), a sheet, a powder, or a rod of a resin, a polymer, etc. but is not limited to the specific examples, and may include any substance as long as the compound or protein can be fixed thereto.

More specifically, in the formula (I), A is preferably selected from a benzene ring, a naphthalene ring, an indene ring, a fluorene ring, a pyridine ring, a dihydropyran ring, a pyridazine ring, a pyrimidine ring, a pyrazine ring, a pyrrole ring, a furan ring, a thiophene ring, an oxazole ring, an isoxazole ring, a pyrazole ring, an imidazole ring, a thiazole ring, an isothiazole ring, a thiadiazole ring, a pyrrolidine ring, a piperidine ring, a piperazine ring, an indole ring, an isoindole ring, a benzofuran ring, an isobenzofuran ring, a benzothiophene ring, a benzopyrazole ring, a benzimidazole ring, a benzoxazole ring, a benzothiazole ring, a purine ring, a pyrazolopyridine ring, a quinoline ring, an isoquinoline ring, a naphthyridine ring, a quinazoline ring, a benzodiazepine ring, a carbazole ring, a dibenzofuran ring, a cyclopropane ring, a cyclobutane ring, a cyclopentane ring, a cyclohexane ring, a cycloheptane ring, a cyclooctane ring, a decalin ring, a norbornane ring, etc., more preferably selected from a benzene ring, a pyridine ring, a furan ring, a thiophene ring, a benzofuran ring, a benzothiophene ring, an indole ring, a quinoline ring, a benzothiazole ring, a benzoxazole ring, etc., further preferably selected from a benzene ring, a thiophene ring, a benzofuran ring, a benzothiophene ring, an indole ring, a quinoline ring, etc.

In the formula (I), B is preferably selected from a benzene ring, a naphthalene ring, an indene ring, a fluorene ring, a pyridine ring, a dihydropyran ring, a pyridazine ring, a pyrimidine ring, a pyrazine ring, a pyrrole ring, a furan ring, a thiophene ring, an oxazole ring, an isoxazole ring, a pyrazole ring, an imidazole ring, a thiazole ring, an isothiazole ring, a thiadiazole ring, a pyrrolidine ring, a piperidine ring, a piperazine ring, an indole ring, an isoindole ring, a benzofuran ring, an isobenzofuran ring, a benzothiophene ring, a benzopyrazole ring, a benzimidazole ring, a benzoxazole ring, a benzothiazole ring, a purine ring, a pyrazolopyridine ring, a quinoline ring, an isoquinoline ring, a naphthyridine ring, a quinazoline ring, a benzodiazepine ring, a carbazole ring, a dibenzofuran ring, a cyclopropane ring, a cyclobutane ring, a cyclopentane ring, a cyclohexane ring, a cycloheptane ring, a cyclooctane ring, a decalin ring, a norbornane ring, etc., and more preferably selected from a benzene ring, a cyclohexane ring, etc.

In the formula (I), $R^1$ is preferably selected from lower alkyl groups, lower alkenyl groups, lower alkynyl groups, lower alkoxy groups and the like, substituted with a hydroxyl group, an aryl group (an aromatic ring group), a heteroaryl group (a heterocyclic ring group), a cycloalkyl group, an alkoxy group, or a halogen atom, etc., more preferably selected from aryl-$C_{1-2}$ alkyl or heteroaryl-$C_{1-2}$ alkyl (such as pyridylmethyl, thiazolylmethyl), a hydroxymethyl group, a methoxymethyl group.

In the formula (I), —X—W—Y— is preferably —O—$(CH_2)_{1-2}$—O—$(CH_2)_{1-2}$—NH—, —O—$(CH_2)_{1-2}$—O—$(CH_2)_{1-2}$—NHCO$(CH_2)_{4-6}$—NH—, etc.

A method for producing the compound represented by the formula (I) or an analog thereof is described, for example, in Patent Documents 1 to 4. The compound represented by the formula (I) can be easily produced based on the descriptions of the documents and common technical knowledge of those skilled in the art.

In this description, the terms "probe compound" and "probe molecule" refer to a low-molecular compound useful for determining the "activity target molecule" or the "mechanism of action" of the "glucose uptake enhancer", and/or a low-molecular compound useful in the method for screening the "glucose uptake enhancer" or the "hypoglycemic compound".

The term "glucose uptake enhancer" as used herein indicates an agent or a compound that increases the glucose uptake ability of a cell or tissue capable of physiologically uptaking sugars (such as glucose or an analog thereof) when administered. The glucose uptake enhancer includes, for example, a compound having an effect of substantially enhancing the glucose uptake of the cell, selected from compounds described in Patent Documents 1 to 4, such as the compound represented by the general formula (I) (wherein X is a hydrogen atom).

The term "target molecule (of the effect)" as used herein indicates a protein expressed in a cell, to which the glucose uptake enhancer binds directly or indirectly. Particularly the target molecule (of the effect) may be a protein needed for achieving the glucose uptake activity or the Akt phosphorylation.

The term "mechanism of action" denotes reactions caused after the glucose uptake enhancer binds to the target molecule, such as enhancement/reduction of the binding between two or more protein molecules, enhancement/reduction of the enzymatic activity, and change of the phosphorylation degree of the protein. Particularly the mechanism of action denotes a change needed for achieving the glucose uptake activity or the Akt phosphorylation.

The term "hypoglycemic compound" as used herein indicates a compound that substantially lowers the blood glucose level of a living body when administered in vivo. The hypoglycemic compound can be used as an antidiabetic agent.

[1] Summary of the Present Invention (Detection of Activity Index of "Glucose Uptake Enhancer")

In view of the above described background, the inventors synthesized several compounds having a structure represented by the general formula (I) (wherein X is a hydrogen atom) described in Patent Documents 1 to 4 (patents on "glucose uptake enhancer") and several compounds structurally developed by the course of intense research based on the structure, and measured and compared their Akt phosphorylation activities and glucose uptake activities. The phosphorylation of Akt is known to be caused in the glucose uptake enhancement action of insulin (Non-Patent Document 2). The result showed that a good correlation between the Akt phosphorylation activity and the glucose uptake activity was observed in the synthesized compounds. Thus, it was determined that the Akt phosphorylation was caused also in the glucose uptake action of the glucose uptake enhancers.

(Probe Compound)

Furthermore, the inventors designed a plurality of compounds useful for determining the target molecule (of the effect) and the mechanism of action (hereinafter referred to as "probe compounds") based on the compounds described in Patent Documents 1 to 4. The "probe compounds" have the scaffold considered necessary for the glucose uptake enhancing activity of the compounds described in Patent Documents 1 to 4, and the various useful compounds bound by a residue that can be fixed by a linker moiety to a solid phase (such as a container or a carrier), or bound by a residue useful for detecting the binding, or substituted by (a) radioisotope(s) that can be detected, were obtained by conducting such design and synthesis.

The probe compounds are useful for determining the target molecule and the mechanism of action of the glucose uptake enhancer as described below. In addition, the probe compounds can be used in screening for finding a novel "glucose uptake enhancer".

It is widely known that a method for fixing the compound to a solid phase such as carrier or container through a linker and detecting it, or for determining the compound having the residue useful for detecting the binding. However, it is generally known that the probe compound may lose the essential activity of the scaffold, depending on the position of the linker moiety in the probe compound. The inventors made it possible to design and synthesize a compound that had the residue capable of being fixed to the solid phase (such as the container or carrier) or the residue useful for detecting the binding without losing the essential glucose uptake enhancing activity posed by the compound, and found the "probe compound".

(Activity Target Molecule)

The inventors further investigated an intracellular protein to which the above probe compound binds, to identify the target molecule of the glucose uptake enhancer described in Patent Documents 1 to 4 by using the above mentioned "probe compound". First, A tritium-containing, radioisotope-labeled derivative of Compound 1 having strong high glucose uptake activity described in Patent Document 3 (the compound of Example 1 to be hereinafter described) was synthesized as an example of the probe compound. The ability of the radioisotope-labeled derivative to bind to a cell membrane of a cultured animal cell, on which the "glucose uptake enhancer" acts, was evaluated. Specifically, the Akt phosphorylation action was measured using a human liver-derived HLF cell as an action index of the glucose uptake enhancer on the cultured animal cell. The Akt phosphorylation action of Compound 1 and the binding activity of the radioisotope-labeled derivative were observed in a saturable manner at approximately the same concentrations. Thus, it was strongly suggested that the protein bound to the radioisotope-labeled derivative was one of the target molecule, which causes the glucose uptake and the Akt phosphorylation by the glucose uptake enhancer.

The inventors made intense research to identify the type of the binding protein (the target molecule). As a result of solubilizing proteins from the cell membrane of the HLF cell by using a detergent, the inventors found an existence of a protein capable of binding with high affinity to the radioisotope-labeled derivative among the solubilized proteins. Furthermore, the inventors selected Compound 2 having an amino group at the end of the linker structure moiety capable of binding to a carrier (the compound of Example 2 to be hereinafter described) from the low-molecular probe compounds capable of binding to the target molecule, and carried out an affinity chromatography using the carrier bound to the compound. Eluting with Compound 4 having strong glucose uptake activity and Akt phosphorylation activity equal to those of Compound 1, the inventors found a protein migrated around 35 to 36 KDa in an SDS polyacrylamide gel electrophoresis. This protein was found to be a trimeric GTP-binding protein β subunit based on the molecular weight, antibody reactivity, and partial amino acid sequence information. The trimeric GTP-binding protein β subunit exists in a trimeric state binding to other α and γ subunits in a cell, and may be in a dimeric state binding to a γ subunit under some circumstances (Non-Patent Document 3: Wettschureck et al., *Physiological Reviews*, 85, 1159, (2005)). It was found that the "glucose uptake enhancer" binds to the trimeric GTP-binding protein β subunit, or the trimer or dimer containing the β subunit. Thus, the trimeric GTP-binding protein (β subunit including the complexes are the target molecule of the "glucose uptake enhancer".

The inventors expressed the trimeric GTP-binding protein β subunit, together with the γ subunit, or with α and γ subunits, in animal and insect cells, and found that the radioisotope-labeled derivative of Compound 1 can bind to a protein extracted or purified therefrom. Furthermore, as a result of intense research, the inventors found that a novel "glucose uptake enhancer" can be screened or produced by measuring the inhibitory activity against the binding of the probe compound to the extracted or purified protein. The invention has been accomplished based on the findings.

The inventors further found that, in the compound detected in the above manner, capable of binding to the trimeric GTP-binding protein β subunit, there is a good correlation between the binding activity and the activity for enhancing the Akt phosphorylation and the glucose uptake in a cell. It is a radically new knowledge previously unknown that the detectable compound in the method above which binds to the trimeric GTP-binding protein β subunit acts to enhance the glucose uptake. According to the invention, there is provided the hypoglycemic agent (i.e. the antidiabetic agent) characterized by binding to the trimeric GTP-binding protein β subunit.

[2] Mechanism of Action According to the Invention

The inventors further researched the mechanism of action of the glucose uptake enhancer based on the above knowledge. As a result, the inventors found from data of various research using an inhibitor that a β or δ subtype of phosphoinositide 3-kinase is involved in the mechanism of action of the "glucose uptake enhancer". It has been reported that the enzymatic activity of phosphoinositide 3-kinase β is enhanced when the enzyme is bound to the trimeric GTP-binding protein β subunit (Non-Patent Document 4: Maier et al., *Journal of Biological Chemistry*, 274, 29311, (1999)). Thus, the inventors found the possibility that the "glucose uptake enhancer" capable of binding to the trimeric GTP-binding protein β subunit increases the activity of phosphoinositide 3-kinase β through the trimeric GTP-binding protein β subunit.

Several compounds capable of binding to the trimeric GTP-binding protein β subunit have been reported. For example, Scott et al. have reported a peptide having an Ser-Ile-Arg-Lys sequence or an analog thereof (Non-Patent Document 5: Scott et al., *The EMBO Journal*, 20, 767, (2001)), and Bonacci et al. have reported a novel trimeric GTP-binding protein β subunit binding compound based on a pharmacofore designed according to the binding peptide and its binding structure (Non-Patent Document 6: Bonacci et al., *Science*, 312, 443, (2006)). Bonacci et al. have further reported that a plurality of compounds capable of binding to the trimeric GTP-binding protein β subunit have different physiological effects, which are effected by the type of the binding to the trimeric GTP-binding protein β subunit. This fact makes it clear that the compounds capable of binding to the trimeric GTP-binding protein β subunit can exhibit various physiological activities depending on the binding positions and the physiological effects thereafter, and also it makes it clear that the physiological effects thereof can be found only from a result of intense research. The inventors intensely investigated the glucose uptake enhancer above and compared the physiological activities of the "glucose uptake enhancer" and a compound M201 reported in Non-Patent Document 6 capable of binding to the trimeric GTP-binding protein β subunit (hereinafter referred to as the N-deacetylcolchicine). As a result, the inventors obtained the following knowledges.

i) The glucose uptake enhancer has a glucose uptake activity, while the N-deacetylcolchicine does not have such an activity.

ii) The glucose uptake enhancer has an Akt phosphorylation activity, while the N-deacetylcolchicine does not have such an activity.

iii) The bindings of glucose uptake enhancer and the N-deacetylcolchicine to the trimeric GTP-binding protein β subunit are not competitive each other.

iv) The glucose uptake enhancer increases the activity of phosphoinositide 3-kinase β in the presence of the trimeric GTP-binding protein β subunit, while the N-deacetylcolchicine is reported to increase the activity of phosphoinositide 3-kinase γ in the presence of the trimeric GTP-binding protein β subunit (it should be noted that the inventors could not observe the reported enhancing action).

Based on the above knowledges, the inventors came to the conclusion that the "glucose uptake enhancer" capable of binding to the trimeric GTP-binding protein β subunit can enhance the activity of the phosphoinositide 3-kinase β through the trimeric GTP-binding protein β subunit.

Phosphoinositide 3-kinase β is reported to be involved in the glucose uptake activity of the insulin (Non-Patent Document 7: Asano et al., *Journal of Biological Chemistry*, 275, 17671, (2000)). It is widely known as signaling pathway that Akt binds to phosphatidylinositol-[3,4,5]-trisphosphate (hereinafter referred to as the PtdIns[3,4,5]P$_3$) generated on the cell membrane by phosphoinositide 3-kinase β, and is activated due to the phosphorylation of the Ser473 thereafter. The Akt phosphorylation is widely recognized to be a upstream signal of the glucose uptake (Non-Patent Document 2). In addition, as described above, it has been reported that the enzymatic activity of phosphoinositide 3-kinase β is enhanced when the enzyme is bound to the trimeric GTP-binding protein β subunit (Non-Patent Document 4: Maier et al., *Journal of Biological Chemistry*, 274, 29311, (1999)). Thus, by comprehensively evaluating the above inventions and the above general information, the inventors have found that one of the glucose uptake enhancing mechanisms of the "glucose uptake enhancer" is such that it binds to the trimeric GTP-binding protein β subunit to enhance the enzymatic activity of phosphoinositide 3-kinase. The invention has been completed based on the finding. Various methods for measuring the concerted action of the trimeric GTP-binding protein β subunit and phosphoinositide 3-kinase have been commonly described in reports (such as Non-Patent Document 4 and Non-Patent Document 10: Kerchner et al., *Journal of Biological Chemistry*, 279, 44554, (2004)). According to the invention, based on the result that the compound capable of binding to the trimeric GTP-binding protein β subunit to enhance the enzymatic activity of the phosphoinositide 3-kinase acted as the "glucose uptake enhancer", there is disclosed a method of screening an antidiabetic compound characterized by detecting a compound capable of enhancing the binding of the trimeric GTP-binding protein β subunit to phosphoinositide 3-kinase.

It is a radically new knowledge previously unknown that the compound capable of binding to the trimeric GTP-binding protein β subunit to enhance the enzymatic activity of phosphoinositide 3-kinase acts to enhance the glucose uptake. Furthermore, the compound having this activity has been unknown. According to the invention, there is provided the hypoglycemic agent (i.e. the antidiabetic agent) characterized by binding to the trimeric GTP-binding protein β subunit to enhance the enzymatic activity of phosphoinositide 3-kinase.

The probe compound, therapeutic agent, screening method, etc. of the invention will be described in detail below.

[3] Probe Compound of the Invention

The probe compound of the invention is the compound represented by the general formula (I) or the pharmaceutically acceptable salt thereof. The lactam compound represented by the general formula (I) is more preferably a compound according to (14) or a pharmaceutically acceptable salt thereof, wherein —X— and —Y— are other than a hydrogen atom, Q is biotin, a fluorophore, a chromophore, a chemiluminescent functional group, or an enzyme, and each substituent in the optionally substituted groups is not labeled with biotin, a fluorophore, a chromophore, a chemiluminescent moiety, or an enzyme. Above all, it is preferred that Q is biotin.

The lactam compound represented by the general formula (I) is further preferably a compound according to (14) or a pharmaceutically acceptable salt thereof, wherein —X— and —Y— are other than a hydrogen atom, Q is a hydrogen atom, a diazo group, or an azido group, and each substituent in the optionally substituted groups is not labeled with biotin, a fluorophore, a chromophore, a chemiluminescent moiety, or an enzyme. Above all, it is preferred that Y is —NH— and Q is a hydrogen atom.

The lactam compound represented by the general formula (I) is particularly preferably a compound according to (14) or a pharmaceutically acceptable salt thereof, wherein X is a hydrogen atom and at least one atom in the general formula (I) is (a) radioisotope(s). Above all, it is preferred that $R^1$ comprises an optionally substituted lower alkyl group, and at least one atom thereof is (a) radioisotope(s).

The compound may be synthesized in accordance with known preparation methods described in Patent Documents 1 to 4, etc. The radiolabeled compound is a compound containing (a) radioisotope(s) such as $^3H$, $^{14}C$, $^{125}I$, $^{32}P$, $^{33}P$, or $^{35}S$ in the molecule, and may be prepared from a starting material containing the radioisotope. For example, the radiolabeled compound may be prepared by using $NaB^3H_4$ instead of $NaBH_4$ for a reduction reaction. The fluorophore-labeled compound may be prepared by bonding a fluorescent compound (such as a fluorescein, coumalin, rhodamine, Texas red, Cy3, Cy5, or Alexa compound) described in *Handbook of Fluorescent Probes and Research Products*, Ninth Edition (Richard P. Haugland, Molecular Probes), etc. to an amino group, a carboxyl group, a hydroxyl group, a thiol group, etc. in a starting material of the desired compound. The chromophore-labeled compound may be prepared by bonding with a dye compound or a highly light absorbent compound comprising a substituted aromatic or heteroaromatic ring (such as a nitrobenzene, nitroaniline, or aminopyridine ring) or a highly conjugated aromatic or heteroaromatic ring (such as a pyrene or acridine ring), more preferably, a residue having a molar absorbance coefficient ($\log_{10}\epsilon$) of 3.5 or more, more preferably 4.0 or more, at a maximal value in a long wavelength region of 230 nm or more, by the same method as the fluorophore labeling, or by crosslinking intermolecures using a crosslinker compound. The chemiluminescent-labeled compound may be prepared by using a compound capable of emitting a light in the presence of an enzyme (such as luciferin), a compound capable of emitting a light in the presence of a metal ion (such as luminol), etc. in the same manner. The enzyme-labeled compound may be prepared by using an enzyme (such as an alkaline phosphatase, a peroxidase, or a β galactosidase) in the same manner.

The compounds of (14) to (23) are useful as the probe molecule for the analysis of the "target molecule" and the "mechanism of action" of the "glucose uptake enhancer". In addition, the compounds can be used in the screening methods and the identification methods for obtaining "hypoglycemic compounds" described in (1) to (7). Also, the compound of (24) is useful as an intermediate for the compound of (14) to (23). The compound of (14) to (24) can be easily produced based on the descriptions of Patent Documents 1 to 4 and common technologies known to those skilled in the art (such as known organic synthesis methods).

[4] Screening Method of the Invention

In the invention, there is provided (1) a method for screening the hypoglycemic compound, by measuring an inhibitory activity of a test substance against binding of the said compound to the said protein with using the compound represented by the general formula (I) (the said compound) and the trimeric GTP-binding protein β subunit (the said protein).

Furthermore, in the invention, there is provided (5) a method for screening the hypoglycemic compound, comprising the steps of:

(A) contacting the compound represented by the general formula (I) (the said compound) with the trimeric GTP-binding protein β subunit (the said protein);

(B) contacting the said compound with the said protein in the presence of the test substance; and (C) measuring the inhibitory activity of the test substance against the binding of the said compound to the said protein.

The "trimeric GTP-binding protein β subunit" may be in the state of a monomer, a dimer with the γ subunit, or a trimer with the α and γ subunits, as long as it substantially has the β subunit. The trimeric GTP-binding protein β subunit may be derived from any organism such as human beings, mice, rat, cattle, pig, or rabbit. The trimeric GTP-binding protein β subunit may be extracted from a cell or tissue existing in nature, and may be extracted from a cell or tissue which expresses the subunit by a genetic engineering procedure. The trimeric GTP-binding protein β subunit may be purified or unpurified. Examples of methods for purifying the trimeric GTP-binding protein β subunit existing in nature include a method reported by Stemweis et al. (Non-Patent Document 8: Stemweis et al., *Journal of Biological Chemistry*, 259, 13806, (1984)). Examples of methods for purifying the trimeric GTP-binding protein β subunit produced by the genetic engineering procedure include a method reported by Kozasa et al. (Non-Patent Document 9: Kozasa et al., *Journal of Biological Chemistry*, 270, 1734, (1995)). The purification method is not limited to the examples.

The trimeric GTP-binding protein β subunit has 1 to 5 subtypes, and any subtypes can be used. As the trimeric GTP-binding protein β subunit existing in nature, the subunit having an amino acid sequence reported for each subtypes or a variant amino acid sequence as long as it substantially maintains the activity can be used. Examples of the amino acid sequences include, but not limited to, those described in SEQ ID NOs.: 16, 20, 24, 28, and 32. For example, also a protein having homology of 80%, 90%, 95%, or 97% or more to the amino acid sequence of SEQ ID NO.: 16, 20, 24, 28, or 32, a protein having an amino acid sequence provided from that of SEQ ID NO.: 16, 20, 24, 28, or 32 by removal, substitution, or addition of one to several amino acids (such as 6 amino acids), etc. may be used in the invention.

The trimeric GTP-binding protein β subunit produced by the genetic engineering procedure having a reported amino acid sequence or a variant amino acid sequence obtained by genetic mutation can be used as long as it substantially maintains the activity. A sequence for facilitating the detection or purification, such as the sequence containing a histidine residue or a continuous sequence thereof (poly-His), a c-Myc partial peptide (Myc-tag), a hemagglutinin partial peptide (HA-tag), a Flag partial peptide (Flag-tag), a glutathione-S-transferase (GST), a maltose-binding protein (MBP), etc., may be introduced to the amino terminal, the carboxy terminal, or an intermediate region of the amino acid sequence of at least one of the α, β, and γ subunits of the trimeric GTP-binding protein, and such proteins can be used.

The trimeric GTP-binding protein β subunit may be produced by the genetic engineering procedure using such as an animal cell, an insect cell, or a bacterial cell (e.g. an *Escherichia coli* cell), such that a corresponding gene is incorporated into a vector containing an appropriate promoter, the vector is introduced to a cell, and the cell is cultivated. Alternatively, an cell-free protein expression system containing an *Escherichia coli* extract, a wheat germ extract, etc. may be used. In the invention, the term "trimeric GTP-binding protein β subunit" includes products prepared by modifying the said protein such as botinylation, labeling with a fluorescent substance (such as a fluorescein), an Eu chelate, a chromophore, a luminophore, an enzyme, or a radioisotope (such as $^{125}$I or tritium); or binding of a compound having a hydroxysuccinimide residue, a vinylpyridine residue, etc. for facilitating the binding to a solid phase (such as a container or a carrier). The modification may apply to the β subunit itself, and also any of α and γ subunit existing in multimer.

In the above step of (A), specifically, the compound represented by the general formula (I) (hereinafter referred to as "said compound") is brought into contact with the trimeric GTP-binding protein β subunit (hereinafter referred to as "said protein") in a liquid phase, or alternatively one or both of the said compound and protein is fixed to a solid phase (such as a container or a carrier) and then contacted. For example, the compound may be fixed to the solid phase by binding a biotin-containing compound to a solid phase obtained by immobilizing streptavidin, by binding an amino-containing compound to a solid phase having on a surface a group reactable with the amino group, such as a hydroxysuccinimide group, by binding a carboxyl-containing compound to a solid phase having a group reactable to the carboxyl group on a surface, such as a hydrazine group, or by binding a thiol-containing compound to a solid phase having a group reactable with the thiol group on a surface, such as a vinylpyridine group. The compound may be fixed to the solid phase by another generally known method. For example, the said protein may be fixed to the solid phase (such as the container or carrier) by attaching the said protein to a solid phase composed of a polystyrene resin or a glass using the electrostatic attractive force or the intermolecular force, by binding the said protein being biotinylated to a solid phase obtained by immobilizing streptavidin, by binding the said protein to a solid phase obtained by immobilizing an antibody against the trimeric GTP-binding protein β subunit or the α or γ subunit existing as the multimer, by binding the said protein to a solid phase obtained by immobilizing an antibody against an amino acid sequence added to the said protein (such as poly-His, Myc-tag, HA-tag, Flag-tag, GST, or MBP), by binding the said protein attached with poly-His to a solid phase having on the surface a metal chelate, by binding the said protein attached with GST to a solid phase having on the surface a glutathione, or by binding the said protein attached with MBP to a solid phase having on the surface a sugar such as maltose. The protein may be fixed to the solid phase (such as the container or carrier) by another generally known method.

The contacting step of the said compound with the said protein may be conducted by mixing a solution containing them or a fixed carrier in a vessel such as a tube or a multi-well plate, or by adding a solution containing the said protein or the said compound or a solution containing carrier fixed with the said protein or the said compound to a material fixed with the said protein or the said compound on a solid phase of a container to be used.

In the above step of (B), specifically, the test substance (or a mixture containing the test substance) is used when the said compound is contacted with the said protein like the step of (A). The test substance (or the mixture containing the test substance) may be added before, in, or after the step of (A).

In the above step of (C), specifically, the binding of the said compound contained in a liquid phase or fixed to a solid phase (such as a container or a carrier) with the said protein contained in the liquid phase or fixed to the solid phase is measured in the presence and absence of the test substance (or the mixture containing the test substance) respectively, and the change of the binding depending on the addition of the test substance is observed, to evaluate the inhibitory effect of the test substance (or the mixture containing the test substance) on the binding of the said compound to the said protein. The binding of the said compound to the said protein may be measured with or without separating them.

For example, the said compound and the said protein may be separated by a gel filtration method, a column method using an affinity resin, an ion exchange resin, etc., a centrifugation method, or a washing method. For example, the amount of the said compound bound to the said protein may be measured after separating the said protein from the liquid phase by the gel filtration method or the column method (an affinity resin, an ion exchange resin, etc.). In the case of fixing one of the said compound and protein to the solid phase (such as the container or carrier), the solid phase (such as the container or carrier) may be separated from a liquid phase by centrifugation, washing, distributive segregation, precipitation, etc. In this case, the binding amount may be obtained directly by measuring the amount of the said compound or protein bound to the separated solid phase (such as the container or carrier), or indirectly by measuring the amount of the said compound or protein remaining in the liquid phase. The said compound and the said protein in the liquid phase may be separated by an immunoprecipitation method using a protein or an antibody specifically reactable with one of the said compound and protein, as well as a gel filtration method, a column method using an affinity resin, an ion exchange resin, etc., a centrifugation method, or a washing method. The binding amount of the said compound and protein may be obtained directly by measuring the amount of the separated said compound or protein, or indirectly by measuring the amount of the said compound or protein contained in a fraction separated from fractions containing the bound compound and protein.

The amount of the said compound bound or contained in a solution may be measured using a compound labeled with biotin, a radioisotope, a fluorophore, a chromophore, a chemiluminescent moiety, or an enzyme such as the compound of (1) to (4). For example, the amount of the biotin-labeled compound may be measured by using a protein capable of binding to the biotin with high affinity such as avidin, streptavidin, or a variant protein thereof (hereinafter referred to as the avidins) such that avidins is labeled with the radioisotope, the fluorophore, the luminophore, or the enzyme, which can be easily detected, and bound to the biotin-labeled compound. The radioactive substance may be measured using a common radiation measuring apparatus such as a scintillation counter, a gamma counter, or a GM meter. The fluorophore, the chromophore, and the luminophore may be measured using a fluorescence measuring apparatus, an absorptiometer, and a luminescence measuring apparatus respectively. The amount of the enzyme-labeled compound can be easily measured using a compound that is converted by the enzyme to a chromogenic, fluorescent, or luminescent compound.

The amount of the said protein bound or contained in a solution may be measured as follows. For example, the said protein labeled with the biotin, the fluorescent substance (such as the fluorescein), the Eu chelate, the chromophore, the luminophore, the enzyme, or the radioisotope (such as $^{125}$I or tritium) may be measured in the same manner as above. The biotinylated said protein may be measured by an immunoprecipitation method, an Western blot method, a solid-phase enzyme immunoassay (an enzyme-linked immuno-sorbent assay: ELISA), or a sandwich assay such as a radioimmunoassay, by using a protein such as streptavidin; an antibody against the trimeric GTP-binding protein β subunit or the α or γ subunit in the multimer; an antibody against an amino acid sequence added to the said protein (such as poly-His, Myc-tag, HA-tag, Flag-tag, GST, or MBP); a molecule having a metal chelate against a poly-His-added said protein; a molecule having a glutathione against a GST-added said protein; a molecule having a sugar such as maltose against an MBP-added said protein; etc.

In the case of not separating the said compound and protein, specifically, a scintillation proximity assay (SPA) method, a fluorescence resonance energy transfer (FRET) method, or an AlphaScreen assay method can be used typically. In a SPA method, specifically the binding of the radio-isotope-labeled said compound to the said protein directly or indirectly bonded to a carrier or a container containing a scintillation molecule is measured using a measuring device such as a scintillation counter or a CCD camera. Imaging beads, Flashplate, or the like using the same principle can be included within the above. The FRET method includes a method comprising a fluorescent substance bound directly or indirectly to the said compound, a fluorescent substance directly or indirectly bound also to the said protein, and measuring the intensity of fluorescence thus generated by the resonance energy transfer caused between the fluorescent substances by the binding of the said compound to the said protein. A TR-FRET method using a chelate containing an ion of a lanthanium atom such as Eu, Sm, or Tb by time-resolved fluorometry is also included within the above. A typical AlphaScreen assay comprises binding the said compound and protein with directly or indirectly to different carriers separately, generating singlet oxygen from one carrier (one bead) by light irradiation, and measuring the luminescence obtained by a reaction of the singlet oxygen with the other carrier (the other bead) evaluate the spatial proximity of the carriers caused by the bindings of the said compound and protein.

In a more specific example, a trimeric GTP-binding protein βγ subunit dimer having the Myc-tag sequence in the γ subunit is contacted with and bound to a tritium-labeled Compound 1 using a 96-multi-well plate in the presence/absence of a test substance in the presence of an anti-Myc antibody (a mouse-derived monoclonal antibody) and an anti-mouse immunoglobulin antibody-fixed SPA bead, and after a certain period, the binding amount of the trimeric GTP-binding protein βγ subunit dimer and the tritium-labeled Compound 1 is measured using a scintillation counter, and the counted values obtained in the presence/absence of the test substance are compared, whereby the inhibitory effect of the test substance against the binding of the said compound to the said protein is measured.

In the invention, the method for measuring the inhibitory activity of the test substance against the binding of the said compound to the said protein is not particularly limited. For example, the inhibitory activity may be measured by the following method.

(5a) A method according to (5), comprising the steps of: fixing the said protein to the solid phase; contacting the said compound with the said protein in the presence or absence of the test substance; and measuring the amount of the said compound bonded to the solid phase to measure the inhibitory activity of the test substance against the binding of the said compound to the said protein.

(5b) A method according to (5), comprising the steps of: fixing the said compound to the solid phase; contacting the said protein with the said compound in the presence or absence of the test substance; and measuring the amount of the said protein bonded to the solid phase to measure the inhibitory activity of the test substance against the binding of the said compound to the said protein.

(5c) A method according to (5), comprising the steps of: contacting the said compound with the said protein in the presence or absence of the test substance; and measuring the binding amount of the said compound and protein to measure the inhibitory activity of the test substance against the binding of the said compound to the said protein.

In the methods of (5a) to (5c), for example, the binding amount obtained by the contact in the presence of the test substance may be compared with the binding amount obtained by the contact in the absence of the test substance, to measure the inhibitory activity of the test substance against the binding of the said compound to the said protein.

The term "screening of a hypoglycemic compound" means that a compound having a desired activity is obtained and identified by predetermined operation using a compound having a known or unknown structure or a mixture thereof, whereby a compound having a hypoglycemic effect is obtained and identified.

In the method of (5a), specifically, fixing the said protein to the solid phase such as the container or carrier, adding the test substance (or the mixture containing the test substance) and the said compound thereto simultaneously or sequentially, and measuring the amount of the said compound bound to the solid phase are included. For example, a complex of the trimeric GTP-binding protein β subunit and a trimeric GTP-binding protein γ subunit added with the Myc-tag sequence is used as the said protein and fixed to an SPA bead by an anti-Myc-tag antibody and an anti-mouse antibody, a tritium-labeled Compound 1 is used as the said compound, and the binding thereof is measured in the presence/absence of the test substance to examine the inhibitory activity of the test substance against the binding.

In the method of (5b), specifically, fixing the said compound to the solid phase such as the container or carrier, adding the test substance (or the mixture containing the test substance) and the said protein thereto simultaneously or sequentially, and measuring the amount of the said protein bound to the solid phase are included. For example, Compound 2 having an amino group at the end of the linker moiety is used as the said compound and fixed to a carrier having a hydroxysuccinimide group by a chemical reaction, an extract of a cell membrane containing the trimeric GTP-binding protein β subunit is used as the said protein, the said protein is bound to a column of the carrier having the said compound, a solution containing the test substance is introduced into the column, and the amount of thus eluted said protein is measured indirectly by a Western blot method, to examine the amount of the said protein bound.

In the method of (5c), specifically, adding the test substance (or the mixture containing the test substance) and the said compound to the said protein simultaneously or sequentially, and measuring the binding amount of the said compound to the said protein are included. For example, an extraction liquid of an animal cell in which the β and γ subunits of the trimeric GTP-binding protein are simultaneously expressed, an extract of an insect cell in which the α subunit (containing a poly-His sequence), the β subunit, and the γ subunit (containing an Myc-tag sequence) of the trimeric GTP-binding protein are simultaneously expressed, or a purified βγ dimer is used as the said protein, a tritium-labeled Compound 1 is used as the said compound, the said protein is bound to the said compound in the presence/absence of the test substance, a high-molecular fraction containing the said protein is collected by gel filtration, and the radioactivity of the fraction is measured to examine the amount of the said compound, whereby the inhibitory activity of the test substance against the binding of the said protein to the said compound is measured.

It should be noted that the screening methods are considered to be illustrative and not restrictive.

In the invention, there is further provided (6) a method according to any one of (1) to (4), wherein the method for screening the hypoglycemic compound by measuring the inhibitory activity of the test substance against the binding of the compound represented by the general formula (I) or the pharmaceutically acceptable salt thereof (the said compound) to the trimeric GTP-binding protein β subunit uses a cell, a tissue, or an extract thereof containing the trimeric GTP-binding protein β subunit.

The cell or tissue substantially containing the trimeric GTP-binding protein β subunit may be derived from any organism and may be any cell or tissue. The cell or tissue may be naturally occurring one, and may be an animal cell, an insect cell, or a bacterium in which the trimeric GTP-binding protein β subunit is expressed (or coexpressed together with a protein capable of binding thereto) by a genetic engineering procedure. For example, the extract may be a cytosol or a cell fraction such as a cell membrane, a microsome, a nucleus, or a Golgi body, and the extracts solution may be a solution prepared from the cell per se or the extract above by a procedure such as homogenization, sonication, surfactant treatment, or buffer extraction.

In the invention, there is further provided (7) a method for screening a hypoglycemic compound, comprising the steps of:

(A) fixing the trimeric GTP-binding protein β subunit to a solid phase;

(B) contacting a test substance with the trimeric GTP-binding protein β subunit; and (C) eluting a compound bound to the solid phase by using a solution containing the compound represented by the general formula (I) (such as a compound of Examples 1 to 10), an acid, a base, a denaturant, etc.

The steps of (A) and (B) are as described in the method of (5). In the step of (C), a hypoglycemic compound bound to the said protein fixed to the solid phase such as the container or carrier can be obtained by adding the compound capable of substantially binding to the said protein (selected from the compounds represented by the general formula (I)) competitively, or by adding the acid, base, denaturant, etc. to lower the affinity of the hypoglycemic compound against the said protein.

A potent hypoglycemic compound can be obtained by the method of (1) to (7) using the above synthesized compound or a preparation containing a mixture of the compound. Thus, by using the method of (1) to (7), a hypoglycemic compound with high activity can be obtained, and a hypoglycemic compound with higher activity can be extracted from a mixture of compounds having different activities. A more effective hypoglycemic compound can be obtained using this method.

The more effective hypoglycemic compound obtained by the screening method above can be used as a material for a medicament without modifications whether it is obtained in the state of a single substance or a mixture. When only a small amount of the compound is obtained by the screening method, the compound may be prepared in a large amount by identifying the structure of the compound and by synthesizing based on the identified structural formula.

[5] Therapeutic Agent of the Invention

As described in the summary of the invention, the inventors has found that, in the compound capable of binding to the trimeric GTP-binding protein β subunit, there is a good correlation between the binding activity and the activity for enhancing the Akt phosphorylation and the glucose uptake in a cell. It is a radically new knowledge previously unknown that the compound identified by the above method, capable of binding to the trimeric GTP-binding protein β subunit, acts to enhance the glucose uptake. Accordingly, in the invention, there is provided (8) an antidiabetic agent comprising, as an active ingredient, the hypoglycemic compound capable of binding to the trimeric GTP-binding protein β subunit.

As described above, the inventors has found that the compound capable of binding to the trimeric GTP-binding protein β subunit can enhance the enzymatic activity of phosphoinositide 3-kinase and thereby can act to enhance the Akt phosphorylation and the glucose uptake in the cell. Such compound is a hypoglycemic substance useful as an antidiabetic agent. Accordingly, in the invention, there is provided (9) an antidiabetic agent comprising, as an active ingredient, a hypoglycemic compound having a main effect of binding to the trimeric GTP-binding protein β subunit, and enhancing the enzymatic activity of phosphoinositide 3-kinase. The phosphoinositide 3-kinase to be enhanced may be of any subtype and may contain a plurality of subtypes. It is preferred that the phosphoinositide 3-kinase is of the subtype β, and it is more preferred that the hypoglycemic compound have an effect to phosphoinositide 3-kinase β, and have no effect to γ.

The inventors has found based on Examples of the invention that a compound which binds to the same site where the compound represented by the general formula (I) (such as the compounds of Examples 1 to 10) binds to the trimeric GTP-binding protein β subunit, which was used as the "probe molecular" herein, can enhance the Akt phosphorylation and the glucose uptake. This is a new knowledge obtained in the invention. Furthermore, it is radically new knowledge that, when a low-molecular weight compound is bound to the GTP-binding protein β subunit and undergo a physiological reaction, the Akt phosphorylation and the glucose uptake may be enhanced thereby. Accordingly, in the invention, there is provided (10) an antidiabetic agent comprising, as an active ingredient, a compound capable of binding to the same site of the trimeric GTP-binding protein β subunit bound by the compound represented by the general formula (I) (such as Compound 1 to 7).

The compound that binds to the same site on the said protein that the compound represented by the general formula (I) substantially binds to is defined by the substantially competitive binding of both compounds to the said protein. For example, this property can be easily tested by the methods of Examples 16 and 22 described in the invention.

The antidiabetic agent of the invention is based on the new knowledge on a novel mechanism (a pharmacological action) of diabetes treatment. Thus, the antidiabetic agent of the invention includes wide range of compounds having this pharmacological action, and does not include compounds known to have a diabetes therapeutic effect (such as the compounds of Examples 3, 5, and 6).

The antidiabetic agent of the invention preferably has an $EC_{50}$ value of 10 µM or less measured by a glucose uptake activity measurement method described in Example 11. The $EC_{50}$ value is more preferably 0.1 µM or less, particularly preferably 0.01 µM or less.

For example, the therapeutic agent of the invention can be used for the prevention and/or the treatment of diabetes, diabetic peripheral nerve disorder, diabetic nephropathy, diabetic retinopathy, diabetic macroangiopathy, abnormal glucose tolerance, or obesity. In this case, the therapeutic agent may be administered orally, intravenously, or transdermally. The dosage of the active ingredient compound is generally 0.001 to 1000 mg/kg/day though it may be selected depending on the symptom and age of patient and the administration route.

The therapeutic agent of the invention may be formulated by a common method. Examples of the formulation include injections, tablets, granules, subtle granules, powders, capsules, creams, and suppositories. Examples of carriers for the formulation include lactose, glucose, D-mannitol, starch, crystalline cellulose, calcium carbonate, kaolin, starch, gelatin, hydroxypropylcellulose, hydroxypropylmethylcellulose, polyvinylpyrrolidone, ethanol, carboxymethylcellulose, carboxymethylcellulose calcium salts, magnesium stearate, talc, acetylcellulose, sucrose, titanium oxide, benzoic acid, p-oxybenzoate esters, sodium dehydroacetate, gum arabic, tragacanth, methylcellulose, egg yolk, surfactants, sucrose, simple syrups, citric acid, distilled water, ethanol, glycerin, propylene glycol, macrogol, sodium hydrogen phosphate, sodium dihydrogen phosphate, sodium phosphate, glucose, sodium chloride, phenol, thimerosal, p-oxybenzoate esters, and sodium hydrogen sulfite etc. The carrier is mixed with the compound of the invention depending on the dosage form.

The amount of the active ingredient of the invention in the formulation is not particularly limited and may be selected depending on the dosage form. The weight ratio of the active ingredient to the entire composition is generally 0.01 to 100% by weight, preferably 1 to 100% by weight.

[6] Screening Method According to Another Embodiment of the Invention

Various methods for measuring the concerted action of the trimeric GTP-binding protein β subunit and phosphoinositide 3-kinase have been widely known (Non-Patent Document 4 and Non-Patent Document 10: Kerchner et al., *Journal of Biological Chemistry*, 279, 44554, (2004)). In the invention, based on the result that the compound capable of binding to the trimeric GTP-binding protein β subunit, thereby enhancing the enzymatic activity of phosphoinositide 3-kinase can act as the glucose uptake enhancer, the hypoglycemic compound can be screened by detecting a compound capable of enhancing the binding of the trimeric GTP-binding protein β subunit to phosphoinositide 3-kinase.

Phosphoinositide 3-kinase is a molecule comprising a heterodimer, and α, β, γ, and δ subtypes thereof having different enzymatically active subunits are known. As described above, it is known that the activities of the β and γ are increased in the presence of the trimeric GTP-binding protein β subunit (Non-Patent Document 4). As described in Examples, it is found that the active compound obtained by the method of (1) to (7) can further increase the activity of phosphoinositide 3-kinase under the presence of the trimeric GTP-binding protein β subunit. Furthermore, it is found that since the active compound obtained by the method of (1) to (7) enhances the Akt phosphorylation and glucose uptake activities, the hypoglycemic compound can be screened by detecting a compound capable of improving the effect of the trimeric GTP-binding protein β subunit on enhancing the enzymatic activity of phosphoinositide 3-kinase.

It is widely known that the Akt phosphorylation is caused by activating the phosphoinositide 3-kinase. Therefore, it is expected that the compound of the invention capable of further enhancing the phosphoinositide 3-kinase enzymatic activity-enhancing effect of the trimeric GTP-binding protein subunit shows the Akt phosphorylation and glucose uptake activities. The compound, which directly further enhances the phosphoinositide 3-kinase enzymatic activity-enhancing effect of the trimeric GTP-binding protein β subunit and further has the Akt phosphorylation and glucose uptake activities thereby, has not been known in the past. Thus, the invention demonstrates, for the first time, that the hypoglycemic compound can be effectively screened by detecting the compound capable of further enhancing the phosphoinositide 3-kinase enzymatic activity-enhancing effect of the trimeric GTP-binding protein β subunit.

Accordingly, in the invention, there is provided (11) a method for screening a hypoglycemic compound, characterized by detecting a compound capable of further enhancing the phosphoinositide 3-kinase enzymatic activity-enhancing effect of the trimeric GTP-binding protein β subunit.

For example, the compound capable of further enhancing the phosphoinositide 3-kinase enzymatic activity-enhancing effect of the trimeric GTP-binding protein β subunit can be practically detected by a method reported by Maier et al. (Non-Patent Document 4) or Kerchner et al. (Non-Patent Document 10) as described in Examples. In this method, phosphatidylinositol-[4,5]-bisphosphate and a radioisotope-labeled ATP are used as substrates, and the amount of phosphatidylinositol-[3,4,5]-trisphosphate generated by the reaction therebetween is measured. In general, phosphatidylinositol may be used as the substrate instead of phosphatidylinositol-[4,5]-bisphosphate to measure phosphatidylinositol-[3]-phosphate generated (Non-Patent Document 11: Leopoldt et al., *Journal of Biological Chemistry*, 273, 7024, (1998)). In the invention, the detection method is not limited to the above example methods, and the compound may be detected by any method substantially capable of measuring a product generated by an enzyme reaction of phosphoinositide 3-kinase. Alternatively, the phosphoinositide 3-kinase activity may be evaluated by using an antibody against the phosphatidylinositol-[3,4,5]-trisphosphate (Non-Patent Document 12: Dowler et al., *Science STKE*, L6, (2002)) or a protein specifically binding to the trisphosphate (Non-Patent Document 13: Cho et al., *Annual Reviews of Biophysical Biomolecular Structure*, 34, 119, (2005)) instead of the radioisotope-labeled ATP and by measuring the amount of the generated phosphatidylinositol-[3,4,5]-trisphosphate. Furthermore, the phosphoinositide 3-kinase activity may be evaluated by measuring ADP generated by the reaction, etc.

The phosphoinositide 3-kinase of the α, β, γ, or δ subtype, preferably of the β or γ subtype that is enzymatically activated by the trimeric GTP-binding protein β subunit, particularly preferably of the β subtype can be used. The phosphoinositide 3-kinase may be extracted from a cell or a tissue, and may be produced as a recombinant. The phosphoinositide 3-kinase may be used in the purified, partially purified, or unpurified state as long as it can show the desired enzymatic activity substantially. The phosphoinositide 3-kinase α, β, and δ subtypes are present in the state of a heterodimer containing regulatory subunit named as a p85 or p55 and an enzymatically active subunit named as p110 α, β, and δ. The phosphoinositide 3-kinase is desirably used in the state of the heterodimer, but the monomeric enzymatically active subunit can be used. The phosphoinositide 3-kinase γ subtype is present in the state of a heterodimer containing a p101 regulation subunit and a p110 γ enzymatically active subunit, and may be used in the same manner as the above. In the invention, an artificial amino acid sequence for facilitating the purification or detection may be introduced to the amino terminal, the carboxy terminal, or an intermediate region of each subunit, as long as the resultant subunit can substantially exhibit the enzymatic activity.

Bonacci et al. (Non-Patent Document 6) have reported that N-deacetylcolchicine (referred to as M201 in the document) enhances the enzymatic activity of phosphoinositide 3-kinase γ heterodimer on phosphatidylinositol substrate in the presence of the trimeric GTP-binding protein β subunit. However, as described in Example 21, the N-deacetylcolchicine cannot enhance the enzymatic activity of phosphoinositide 3-kinase γ heterodimer on the phosphatidylinositol-[4,5]-bisphosphate substrate in the presence of the trimeric GTP-binding protein β subunit. In addition, Bonacci et al. have not reported on the Akt phosphorylation and glucose uptake activities, etc. of the N-deacetylcolchicine. In contrast, the glucose uptake enhancer of this description significantly enhances the phosphoinositide 3-kinase enzymatic activity on the phosphatidylinositol-[4,5]-bisphosphate substrate in the presence of the trimeric GTP-binding protein β subunit. Thus, the invention demonstrates, for the first time, that a substance can activate phosphoinositide 3-kinase (more preferably phosphoinositide 3-kinase β) in the presence of the trimeric GTP-binding protein β subunit, and a compound obtained by screening based on such an activity can enhance the Akt phosphorylation and glucose uptake. The invention discloses the contents and techniques thereof. In the screening method, phosphatidylinositol-[4,5]-bisphosphate is more preferably used as a substrate, and a method for measuring a product substantially generated by the enzymatic reaction of phosphoinositide 3-kinase can be used as described above.

In the invention, there is provided (12) a method for screening a hypoglycemic compound, characterized by detecting a compound capable of enhancing the binding of phosphoinositide 3-kinase to the trimeric GTP-binding protein β subunit.

As described in Example 25, it has been found that the compound identified to be active by the method of (1) to (7) can enhance the binding of phosphoinositide 3-kinase to the trimeric GTP-binding protein β subunit. Thus, the hypoglycemic compound can be screened by detecting a compound capable of enhancing the binding of phosphoinositide 3-kinase to the trimeric GTP-binding protein β subunit.

As described in Examples, the binding of phosphoinositide 3-kinase to the trimeric GTP-binding protein β subunit can be evaluated such that the reacted proteins are subjected to immunoprecipitation using an antibody against one of the proteins, and the amount of the other protein contained in the precipitate is measured by a Western blot method using an antibody against the other protein. This method is considered to be illustrative, and for example the binding may be measured by a sandwich assay using antibodies against both the proteins. Specific examples of the sandwich assays include solid-phase enzyme immunoassays (enzyme-linked immuno-sorbent assays: ELISA) and radioimmunoassay. When each protein is labeled with a radioisotope or biotin, the binding of the proteins may be measured without using antibodies. As described in [4], specific examples of such methods include scintillation proximity assay (SPA) methods, fluorescence resonance energy transfer (FRET) methods such as TR-FRET methods, and AlphaScreen assay methods.

The phosphoinositide 3-kinase used in the above screening method may be of any subtype and may contain a plurality of subtypes. It is preferred that the phosphoinositide 3-kinase is of the subtype β, and it is more preferred that the screened compound have an effect on the phosphoinositide 3-kinase β and have no effect on γ. Thus, in the invention, there is provided (13) a method according to (11) or (12), characterized in that the phosphoinositide 3-kinase is of the subtype β.

The invention provides the screening of the hypoglycemic compound that can be used as an active ingredient of an antidiabetic agent. The screening may be carried out using (i) the screening method of (1) to (7) based on the binding of the trimeric GTP-binding protein β subunit, preferably the inhibitory activity against the binding of the compound represented by the general formula (I) to the trimeric GTP-binding protein β subunit, (ii) the screening method of (11) based on the phosphoinositide 3-kinase enzymatic activity-enhancing effect of the trimeric GTP-binding protein β subunit and/or the screening method of (12) based on the activity for enhancing the binding thereof, or a combination thereof.

The compound having the desired activity and function, obtained by the above screening method, may be further evaluated with respect to (iii) the activity for enhancing glucose uptake of a cell/tissue, which can be measured in terms of the glucose uptake activity, or (iv) the hypoglycemic effect obtained when administered to an animal, etc. Thus, the screening is completed. Examples of the cells/tissues described in (iii), which can be measured in terms of the glucose uptake activity, include fat tissues, adipocytes, preadipocytes, muscle tissues, myocytes, premyocytes, liver tissues, hepatocytes, and prehepatocytes, as well as 3T3-L1 cells, differentiated 3T3-L1 cells, L6 cells, and Glut4 expressing animal cells. The cell/tissue may be any one as long as the glucose uptake activity thereof can be substantially detected. The animal described in (iv) may be a healthy animal or a diabetic model animal, and typical examples thereof include mice, rats, guinea pigs, hamsters, rabbits, dogs, and monkeys. The animal may be of any useful type, and the hypoglycemic effect on human (diabetic or nondiabetic patient) may be evaluated.

Since the knowledges of (i) and (ii) have not been known in the past, conventional known methods for screening a hypoglycemic compound having the glucose uptake activity contain only the evaluation of (iii) and (iv). The evaluation of (iii) using the cell or tissue and the evaluation of (iv) using the animal are unsuitable for the screening because of a burden for preparation work, a large difference between the preparations, etc. Furthermore, the conventional methods has a high risk of missing a compound having a desirable novel scaffold because it is difficult to evaluate a compound having a low membrane permeability or a physiological affect or toxicity on a cell. In contrast, the methods of (i) and (ii) can be carried out using the same material without using cells, and thus is remarkably suitable for the screening.

EXAMPLES

The present invention will be described more specifically below with reference to Examples without intention of restricting the scope of the invention.

Example 1

Compound 1

[Chemical Formula 4]

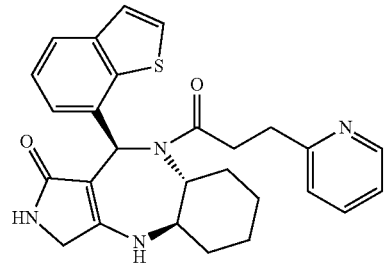

The steps 1 and 2 were carried out using a method described in WO 02/44180.

Step 1

Synthesis of pyrrolidine-2,4-dione (tetramic acid)

Triethylamine (72 g, 0.713 mmol) was added to a dichloromethane solution (800 ml) of glycine ethyl ester hydrochloride (54.68 g, 0.392 mol), and cooled to 0° C. To this was added a dichloromethane solution (100 ml) of methyl 3-chloro-3-oxobutanoate (48.5 g, 0.355 mmol) dropwisely over 30 minutes, and the resultant was stirred at room temperature for 4 hours. After the completion of the reaction, water (1000 ml) was added thereto, and the dichloromethane layer was separated, washed with a brine, and dried over anhydrous sodium sulfate. The solvent was distilled off, and to the residue were added methanol (600 ml) and activated carbon (10 g). The mixture was stirred for a while and then celite-filtered, and the solvent was removed to obtain a yellow oil of methyl 3-ethoxycarbonylmethylamino-3-oxobutanoate (66.9 g, 93%).

$^1$H-NMR (300 MHz, DMSO-d6) δ=1.17 (t, J=7.2 Hz, 3H), 3.30 (s, 2H), 3.60 (s, 3H), 3.83 (d, J=5.7 Hz, 2H), 4.07 (q, J=7.2 Hz, 2H), 8.50 (broad t, 1H).

Methanol (40 ml) and toluene (400 ml) were added to the obtained methyl 3-ethoxycarbonylmethylamino-3-oxobutanoate (66.9 g, 0.33 mol), a 28%-sodium methoxide/methanol solution (70 g, 0.363 mol) was further added thereto dropwisely while vigorously stirring, and the mixture was heated at 65° C. for 1 hour. After the completion of the reaction, the mixture was neutralized with 2N hydrochloric acid (185 ml, 0.37 mol), and the resultant solid was isolated by filtration and dried to obtain a beige powder of 3-methoxycarbonylpyrrolidine-2,4-dione (39.5 g, 0.25 mol).

$^1$H-NMR (300 MHz, DMSO-d6) δ=3.62 (s, 3H), 3.82 (s, 2H), 7.50 (broad s, 1H).

1,4-Dioxane (2400 ml) and water (240 ml) were added to the obtained 3-methoxycarbonylpyrrolidine-2,4-dione (39.5 g, 0.25 mol), and the mixture was refluxed under heating for 30 minutes. After the completion of the reaction, the solvent was distilled off to obtain a pale yellow solid of pyrrolidine-2,4-dione (tetramic acid) (24.4 g, 100%).

$^1$H-NMR (300 MHz, DMSO-d6) ketone form δ=2.93 (s, 2H), 3.77 (s, 2H), 8.23 (s, 1H), enol form δ=3.74 (s, 2H), 4.75 (s, 1H), 7.07 (s, 1H), ketone:enol=3:2.

Step 2

Synthesis of 4-((2-aminophenyl)amino)-3-pyrroline-2-one

A methanol solution containing the pyrrolidine-2,4-dione (6.93 g, 70 mmol) obtained in the step 1 and 1,2-phenylenediamine (7.88 g, 70 mmol) was stirred at 6° C. for 1 hour. The reaction solution was cooled, and the precipitated crystal was isolated by filtration, to obtain 4-((2-aminophenyl)amino)-3-pyrroline-2-one (11.6 g, 87%).

$^1$H-NMR (300 MHz, DMSO-d6) δ=3.94 (s, 2H), 4.56 (s, 1H), 4.91 (bs, 2H), 6.55 (dt, J=1.5, 7.5 Hz, 1H), 6.72 (dd, J=1.5, 7.8 Hz, 1H), 6.80 (s, 1H), 6.86 (dt, J=1.5, 7.5 Hz, 1H), 7.02 (dd, J=1.5, 7.8 Hz, 1H), 8.03 (s, 1H); ESI-MS (m/z) 190 (M+H)$^+$.

Step 3

4-((2-aminophenyl)amino)-3-pyrroline-2-one (504 mg, 2.58 mmol) obtained in the step 2 and benzothiophene-7-aldehyde (419 mg, 2.58 mmol) were dissolved in ethanol (26 ml). To the solution was added acetic acid (30 μl, 0.516 mmol), and the mixture was stirred at 60° C. for 18 hours. The solvent was removed under reduced pressure, and the residue was purified by a silica gel column chromatography (dichloromethane:methanol=91:9) to obtain the desired product (315 mg, 36.7%).

$^1$H-NMR (300 MHz, DMSO-d6) δ=0.76-0.95 (m, 1H), 1.00-1.23 (m, 3H), 1.41-1.62 (m, 3H), 1.85-1.97 (m, 1H), 2.00-2.12 (m, 1H), 2.80-2.91 (m, 1H), 3.80 (d, J=16.4 Hz, 1H), 3.95 (d, J=16.4 Hz, 1H), 5.06 (s, 1H), 6.44 (s, 1H), 6.82 (s, 1H), 6.96 (d, J=7.0 Hz, 1H), 7.29 (dd, J=7.0, 7.9 Hz, 1H), 7.45 (d, J=5.3 Hz, 1H), 7.72 (d, J=5.3 Hz, 1H), 7.76 (d, J=7.9 Hz, 1H); ESI-MS (m/z) 340 (M+H)$^+$.

Step 4

The compound (315 mg, 0.927 mmol) obtained in the step 3 and (2E)-3-(pyridin-2-yl)-acrylic acid (414 mg, 2.78 mmol) were dissolved in dimethylformamide (10 ml). To the solution was added 1-ethyl-(3-diethylaminopropyl)-carbodiimide hydrochloride (hereinafter referred to as EDCl, 524 mg, 2.78 mmol), and the mixture was stirred at room temperature for 18 hours. During the stirring, the same amount of the reactant was appropriately added until the starting material disappeared. The solvent was removed under reduced pressure, and ethyl acetate was added to the residue. The resultant mixture was washed with water, a saturated aqueous sodium hydrogen carbonate solution, and a saturated brine, and dried over anhydrous sodium sulfate. The solvent was removed under reduced pressure, and the residue was purified by a silica gel column chromatography (dichloromethane:methanol=20:1) to obtain the desired product (157 mg, 36.0%).

$^1$H-NMR (300 MHz, CDCl$_3$) δ=0.564-0.765 (m, 1H), 1.02-1.38 (m, 3H), 1.39-1.58 (m, 2H), 1.68-1.98 (m, 2H), 2.51-2.74 (m, 1H), 2.95-3.13 (m, 1H), 3.90 (d, J=15.8 Hz, 1H), 3.99 (d, J=15.8 Hz, 1H), 4.37-4.54 (m, 2H), 5.30 (s, 1H), 5.69 (s, 1H), 6.52 (s, 1H), 7.16-7.23 (m, 1H), 7.32-7.51 (m, 3H), 7.60-7.75 (m, 2H), 7.79 (d, J=7.9 Hz, 1H), 7.99 (d, J=15.2 Hz, 1H), 8.54-8.71 (m, 1H); ESI-MS (m/z) 471 (M+H)$^+$.

Step 5

The compound obtained in the step 4 (145 mg, 0.304 mmol) was dissolved in methanol (3.0 ml). To the solution were added sodium borohydride (23.0 mg, 0.608 mmol) and nickel chloride hexahydrate (14.5 mg, 0.061 mmol) successively, and the mixture was stirred at room temperature for 3 hours. The reagent was further added until the starting material disappeared. To the reaction solution was added a saturated aqueous ammonium chloride solution, and the organic phase was extracted with ethyl acetate, washed with saturated brine, and dried over anhydrous sodium sulfate. The solvent was evaporated under reduced pressure to obtain a compound of Example 1 (135 mg, 94.0%).

$^1$H-NMR (300 MHz, DMSO-d6) δ=0.35-3.10 (m, 13H), 3.81 (d, J=16.5 Hz, 1H), 3.91 (d, J=16.5 Hz, 1H), 3.90-4.05 (m, 1H), 5.90 (s, 1H), 6.81 (s, 1H), 6.84 (s, 1H), 7.00-7.90 (m, 8H), 8.45-8.50 (m, 1H); ESI-MS (m/z) 473 (M+H)$^+$.

Furthermore, a tritium ($^3$H)-labeled Compound 1 was synthesized in the same reaction manner as above except for using $^3$H-sodium borohydride instead of sodium borohydride in the step 5.

Example 2

Compound 2

[Chemical Formula 5]

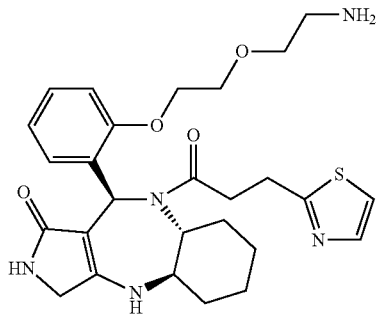

Step 1

A compound was synthesized in the same manner as the step 3 of Example 1 except for using 2-(2-ethoxymethyl)-benzaldehyde instead of benzothiophene-7-aldehyde.

$^1$H-NMR (300 MHz, DMSO-d6) δ=0.83-1.33 (m, 7H), 1.44-1.69 (m, 2H), 1.75-1.97 (m, 2H), 2.08-2.23 (m, 1H), 2.77-2.92 (m, 1H), 3.84 (d, J=16.4 Hz, 1H), 3.69 (q, J=7.3 Hz, 2H), 3.71 (d, J=16.4 Hz, 1H), 5.06 (s, 1H), 5.32 (s, 2H), 6.31 (s, 1H), 6.68 (s, 1H), 6.78-6.91 (m, 2H), 6.97-7.21 (m, 2H); ESI-MS (m/z) 358 (M+H)$^+$.

Step 2

The compound obtained in the step 1 (699 mg, 1.96 mmol) and (2E)-3-(1,3-thiazol-2-yl)-acrylic acid (1.22 g, 7.83 mmol) were dissolved in dimethylformamide (10 ml). To the solution was added EDCl (1.50 g, 7.83 mmol), and the mixture was stirred at room temperature for 2 and half days. The solvent was removed under reduced pressure, and to the residue was added ethyl acetate. The mixture was washed with water, a saturated aqueous sodium hydrogen carbonate solution, and a saturated brine successively, dried over anhydrous sodium sulfate, purified by a silica gel column chromatography (dichloromethane:methanol=20:1), to obtain the desired product (512 mg, 53%).

ESI-MS (m/z) 495 (M+H)$^+$.

Step 3

The compound obtained in the step 2 (512 mg, 1.04 mmol) was dissolved in methanol (10 ml). To the solution were added nickel chloride hexahydrate (49.2 mg, 0.207 mmol) and sodium borohydride (78.5 mg, 2.07 mmol) successively. The mixture was stirred at room temperature for 1 hour, a saturated aqueous ammonium chloride solution was added thereto, and the organic layer was extracted with ethyl acetate. The organic layer was washed with a saturated brine and dried over anhydrous sodium sulfate. The solvent was removed under reduced pressure to obtain the desired product (511 mg, 99.4%).

$^1$H-NMR (300 MHz, DMSO-d6) δ=0.53-0.76 (m, 1H), 0.87-1.33 (m, 8H), 1.37-1.61 (m, 2H), 1.92-2.10 (m, 1H), 2.67-2.96 (m, 2H), 3.14-3.28 (m, 2H), 3.48-3.65 (m, 2H), 3.76 (d, J=16 Hz, 1H), 3.84 (d, J=16 Hz, 1H), 3.95-4.09 (m, 1H), 5.18-5.32 (m, 2H), 5.86 (s, 1H), 6.70 (s, 1H), 6.75 (s, 1H), 6.94 (t, J=7.3 Hz, 1H), 7.00-7.13 (m, 2H), 7.23-7.32 (m, 1H), 7.54 (d, J=3.2 Hz, 1H), 7.68 (d, J=3.2 Hz, 1H); ESI-MS (m/z) 497 (M+H)$^+$.

The compound obtained in the step 3 (510 mg, 1.03 mmol) was dissolved in methanol (10 ml). To the solution was added concentrated hydrochloric acid (0.1 ml), and the mixture was stirred at 55° C. for 14 and half hours. The reaction solution was neutralized with 1N sodium hydroxide (1.1 ml). The organic layer was extracted with ethyl acetate, washed with a saturated brine, and dried over anhydrous sodium sulfate. The solvent was removed under reduced pressure to obtain the desired product (367 mg, 81.4%).

$^1$H-NMR (300 MHz, DMSO-d6) δ=0.53-0.75 (m, 1H), 0.90-1.21 (m, 3H), 1.39-1.58 (m, 2H), 1.91-2.06 (m, 1H), 2.42-2.60 (m, 1H), 2.69-2.86 (m, 1H), 2.87-3.00 (m, 1H), 3.14-3.27 (m, 2H), 3.76 (d, J=16 Hz, 1H), 3.83 (d, J=16 Hz, 1H), 3.91-4.08 (m, 2H), 5.82 (s, 1H), 6.65 (s, 1H), 6.70 (s, 1H), 6.74 (dd, J=7.3, 7.6 Hz, 1H), 6.83 (d, J=7.3 Hz, 1H), 6.94 (d, J=7.6 Hz, 1H), 7.11 (dd, J=7.3, 7.6 Hz, 1H), 7.54 (d, J=3.5 Hz, 1H), 7.67 (d, J=3.5 Hz, 1H), 9.72 (s, 1H); ESI-MS (m/z) 440 (M+H)$^+$.

Step 5

Bis-(2-bromoethyl)ether (2.04 ml, 16.2 mmol) and potassium succinimide (1.50 g, 8.10 mmol) were dissolved in dimethylformamide. The solution was heated to 80° C. and stirred for 19 hours. The solvent was removed under reduced pressure, and ethyl acetate was added to the residue. The organic layer was washed with water, a saturated aqueous sodium hydrogen carbonate solution, and a saturated brine, dried over anhydrous sodium sulfate, and purified by a silica gel column chromatography (hexane:ethyl acetate=5:1) to obtain a bromo compound (1.64 g, 68.0%).

ESI-MS (m/z) 299 (M+H)$^+$.

The compound obtained in the step 3 (380 mg, 0.865 mmol) and the bromo compound (309 mg, 1.04 mmol) were dissolved in dimethylformamide (5.0 ml). To the solution was added potassium carbonate (359 mg, 2.60 mmol), and the mixture was heated to 70° C. and stirred for 20 and half hours. The same amounts of the bromo compound and the potassium carbonate were added thereto again, and the resultant mixture was further stirred for 4 and half hours. To the reaction solution was added ethyl acetate, and the resultant solution was washed with water and a saturated brine and dried over anhydrous sodium sulfate. The solvent was removed under reduced pressure, and the residue was purified by a silica gel column chromatography (dichloromethane:methanol=95:5) to obtain the desired product (205 mg, 36.1%).

ESI-MS (m/z) 656 (M+H)$^+$.

Step 6

The compound obtained in the step 5 (205 mg, 0.313 mmol) and hydrazine monohydrate (150 μl, 3.13 mmol) were dissolved in ethanol. The solution was stirred at 70° C. for 1 hour and 20 minutes. The precipitated white solid was removed by filtration to obtain a compound of Example 2 (113 mg, 68.7%).

$^1$H-NMR (300 MHz, DMSO-d6) δ=0.52-0.73 (m, 1H), 0.88-1.19 (m, 4H), 1.37-1.56 (m, 3H), 1.90-2.05 (m, 1H), 2.56-2.67 (m, 4H), 2.68-2.93 (m, 2H), 3.10-3.30 (m, 5H), 3.59-3.73 (m, 2H), 3.76 (d, J=16 Hz, 1H), 3.84 (d, J=16 Hz, 1H), 3.92-4.06 (m, 1H), 4.06-4.22 (m, 2H), 5.84 (s, 1H), 6.68 (s, 1H), 6.73 (s, 1H), 6.87-6.95 (m, 1H), 6.98-7.07 (m, 2H), 7.23-7.34 (m, 1H), 7.54 (d, J=3.2 Hz, 1H), 7.67 (d, J=3.2 Hz, 1H); ESI-MS (m/z) 526 (M+H)+.

Example 3

Compound 3

[Chemical Formula 6]

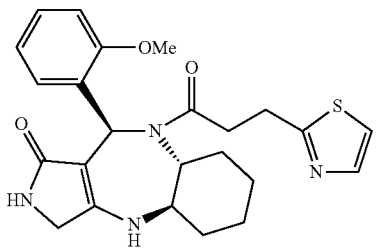

A compound was synthesized in the same manner as the steps 3 and 4 of Example 1 except for using 2-methoxybenzaldehyde instead of benzothiophene-7-aldehyde in the step 3 and using (2E)-3-(1,3-thiazol-2-yl)-acrylic acid instead of (2E)-3-(pyridin-2-yl)-acrylic acid in the step 4.

1H-NMR (300 MHz, DMSO-d6) δ=0.55-3.05 (m, 9H), 3.74 (d, J=16.5 Hz, 1H), 3.82 (d, J=16.5 Hz, 1H), 3.90-4.05 (m, 1H), 3.83 (s, 3H), 4.05-4.20 (m, 1H), 6.01 (s, 1H), 6.73 (s, 1H), 6.73 (s, 1H), 6.86-7.10 (m, 4H), 7.50 (d, J=15.3 Hz, 1H), 7.76 (d, J=15.6 Hz, 1H), 7.84 (d, J=3.0 Hz, 1H), 7.94 (d, J=3.0 Hz, 1H); ESI-MS (m/z) 449 (M−H)−.

Step 2

The compound obtained in the step 1 (38.3 mg, 0.085 mmol) was dissolved in ethanol (5.0 ml). To the solution was added 10% palladium/carbon (50% water content, 15 mg), and the mixture was stirred for 2 days under hydrogen atmosphere. The reaction solution was celite-filtered, and the solvent was evaporated under reduced pressure to obtain a compound of Example 3 (33 mg, 87%).

1H-NMR (300 MHz, DMSO-d6) δ=0.50-3.40 (m, 9H), 3.73 (s, 3H), 3.70-3.85 (m, 2H), 3.90-4.05 (m, 1H), 5.81 (s, 1H), 6.67 (s, 1H), 6.71 (s, 1H), 6.86-7.31 (m, 4H), 7.53 (d, J=3.3 Hz, 1H), 7.67 (d, J=3.3 Hz, 1H); ESI-MS (m/z) 453 (M+H)+, 451 (M−H)−.

Example 4

Compound 4

[Chemical Formula 7]

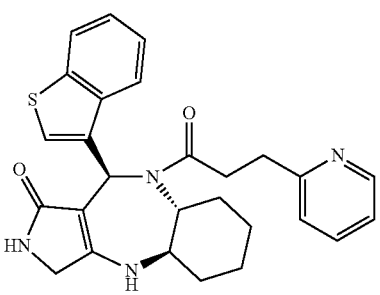

Step 1

A compound of Example 4 was synthesized in the same manner as Example 1 except for using benzothiophene-3-aldehyde instead of benzothiophene-7-aldehyde.

1H-NMR (300 MHz, DMSO-d6) δ=0.408-0.646 (m, 1H), 0.750-0.918 (m, 1H), 0.918-1.17 (m, 2H), 1.28-2.03 (m, 3H), 2.35-2.46 (m, 1H), 2.65-2.81 (m, 1H), 2.81-2.96 (m, 1H), 2.96-3.20 (m, 2H), 3.80 (d, J=16.4 Hz, 1H), 3.87 (d, J=16.4 Hz, 1H), 3.93-4.07 (m, 1H), 5.97 (s, 1H), 6.74 (s, 1H), 6.82 (s, 1H), 7.16-7.25 (m, 1H), 7.26-7.35 (m, 2H), 7.35-7.49 (m, 2H), 7.69 (dd, J=7.0, 7.0 Hz, 1H), 7.90 (d, J=6.5 Hz, 1H), 7.99 (d, J=6.5 Hz, 1H), 8.52 (s, 1H); ESI-MS (m/z) 473 (M+H)+.

Example 5

Compound 5

[Chemical Formula 8]

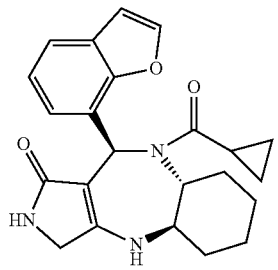

Step 1

A compound was synthesized in the same manner as the step 3 of Example 1 except for using benzofuran-7-aldehyde instead of benzothiophene-7-aldehyde.

1H-NMR (300 MHz, DMSO-d6) δ=0.75-1.20 (m, 4H), 1.35-1.55 (m, 2H), 1.75-1.90 (m, 1H), 2.10-2.25 (m, 2H), 2.75-2.90 (m, 1H), 3.72 (d, J=16.8 Hz, 1H), 3.84 (d, J=16.8 Hz, 1H), 5.30 (s, 1H), 6.36 (s, 1H), 6.72 (s, 1H), 6.80 (d, J=7.5 Hz, 1H), 6.93 (d, J=2.1 Hz, 1H), 7.09 (t, J=7.5 Hz, 1H), 7.48 (d, J=7.5 Hz, 1H), 7.98 (d, J=2.1 Hz, 1H); ESI-MS (m/z) 324 (M+H)+.

Step 2

The compound obtained in the step 1 (75 mg, 0.232 mmol) was dissolved in dimethylformamide (6 ml), to this were added cyclopropane carboxylic acid (370 ml, 4.65 mmol) and EDCl (712 mg, 3.71 mmol), and the mixture was stirred at room temperature for 3 days. The reaction solution was concentrated under reduced pressure, ethyl acetate was added to the residue, and the resultant solution was washed with a saturated sodium hydrogen carbonate solution and a saturated brine, and then dried over anhydrous magnesium sulfate. The solution was concentrated under reduced pressure, and the residue was purified by a reversed-phase HPLC to obtain a compound of Example 5 (61 mg, 67%).

¹H-NMR (300 MHz, DMSO-d6) δ=0.45-1.14 (m, 8H), 1.30-1.48 (m, 2H), 1.88-2.02 (m, 1H), 2.22-2.52 (m, 2H), 2.83-2.96 (m, 2H), 3.83 (d, J=16.8 Hz, 1H), 3.86 (d, J=16.8 Hz, 1H), 3.95-4.08 (m, 1H), 6.61 (s, 1H), 6.73 (s, 1H), 6.99 (d, J=2.1 Hz, 1H), 6.99 (d, J=7.5 Hz, 1H), 7.22 (t, J=7.5 Hz, 1H), 7.62 (d, J=7.5 Hz, 1H), 8.03 (d, J=2.1 Hz, 1H); ESI-MS (m/z) 392 (M+H)⁺.

Example 6

Compound 6

[Chemical Formula 9]

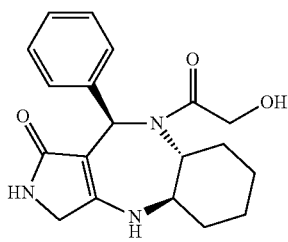

Step 1

A compound was synthesized in the same manner as the step 3 of Example 1 except for using benzaldehyde instead of benzothiophene-7-aldehyde.

¹H-NMR (300 MHz, DMSO-d6) δ=0.50-3.40 (m, 10H), 3.69 (d, J=16.0 Hz, 1H), 3.84 (d, J=16.0 Hz, 1H), 4.79 (s, 1H), 6.32 (s, 1H), 6.75 (s, 1H), 7.10-7.30 (m, 5H); 284 (M−H)⁺.

Step 2

The compound obtained in the step 1 (200 mg, 0.707 mmol) was dissolved in dichloromethane (50 ml), to this were added acetoxyacetic acid (500 mg, 4.24 mmol), triethylamine (209 µl, 1.41 mmol), and EDCl (543 mg, 2.83 mmol), and the mixture was stirred at room temperature for 4 hours. To the reaction solution was added 0.1N hydrochloric acid, and the organic layer was extracted with ethyl acetate, washed with a saturated brine, and dried over anhydrous sodium sulfate. The solvent was removed under reduced pressure, the residue was dissolved in methanol (10 ml), potassium carbonate (488 mg, 3.54 mmol) was added thereto, and the mixture was stirred at room temperature for 30 minutes. The mixture was celite-filtered to remove insoluble contents, water was added to the residue, and the organic layer was extracted with ethyl acetate, washed with a saturated brine, and dried over anhydrous sodium sulfate. The solvent was removed under reduced pressure, a solution of diethyl ether/dichloromethane (volume ratio 8/1) was added to the residue, and the precipitated crystal was isolated by filtration to obtain a compound of Example 6 (185 mg, 77%).

¹H-NMR (300 MHz, DMSO-d6) δ=0.50-2.79 (m, 9H), 3.75-4.05 (m, 4H), 4.42 (m, 1H), 4.72 (m, 1H), 5.54 (s, 1H), 6.74 (s, 1H), 6.80 (s, 1H), 7.22-7.37 (m, 5H); ESI-MS (m/z) 342 (M+H)⁺.

Example 7

Compound 7

[Chemical Formula 10]

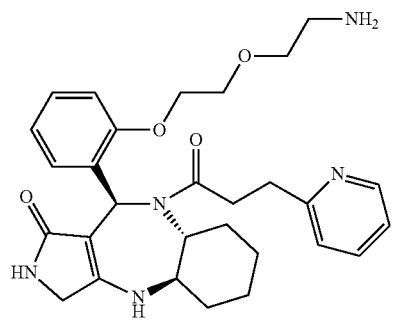

A compound of Example 7 was synthesized in the same manner as Example 2 except for using (2E)-3-(pyridin-2-yl)-acrylic acid instead of (2E)-3-(1,3-thiazol-2-yl)-acrylic acid.

¹H-NMR (300 MHz, DMSO-d6) δ=0.49-0.70 (m, 1H), 0.81-1.19 (m, 4H), 1.35-1.57 (m, 3H), 1.89-2.06 (m, 1H), 2.54-2.64 (m, 4H), 2.69-2.90 (m, 2H), 3.00-3.49 (m, 5H), 3.67-3.74 (m, 2H), 3.78 (d, J=16.8 Hz, 1H), 3.85 (d, J=16.8 Hz, 1H), 3.92-4.06 (m, 1H), 4.06-4.21 (m, 2H), 5.87 (s, 1H), 6.68 (s, 1H), 6.72 (m, 1H), 6.90 (dd, J=7.6, 7.6 Hz, 1H), 6.98-7.05 (m, 2H), 7.16-7.23 (m, 1H), 7.25 (s, 1H), 7.27 (s, 1H), 7.68 (ddd, J=1.8, 7.6, 7.6 Hz, 1H), 8.45-8.52 (m, 1H); ESI-MS (m/z) 520 (M+H)⁺.

Example 8

[Chemical Formula 11]

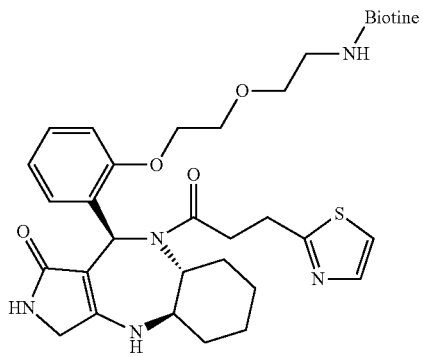

Step 1

The compound of Example 2 (20 mg, 0.0381 mmol) and biotin (37.2 mg, 0.152 mmol) were dissolved in dimethylformamide (1.0 ml). To the solution was added EDCl (29.1 mg, 0.152 mmol), and the mixture was stirred at room temperature for 21 hours. To the reaction solution was added ethyl acetate, and the mixture was washed with an aqueous sodium hydrogen carbonate solution and a brine, and stirred together with anhydrous sodium sulfate. The solvent was removed under reduced pressure, and the residue was purified by a silica gel column chromatography (dichloromethane:methanol=95:5) to obtain a compound of Example 8 (11.1 mg, 39.5%).

$^1$H-NMR (300 MHz, DMSO-d6) δ=0.51-0.76 (m, 1H), 0.79-1.18 (m, 4H), 1.21-1.40 (m, 4H), 1.42-1.80 (m, 10H), 1.90-2.16 (m, 2H), 2.57-2.69 (m, 2H), 2.69-2.95 (m, 3H), 2.98-3.15 (m, 2H), 3.62-3.71 (m, 2H), 3.79 (d, J=16.4 Hz, 1H), 3.86 (d, J=16.4 Hz, 1H), 3.95-4.06 (m, 1H), 4.06-4.24 (m, 3H), 4.24-4.43 (m, 1H), 5.86 (s, 1H), 6.36 (s, 1H), 6.42 (s, 1H), 6.72 (s, 1H), 6.77 (s, 1H), 6.88-6.97 (m, 1H), 6.99-7.09 (m, 2H), 7.23-7.38 (m, 1H), 7.47-7.60 (m, 1H), 7.64-7.74 (m, 1H); ESI-MS (m/z) 738.

Example 9

[Chemical Formula 12]

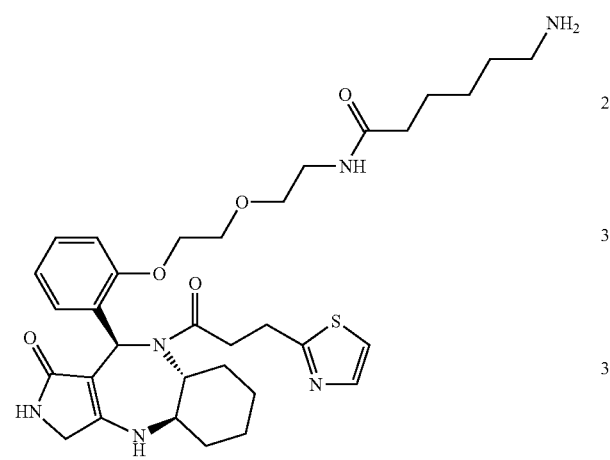

Step 1

The compound of Example 2 (20 mg, 0.0381 mmol) and N-tert-butyloxycarbonyl-6-aminocaproic acid (17.6 mg, 0.0761 mmol) were dissolved in dimethylformamide (1.0 ml). To the solution was added EDCl (14.6 mg, 0.0761 mmol), and the mixture was stirred at room temperature for 17 hours. To the reaction solution was added ethyl acetate, and the mixture was washed with an aqueous sodium hydrogen carbonate solution and a saturated brine, and dried over anhydrous sodium sulfate. The solvent was removed under reduced pressure, the residue was dissolved in trifluoroacetic acid (0.3 ml) and dichloromethane (0.1 ml), and the solution was stirred at room temperature for 30 minutes. To the reaction solution was added an aqueous sodium hydrogen carbonate solution, and the organic layer was extracted with dichloromethane, washed with a saturated brine, and dried over anhydrous sodium sulfate. The solvent was removed under reduced pressure to obtain a compound of Example 9 (19.8 mg, 81.5% for 2 steps).

$^1$H-NMR (300 MHz, DMSO-d6) δ=0.49-0.72 (m, 1H), 0.89-1.14 (m, 3H), 1.14-1.38 (m, 4H), 1.40-1.69 (m, 4H), 1.93-2.09 (m, 2H), 2.14-2.25 (m, 1H), 2.71-2.94 (m, 2H), 3.01-3.29 (m, 4H), 3.57-3.75 (m, 2H), 3.77 (d, J=16.4 Hz, 1H), 3.85 (d, J=16.4 Hz, 1H), 3.92-4.19 (m, 3H), 5.85 (s, 1H), 6.70 (s, 1H), 6.76 (s, 1H), 6.87-6.93 (m, 1H), 6.97-7.09 (m, 2H), 7.23-7.35 (m, 1H), 7.38 (d, J=3.2 Hz, 1H), 7.67 (d, J=3.2 Hz, 1H), 7.74-7.84 (m, 1H); ESI-MS (m/z) 639.

Example 10

[Chemical Formula 13]

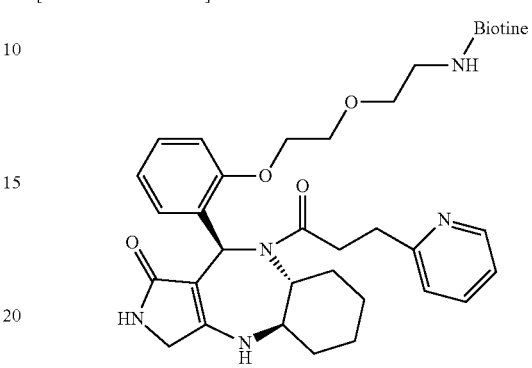

Step 1

The compound of Example 7 (25.3 mg, 0.0488 mmol) and biotin (35 mg, 0.146 mmol) were dissolved in dimethylformamide (2.0 ml). To the solution was added EDCl (28.1 mg, 0.146 mmol), and the mixture was stirred at room temperature for 16 hours. To the reaction solution was added ethyl acetate, and the mixture was washed with water and a saturated brine successively, and dried over anhydrous sodium sulfate. The solvent was removed under reduced pressure to obtain a compound of Example 10 (37.1 mg, 99%).

$^1$H-NMR (300 MHz, DMSO-d6) δ=0.51-0.69 (m, 1H), 0.79-1.15 (m, 4H), 1.21-1.70 (m, 4H), 1.42-1.80 (m, 10H), 1.90-2.23 (m, 2H), 2.53-2.63 (m, 2H), 2.76-2.87 (m, 3H), 2.92-3.00 (m, 2H), 3.53-3.77 (m, 2H), 3.78 (d, J=16.7 Hz, 1H), 3.85 (d, J=16.7 Hz, 1H), 3.95-4.06 (m, 1H), 4.07-4.17 (m, 2H), 4.26-4.34 (m, 2H), 5.87 (s, 1H), 6.36 (s, 1H), 6.38 (m, 1H), 6.68 (s, 1H), 6.74 (m, 1H), 6.85-6.95 (m, 1H), 6.99-7.05 (m, 2H), 7.14-7.22 (m, 1H), 7.23-7.33 (m, 2H), 7.63-7.72 (m, 1H), 7.75-7.83 (m, 1H), 8.53-8.51 (m, 1H); ESI-MS (m/z) 747.

Example 11

Measurement of Glucose Uptake Activity

A male Wistar rat was decapitated and exsanguinated, and then a paratesticular adipose tissue was resected therefrom after laparotomy. The tissue was cut in a KRH (Krebs-Ringer HEPES: 130 mM NaCl, 4.7 mM KCl, 1.2 mM $KH_2PO_4$, 1.2 mM $MgSO_4$, 1 mM $CaCl_2$, 25 mM HEPES) containing a BSA (bovine serum albumin), a collagenase (type I) was added thereto, and the resultant was subjected to a digestive treatment for about 40 minutes to obtain isolated adipocytes. The buffer was replaced to remove the collagenase, and a 2% BSA/KRH solution was added thereto, whereby the adipocytes were floated again to obtain a adipocytes suspension.

The glucose uptake activity of a test substance compound was evaluated in accordance with Non-Patent Document 14: Simpson et al., *Annual Review of Biochemistry*, 55, 1059, (1986). Thus, 200 μl of the adipocytes suspension was dispensed into each polystyrene test tube, 100 μl of a solution containing the test substance compound was added thereto, and the test tube was shaken and incubated at 37° C. for 30 minutes. The glucose uptake activity was evaluated by measuring the amount of 2-[$^{14}$C(U)]-deoxy-D-glucose uptaken per unit time. Thus, the 2-[$^{14}$C(U)]-deoxy-D-glucose was added to the preincubated adipocytes suspension at the final concentration of 0.5 µCi/sample, and after 5 minutes, cytochalasin B was added thereto at the final concentration of 10 µM to stop the glucose uptake. Dinonyl phthalate was superposed over the solution, the resultant was centrifuged to separate the fat cells from the buffer, and the amount of the 2-[$^{14}$C(U)]-deoxy-D-glucose contained in the fat cell layer was measured by a liquid scintillation counter, whereby the uptaken glucose amount was determined. The glucose uptake of insulin (100 nM) was evaluated in the same manner and considered to be 100%, and thus the $EC_{50}$ value of each compound was obtained.

The glucose uptake activity (the $EC_{50}$ value, µM) of each test substance compound, evaluated using this system, is shown in Table 1. It should be noted that N-deacetylcolchicine (Toront, Product No. 198920) did not exhibit glucose uptake activity.

TABLE 1

Glucose uptake activity of each compound

| Compound Number | Glucose uptake activity ($EC_{50}$ value, µM) |
|---|---|
| Compound 1 | 0.008 |
| Compound 3 | 0.014 |
| Compound 4 | 0.006 |
| Compound 5 | 1.0 |
| Compound 6 | 4 |

Example 12

Examination of Hypoglycemic Effect of "Glucose Uptake Enhancer" in Db/Db Mouse

Each of Compounds 5 and 6 excellent in physical properties and stability was orally administered to a C57BL/KsJ-db/dbJcl mouse fasted for about 20 hours, and the blood was taken from the tail vein of the mouse immediately before and at 30, 60, 120, and 180 minutes after the administration, to measure the blood glucose level. 0.5% methylcellulose or 50% polyethylene glycol was used as a dosing vehicle.

Compounds 3 and 6 were single-administered in the amount of 100 mg/kg, and Compound 5 was single-administered in the amount of 10 mg/kg. As a result, Compounds 3, 5, and 6 had a hypoglycemic effect of 25% or more against the control.

Example 13

Measurement of Akt Phosphorylation Activity

The Akt phosphorylation activity of a test substance compound was measured in a human liver-derived HLF cell as follows. Using a Dulbecco MEM medium containing 10% fetal calf serum (FCS), the HLF cells were seeded in a 96-well plate at a ratio of $2 \times 10^4$ cells/well. The HLF cells were cultured in the presence of 5% $CO_2$ at 37° C. for about 5 hours to achieve sufficient adherent, and the medium was removed by suction. The HLF cells were further cultured in the same manner overnight in a Dulbecco MEM medium containing 0.1% BSA without serum. The medium was removed by suction, a Dulbecco MEM medium containing a test substance compound and 0.1% BSA was added to the plate, and the HLF cells were treated with the test substance compound at 37° C. for 15 minutes in the presence of 5% $CO_2$. Then, the 96-well plate was placed on ice, the medium was removed by suction, a lysis buffer (containing 1 mM PMSF) at ice temperature was added to the plate, and the resultant was frozen at –80° C. The lysis buffer was prepared in accordance with a package insert of a phosphorylated Akt measurement kit (Cell Signaling Technologies, Product No. 7160, PathScanR Phospho-Akt1 (Ser473) Sandwich ELISA Kit). The frozen 96-well plate was returned to room temperature to thaw the extract solution (the lysate), and the phosphorylated Akt amount was measured using the phosphorylated Akt measurement kit in accordance with the package insert. The Akt phosphorylation property of each test substance is shown in FIG. 1.

As is clear from Table 1 and FIG. 1, in the test substance compounds, there was a good correlation between the glucose uptake activity and the Akt phosphorylation activity. Thus, it was strongly suggested that both the actions were involved in the same signaling pathway. It should be noted that N-deacetylcolchicine did not exhibit Akt phosphorylation activity.

Example 14

Binding Assay of $^3$H-Labeled Compound 1 Using HLF Cell Membrane

A cell membrane of a human liver-derived HLF cell was prepared as follows. HLF cells were approximately confluently cultured in a Dulbecco MEM medium containing 10% FCS in a cell culture dish having a diameter of 15 cm. The HLF cells cultured in 30 dishes were scraped by a cell scraper in the presence of an HMEE buffer (20 mM HEPES-KOH, 1 mM EDTA, 1 mM EGTA, and 2 mM $MgCl_2$) to obtain about 30 ml of a cell suspension. The suspension was homogenized using a TEFLON (registered trademark) homogenizer (ice temperature, 1000 rpm, 15 stroke) and centrifuged at a low rate (1500 rpm, 5 minutes). The supernatant was further centrifuged at a high rate (12000 rpm, 30 minutes), and the precipitate was suspended in 1 ml of an HMEE buffer to obtain a cell membrane solution. The cell membrane solution had a protein of 3.5 mg/ml, which was measured by Protein assay (BioRad) using BSA as a standard.

The binding assay of the $^3$H-labeled Compound 1 on thus obtained cell membrane was carried out as follows. The above cell membrane solution was 6-fold diluted with an RBA buffer (75 mM Tris-HCl, 12.5 mM $MgCl_2$, 2 mM EDTA, pH 7.4). 25 µl of the cell membrane solution and 25 µl of an RBA buffer containing the unlabeled Compound 1 at 0 or 400 µM (assay final concentration of 100 µM) were added to a 96-well plate, and thereto was further added 50 µl of an RBA buffer containing the $^3$H-labeled Compound 1. The plate was shaken at room temperature for 1 hour, and the cell membrane was collected by a cell harvester on a filter plate (Unifilter GF/C, Perkin Elmer, Product No. 6005174), which was blocked with an RBA buffer containing 2% BSA and 0.5% polyethyleneimine beforehand. The filter plate was well washed with a TBS (20 mM Tris-HCl, 0.15 M NaCl, pH 7.4) containing 0.05% Twee-20 and sufficiently dried, 30 µl of a liquid scintillator (Microscinti 0, Packard) was added to the filter plate, and the $^3$H count was measured by Topcount (Packard). The binding of the sample added with the unlabeled Compound 1 at the final concentration 100 µM was considered as the nonspecific binding of the $^3$H-labeled Compound 1, and the difference between the nonspecific binding and the binding of the sample not added with the unlabeled Compound 1 was considered as the specific binding.

Figure 2:
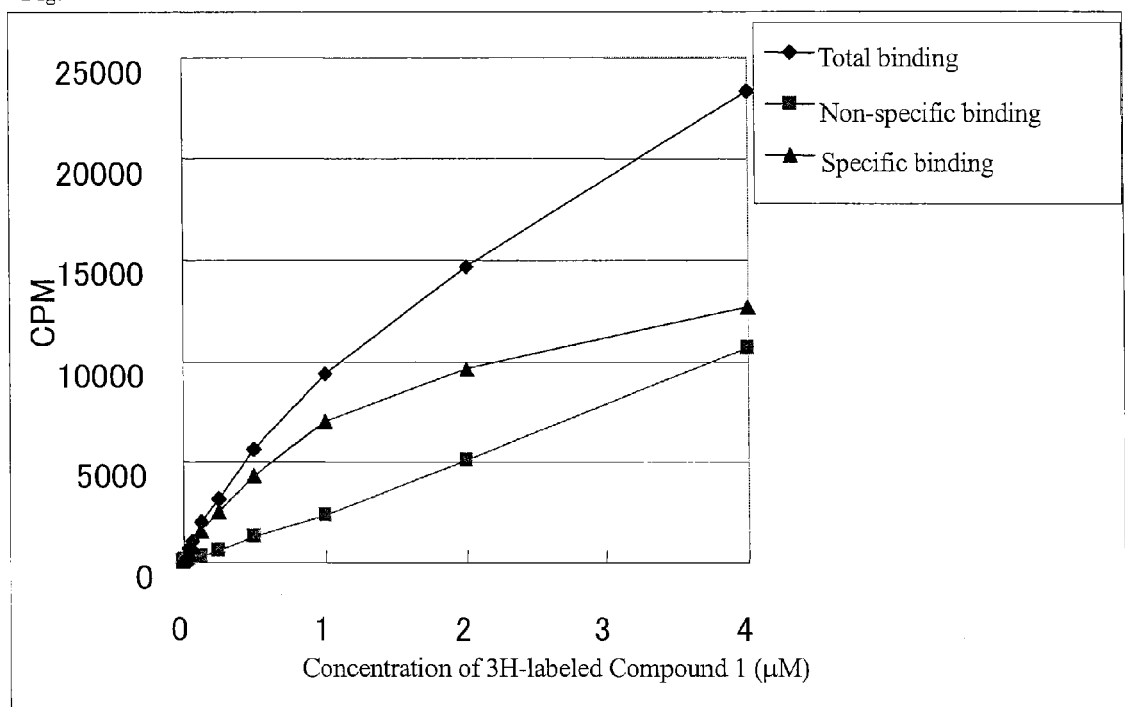
FIG. 2 is a graph showing the results of $^3$H-labeled Compound 1 binding assay using an HLF cell membrane in Example 14.

As shown in FIG. 2, the binding in a saturable manner of the $^3$H-labeled Compound 1 to the HLF cell membrane was observed, and Compound 1 had a Kd value of 0.93 µM, calculated by Scatchard plot. This value approximately corresponded to the Akt phosphorylation activity of Compound 1 shown in Example 13. Thus, it was strongly suggested that the observed binding to the protein on the cell membrane is a response leading the Akt phosphorylation and the glucose uptake.

Example 15

Extraction, Affinity Purification and Identification of $^3$H-Labeled Compound 1-Binding Protein from HLF Cell Membrane (1) Extraction of the Binding Protein from HLF Cell Membrane The $^3$H-labeled Compound 1-binding protein observed in Example 14 (hereinafter referred to as the binding protein) was solubilized as follows. 400 μl of an RBA buffer containing 0.25% or 0.125% digitonin was added at the final concentration of 0.2% or 0.1% to 100 μl of a HMEE buffer solution containing 3.5 mg/ml of the HLF cell membrane prepared in the same manner as Example 14, and the solution was mixed and left at room temperature for 1 hour. The supernatant obtained by centrifugation (15000 rpm, 30 minutes) was used as an extract solution, and the amount of the binding protein in the extract solution was measured by the following method using gel filtration with PD10 (GE Healthcare, Product No. 17-0851-01) for measuring the specific binding of the $^3$H-labeled Compound 1 to the protein (hereinafter referred to as the PD10 method).

Figure 3:
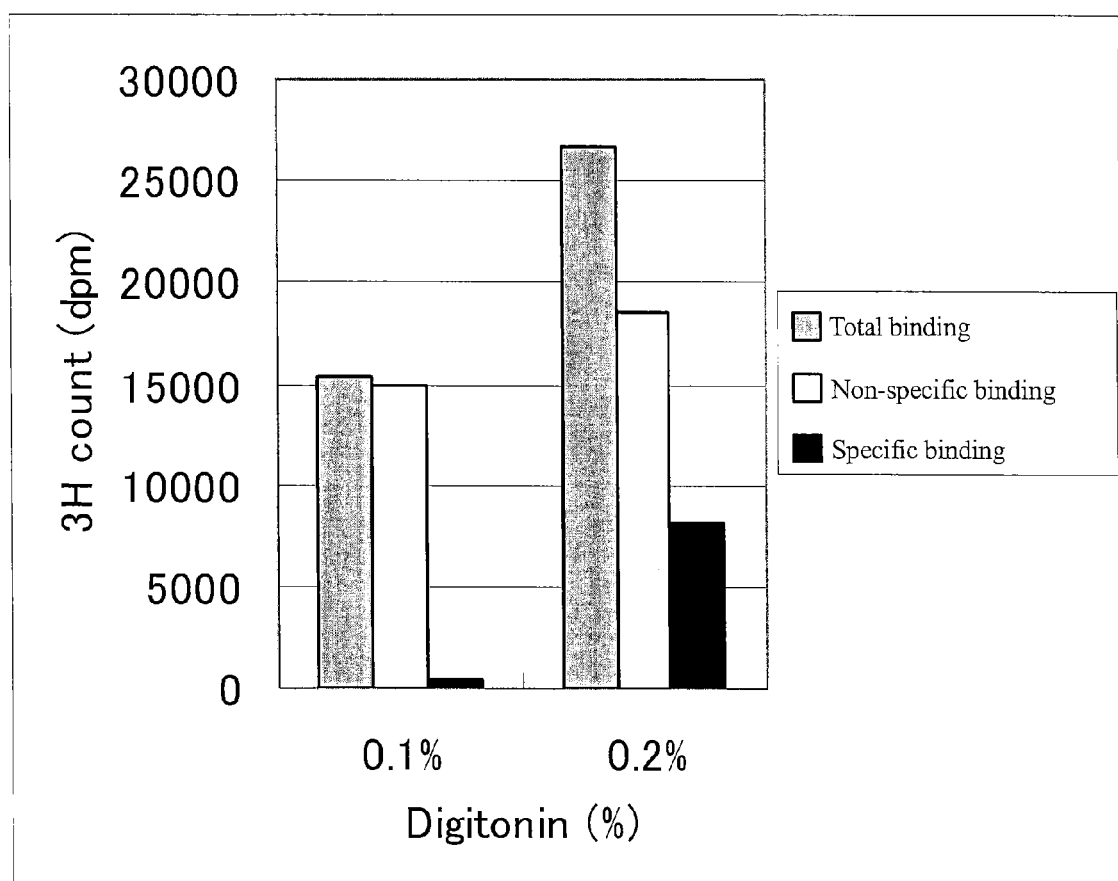
FIG. 3 is a graph showing the results of binding protein extraction from the HLF cell membrane with Digitonin in Example 15 (1)

The PD10 method was carried out as follows. To a microtube were added 250 μl of an RBA buffer, 100 μl of an RBA buffer containing 0 or 500 μM of the unlabeled Compound 1, 100 μl of the above extract solution, and 50 μl of an RBA buffer containing 2.5 μM of the $^3$H-labeled Compound 1 successively, and the resultant mixture was stirred and left at room temperature for 1 hour. The entire reaction solution (0.5 ml) was added to a PD10 column sufficiently substituted with the RBA buffer, 2 ml of the RBA buffer was passed through the PD10 column, and thereafter further eluate by 1.5 ml of the RBA buffer was collected as a high-molecular fraction containing the protein, 15 ml of a liquid scintillator was added thereto, and the amount of the $^3$H-labeled Compound 1 contained in the high-molecular fraction was measured by a scintillation counter. The count of the sample added with the unlabeled Compound 1 at the final concentration of 100 μM was considered to correspond to the nonspecific binding, the difference between the nonspecific binding count and the count of the sample not added with the unlabeled Compound 1 was considered to correspond to the specific binding, and thus the amount of the binding protein contained in the extract solution was evaluated. As shown in FIG. 3, the binding protein was judged to be extracted from the cell membrane with 0.2% of digitonin.

(2) Preparation of Affinity Column

Figure 4:
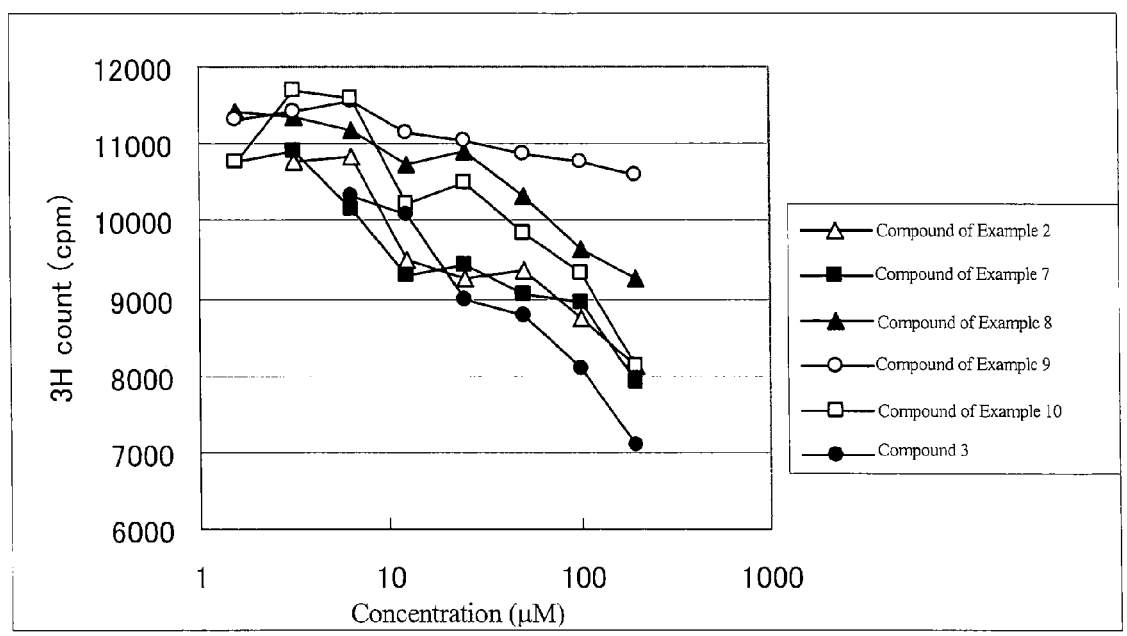
FIG. 4 is a graph showing the binding ability of a probe molecule to the binding protein measured in Example 15 (2)

The inhibitory activity of each of the probe molecule compounds synthesized in Examples 2 and 7 to 10 against the binding of the $^3$H-labeled Compound 1 to the HLF cell membrane was measured by the method described in Example 14 to confirm whether the probe compound could be bound to the binding protein like Compound 1. Also Compound 3, which had relatively potent activity in the glucose uptake described in Example 11 and in the Akt phosphorylation activity described in Example 13, was evaluated. As a results, as shown in FIG. 4, each probe compound inhibited the binding of the $^3$H-labeled Compound 1 to the cell membrane to some extent, and thus was found to have a binding ability to the binding protein.

An affinity column was prepared using Compound 2 obtained in Example 2, which was selected based on the above results. Compound 2 was fixed to an affinity column with a carrier having an N-hydroxysuccinimide group, NHS-Activated Separose HP, (GE Healthcare, Product No. 17-0716-01, HiTrap NHS-Activated Separose HP (1 ml)) using an amino group connected to a linker. The column was washed with 5 ml of 1 mM hydrochloric acid, 1.5 ml of a 0.2 M NaHCO$_3$ solution containing 2 mM of Compound 2 was added to the column, and the column was left at room temperature for 1 hour. 3 ml of 1 M Tris-HCl (pH 8.5) was further added to the column, and the resultant was left at room temperature for 30 minutes, to achieve blocking. The column was washed with 5 ml of distilled water, whereby a Compound 2-fixed affinity column was obtained. The binding of Compound 2 was confirmed such that the amount of Compound 2 passed through the column in this procedure was determined by a reversed-phase HPLC. Furthermore, using Compound 7 obtained in Example 7, a Compound 7-fixed affinity column was prepared in the same manner as the Compound 2-fixed affinity column.

(3) Affinity Purification of Binding Protein from HLF Cell Membrane and Identification of Binding Protein The binding protein was extracted from the HLF cell membrane as follows. 4.8 ml of an RBA buffer containing 0.25% digitonin was added to 1.2 ml of a solution containing 3.7 mg/ml of the HLF cell membrane prepared in the same manner as Example 14, and the resultant solution was mildly stirred and left at room temperature for 1 hour. 6 ml of the supernatant, obtained by centrifugation (15000 rpm, 30 minutes) for removing insoluble contents, was diluted with 24 ml of an RBA buffer, to obtain an HLF cell membrane extract solution.

Figure 5:
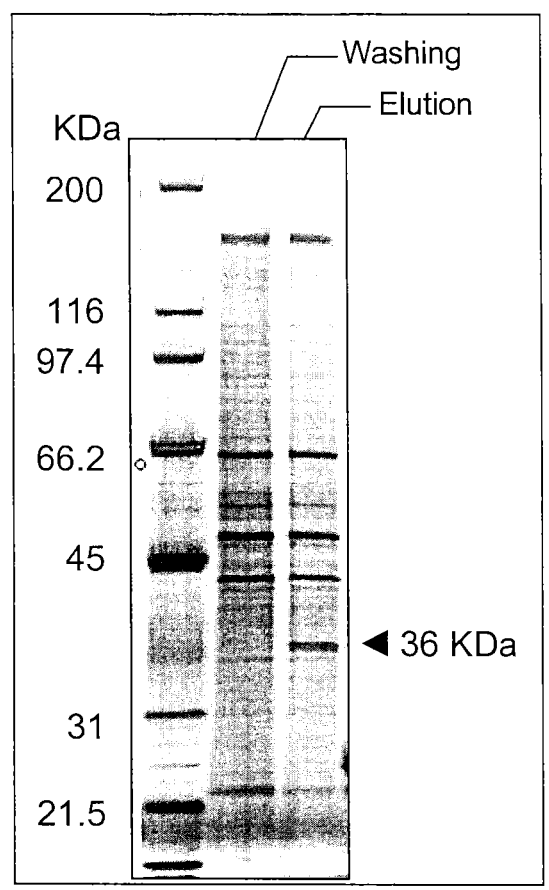
FIG. 5 is a view showing the acquisition of the binding protein in an affinity column of Example 15 (3)

Two columns, which were blocked with 1M Tris-HCl (pH 8.5) without the compound fixation, were connected to the upstream of the Compound 2-fixed affinity column prepared in (2). The total amount of the above HLF cell membrane extract solution was added to the column at room temperature at a flow rate of 0.5 ml/minute to adsorb the binding protein. Only the Compound 2-fixed affinity column was removed and washed with a RBA buffer containing 0.04% digitonin at a flow rate of 1 ml/minute for about 25 minutes. The eluate in the last 3 minutes of this washing step was collected as a washing fraction (3 ml). Furthermore, a solution (elution buffer) having the same composition as the washing buffer above except for containing 200 μM of Compound 4, which was high in the glucose uptake activity described in Example 11 and the Akt phosphorylation activity described in Example 13, was added to the column at a flow rate of 1 ml/minute for 3 minutes, and the eluate was collected as an elution fraction (3 ml). Each of the washing fraction and the elution fraction were concentrated to about 45 μl by Centricon-10 ultrafiltration, and 7.5 μl of the resultant was subjected to an SDS polyacrylamide gel electrophoresis and a silver staining treatment (Silver Stain Kit, Protein, GE Healthcare, Product No. 17-1150-01, carried out in accordance with the attached manual). Thus, the fractions were compared with respect to the protein contained therein. As a result, as shown in FIG. 5, a band migrated at a position of about 36 KDa was specifically observed in the elution fraction. Also the columns, which were blocked without the compound fixation, were evaluated in the same manner. As a result, the band fractionated at the position of about 36 KDa was not observed.

Furthermore, a fraction eluted with Compound 4 using the Compound 2-fixed affinity column prepared in the same manner was subjected to an SDS polyacrylamide gel electrophoresis and a CBB staining treatment, and the specific band at 36 KDa was cut off and put in a siliconized micro-test tube. The specific band was washed with 600 μl of acetonitrile 3 times and with a 50 mM aqueous ammonium hydrogen carbonate solution 3 times. The specific band was further washed with a 50% acetonitrile solution containing 25 mM of ammonium hydrogen carbonate for about 15 minutes 3 times. After removing the solution, 100 μl of a solution containing 6 M of guanidine hydrochloride, 2 mM of EDTA, and 0.5 M of tris-hydrochloric acid (pH 8) was added to the residue, and 10 µl of a reduction solution containing DTT, 6 M of guanidine hydrochloride, 2 mM of EDTA, and 0.5 M of tris-hydrochloric acid (pH 8) was further added thereto, whereby a reduction reaction was carried out at room temperature for about 2 hours. Then, the mixture was blocked from light, a liquid prepared by adding 25 mg of iodoacetic acid to 0.3 ml of a solution containing 6 M of guanidine hydrochloride, 2 mM of EDTA, and 0.5 M of tris-hydrochloric acid (pH 8) was added thereto, and the resultant mixture was left for about 30 minutes to alkylate the free thiol group. The reaction solution was removed, and the gel was dehydrated by adding acetonitrile and by removing the solvent using a centrifugal concentration device. 10 µl of a trypsin solution (trypsin: Sigma Corporation, Proteomics grade, 50 mM ammonium hydrogen carbonate (pH 7.6)) was added to the residue to carry out an enzymatic digestion at 36° C. for about 15 hours. After the trypsin digestion, the reaction solution was transferred into another siliconized micro-test tube. The gel was washed with 100 µl of 0.1% formic acid-60% acetonitrile for 20 minutes, and the solution was transferred into the same siliconized micro-test tube. This process was repeated 3 times to extract the peptide. The solvent was removed from the obtained trypsin digestive solution under reduced pressure by a centrifugal concentration device to obtain a sample for nano-LC/MS/MS measurement. The trypsin digest was subjected to a nano-LC/MS/MS (HPLC: Paradaigm MS4, Michrom Bioresources, MS: electrospray-ionization linear-trap mass spectrometer LTQ, Thermo Fisher Scientific K. K.). The obtained MS and MS/MS data were analyzed using a database retrieval software (Mascot, Matrix Science K. K.) MSDB and NCBI nr databases were used in this analysis, and the organism species was limited to Homo Sapience. As a result, the obtained protein was identified with high score to a GTP-binding protein β subunit (hereinafter referred to as Gβ) in both the databases (Mascot score 245 and 244, respectively). Thus, it was clarified that the protein was Gβ.

Example 16

Elution of Binding Protein (Gβ) with Compound Using Affinity Column Experiment

Using the Compound 2-fixed affinity column prepared in Example 15 and the Compound 7-fixed affinity column prepared in Example 15 (2), Compound 7 having an activity of binding to the binding protein equal to Compound 2, an affinity column operation was carried out in the same manner as Example 15.

Figure 6:
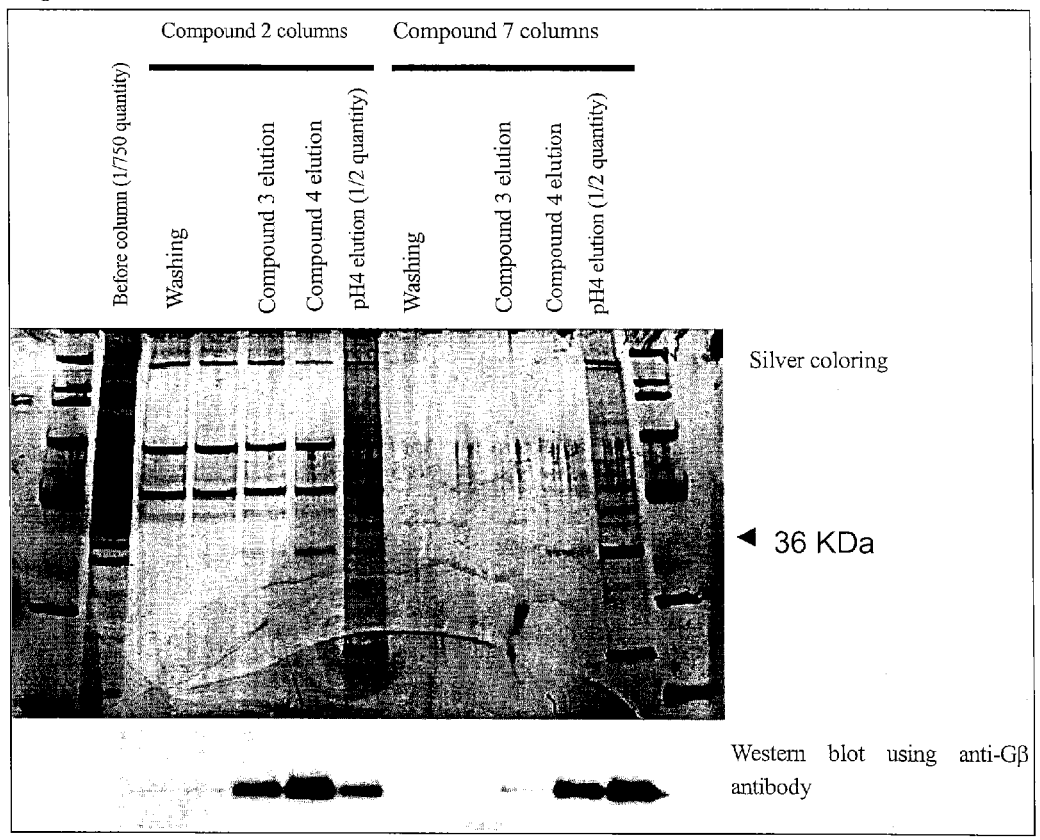
FIG. 6 is a view showing the elution of Gβ from the affinity column depending on the activity of an eluate compound in Example 16.

After washing, the column was eluted with Compound 3 and with Compound 4 successively using RBA buffers containing 0.02% Digitonin and Compounds 3 and 4 (200 µM). It was clear from the results of Examples 11 and 13 that the activity of Compound 3 was lower than that of Compound 4. Thus, each of the Compound 2-fixed affinity column and the Compound 7-fixed affinity column was eluted with Compound 3, Compound 4, and a pH-4 buffer successively, and the resulting eluate was concentrated, subjected to an SDS polyacrylamide gel electrophoresis and silver staining in the same manner as Example 15, and further examined by a Western blot method using an anti-Gβ antibody (Santa Scuz, Product No. sc-261). As a result, the presence of eluted Gβ was observed depending on the activities of the eluate compounds in all the detection methods (FIG. 6).

A hypoglycemic material can be screened such that an appropriate test substance is used instead of Compounds 3 and 4 in the above process, and the Gβ eluted from the Compound 2 or 7-fixed affinity column is detected, whereby the inhibitory activity of the test substance against the binding of the probe compound (the affinity column) to the Gβ is measured.

Example 17

Construction of Animal Cell Expression System (Gβ1, Gγ2)

A PCR was carried out by a common technique using a primer of a synthetic DNA of SEQ ID NO. 1, 2 and a template of a cDNA clone containing the entire human Gβ1 protein-encoding domain. The obtained 1056-bp DNA was digested with restriction enzymes HindIII and XhoI, and purified by a GFX kit (Amersham Biosciences). The resultant was cloned in HindIII and XhoI sites of a vector pcDNA3.1Hyg(+) (Invitrogen Corporation), and a plasmid was prepared from a cultured medium of a single colony of an *Escherichia coli* JM109 strain having the plasmid. Thus, DNA sequencing was carried out, and a base sequence of SEQ ID NO. 3 (an amino acid sequence of SEQ ID NO. 4) was observed, whereby a pcDNA3.1Hyg(+)-GNB1 was constructed. Furthermore, a plasmid DNA was prepared by a QIAprep plasmid purification kit (QIAGEN) form a *Escherichia coli* cultured medium, and was used for animal cell transfection. In addition, a PCR was carried out by a common technique using a primer of a synthetic DNA of SEQ ID NO. 5, 6 and a template of a cDNA clone containing the entire human Gγ2 protein-encoding domain. The obtained 255-bp DNA was digested with restriction enzymes EcoRI and XhoI, and purified by the GFX kit (Amersham Biosciences). The resultant was cloned in EcoRI and XhoI sites of a vector pcDNA3.1(+) (Invitrogen Corporation), and a base sequence of SEQ ID NO. 7 (an amino acid sequence of SEQ ID NO. 8) was observed, whereby a pcDNA3.1(+)-GNG2 was constructed. Furthermore, a plasmid DNA was prepared from a cultured medium of a transformed *Escherichia coli* JM109 strain, and was used for animal cell transfection.

Example 18

Measurement of Binding of $^3$H-Labeled Compound 1 Using Gβ1- and Gγ2-Expressing HEK293T Cell Extraction Liquid A protein was expressed in an HEK293T cell using the expression plasmid prepared in Example 17. The HEK293T cell was cultured in a cell culture dish having a diameter of 10 cm, Gβ1 and Gγ2 were simultaneously transfected by using Lipofectamine 2000 (Invitrogen Corporation, Product No. 11618-019) in accordance with the attached manual, and the expressing cell (Gβ1γ2) was collected. A cell (Mock) was prepared and collected as control by transfecting a vector without gene insertion instead of the expression vector. The collected cell was washed with PBS, suspended in 1 ml of a lysis buffer (75 mM Tris-HCl, 12.5 mM MgCl$_2$, 2 mM EDTA, pH 7.4, a protease inhibitor cocktail (Rosch Diagnostics, 11-697-498-001), 0.3% CHAPS), subjected to ultrasonic homogenization, and centrifuged (15000 rpm, 20 minutes), whereby the supernatant was obtained as an extract solution. Determination of protein concentration was carried out by a protein assay (BioRad) using a BSA as standard, whereby it was confirmed that the Gβ1γ2 and the Mock had the same protein concentration of the extract solution.

Figure 7:
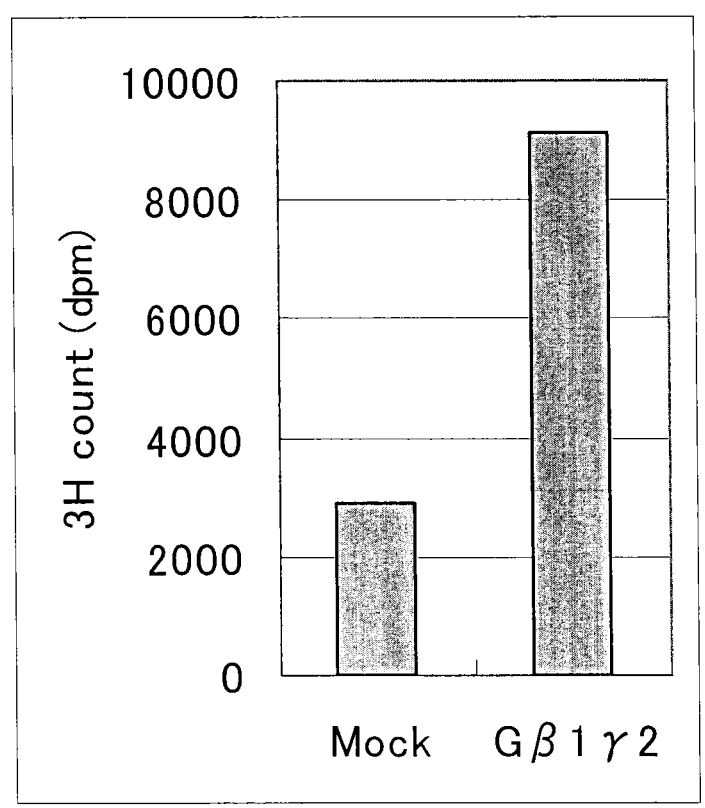
FIG. 7 is a graph showing the presence of the binding protein in a Gβ1γ2-expressing HEK293T cell extracts solution.

The binding activity of the $^3$H-labeled Compound 1 to the protein contained in the above extract solution was evaluated by the PD10 method described in Example 15 (1). Thus, 300 µl of the extract solution, 100 µl of an RBA buffer (75 mM Tris-HCl, 12.5 mM MgCl$_2$, 2 mM EDTA, pH 7.4) containing 0 or 500 µM of the unlabeled Compound 4, and 100 µl of an RBA buffer containing 1.25 µM of the $^3$H-labeled Compound 1 were added successively, and the mixture was stirred and left at room temperature for 1 hour. The entire reaction liquid (0.5 ml) was added to a PD10 column sufficiently substituted with the RBA buffer, 2 ml of the RBA buffer was passed through the PD10 column, and further 1.5 ml of the RBA buffer eluate was collected as a high-molecular fraction containing the protein, 15 ml of a liquid scintillator was added thereto, and the amount of the $^3$H-labeled Compound 1 contained in the high-molecular fraction was measured by a scintillation counter. The count of the sample added with the unlabeled Compound 4 at the final concentration of 200 µM was considered to correspond to the nonspecific binding, the difference between the nonspecific binding count and the count of the sample not added with the unlabeled Compound 4 was considered to correspond to the specific binding, and thus the amount of the binding protein contained in the extraction liquid was evaluated. As shown in FIG. 7, the amount of the binding protein was higher in the extract solution containing the Gβ1γ2 than in the extract solution containing the Mock.

Then, a part of the above extraction liquid was subjected to an SDS polyacrylamide gel electrophoresis, and examined by a Western blot method using an anti-Gβ antibody (SantaCruz, Product No. sc-261). As a result, the expressed Gβ amount was larger in the extraction liquid containing the Gβ1γ2 than in the extract solution containing the Mock.

Example 19

Construction of Insect Cell Expression System (Gβ1 to Gβ5, Gγ2-Myc, Gαi1-His) and Production (1) Construction of 6×His-Gαi1 Expression System A PCR was carried out by a common technique using a primer of a synthetic DNA of SEQ ID NO. 9, 10 and a template of a cDNA clone containing the entire human trimeric GTP-binding protein αi1 subunit (Gαi1) protein-encoding domain. The obtained 1116-bp DNA was subcloned into a vector pCR4Blunt-TOPO (Invitrogen Corporation, Product No. K2875), and a base sequence of SEQ ID NO. 11 (an amino acid sequence of SEQ ID NO. 12) was observed. The resultant was cut by restriction enzymes BamHI and XhoI, and inserted into the restriction enzyme sites in a vector pFastBac1 of a Bac-to-Bac baculovirus protein expression system (Invitrogen Corporation, Product No. 10359-016), whereby a pFB1-6×His-GNAI1 was constructed. Furthermore, a bacmid DNA was prepared from a cultured medium of a transformed *Escherichia coli* DH10Bac strain in accordance with the attached manual. The bacmid DNA was transfected into an insect cell line Sf-21 by a lipofection method, to obtain a recombinant virus capable of expressing a 6×His-Gαi1 protein having a His tag sequence at the amino terminal. The Sf-21 cell was further infected with the virus, whereby the virus titer was increased such that a desired amount of the recombinant protein could be obtained. The expression of the desired recombinant protein in the virus-infected cell lysate was detected by a Western blot method using a specific antibody.

(2) Construction of Gβ1 Expression System

A PCR was carried out by a common technique using a primer of a synthetic DNA of SEQ ID NO. 13, 14 and a template of a cDNA clone containing the entire human Gβ1 protein-encoding domain. The obtained 1051-bp DNA was subcloned into a vector pCR4Blunt-TOPO (Invitrogen Corporation, Product No. K2875), and a base sequence of SEQ ID NO. 15 (an amino acid sequence of SEQ ID NO. 16) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-GNB1 was constructed. Furthermore, a bacmid DNA was prepared from a cultured medium of a transformed *Escherichia coli* DH10Bac strain in accordance with the attached manual. The bacmid DNA was transfected into an insect cell line Sf-21 by a lipofection method, to obtain a recombinant virus capable of expressing the Gβ1. The Sf-21 cell was further infected with the virus in accordance with the manual, whereby the virus titer was increased such that a desired amount of the recombinant protein could be obtained. The expression of the desired recombinant protein in the virus-infected cell extract solution was detected by a Western blot method using a specific antibody.

(3) Construction of Gβ2 Expression System

A PCR was carried out by a common technique using a primer of a synthetic DNA of SEQ ID NO. 17, 18 and a template of a cDNA clone containing the entire human Gβ2 protein-encoding domain. The obtained 1048-bp DNA was subcloned into a vector pCR4Blunt-TOPO (Invitrogen Corporation, Product No. K2875), and a base sequence of SEQ ID NO. 19 (an amino acid sequence of SEQ ID NO. 20) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-GNB2 was constructed. Furthermore, a bacmid DNA was prepared from a cultured medium of a transformed *Escherichia coli* DH10Bac strain in accordance with the attached manual. The bacmid DNA was transfected into an insect cell line Sf-21 by a lipofection method, to obtain a recombinant virus capable of expressing the Gβ2. The Sf-21 cell was further infected with the virus in accordance with the manual, whereby the virus titer was increased such that a desired amount of the recombinant protein could be obtained. The expression of the desired recombinant protein in the virus-infected cell extract solution was detected by a Western blot method using a specific antibody.

(4) Construction of Gβ3 Expression System

A PCR was carried out by a common technique using a primer of a synthetic DNA of SEQ ID NO. 21, 22 and a template of a cDNA library of a healthy human skin fibroblast. The obtained 1078-bp DNA was subcloned into a vector pCR4Blunt-TOPO (Invitrogen Corporation, Product No. K2875), and a base sequence of SEQ ID NO. 23 (an amino acid sequence of SEQ ID NO. 24) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-GNB3 was constructed. Furthermore, a bacmid DNA was prepared from a cultured medium of a transformed *Escherichia coli* DH10Bac strain in accordance with the attached manual. The bacmid DNA was transfected into an insect cell line Sf-21 by a lipofection method, to obtain a recombinant virus capable of expressing the Gβ3. The Sf-21 cell was further infected with the virus in accordance with the manual, whereby the virus titer was increased such that a desired amount of the recombinant protein could be obtained. The expression of the desired recombinant protein in the virus-infected cell extract solution was detected by a Western blot method using a specific antibody.

(5) Construction of Gβ4 Expression System

A PCR was carried out by a common technique using a primer of a synthetic DNA of SEQ ID NO. 25, 26 and a template of a cDNA library of a human liver carcinoma-derived HLF cell. The obtained 1055-bp DNA was subcloned into a vector pCR4Blunt-TOPO (Invitrogen Corporation, Product No. K2875), and a base sequence of SEQ ID NO. 27 (an amino acid sequence of SEQ ID NO. 28) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-GNB4 was constructed. Furthermore, a bacmid DNA was prepared from a cultured medium of a transformed *Escherichia coli* DH10Bac strain in accordance with the attached manual. The bacmid DNA was transfected into an insect cell line Sf-21 by a lipofection method, to obtain a recombinant virus capable of expressing the Gβ4. The Sf-21 cell was further infected with the virus in accordance with the manual, whereby the virus titer was increased such that a desired amount of the recombinant protein could be obtained. The expression of the desired recombinant protein in the virus-infected cell extract solution was detected by a Western blot method using a specific antibody.

(6) Construction of Gβ5 Expression System

A PCR was carried out by a common technique using a primer of a synthetic DNA of SEQ ID NO. 29, 30 and a template of a cDNA library of a human liver carcinoma-derived HLF cell. The obtained 1093-bp DNA was subcloned into a vector pCR4Blunt-TOPO (Invitrogen Corporation, Product No. K2875), and a base sequence of SEQ ID NO. 31 (an amino acid sequence of SEQ ID NO. 32) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-GNB5 was constructed. Furthermore, a bacmid DNA was prepared from a cultured medium of a transformed *Escherichia coli* DH10Bac strain in accordance with the attached manual. The bacmid DNA was transfected into a silkworm cell line Sf-21 by a lipofection method, to obtain a recombinant virus capable of expressing the Gβ5. The Sf-21 cell was further infected with the virus in accordance with the manual, whereby the virus titer was increased such that a desired amount of the recombinant protein could be obtained. The expression of the desired recombinant protein in the virus-infected cell extract solution was detected by a Western blot method using an specific antibody.

(7) Construction of Myc-Gγ2 Expression System

A PCR was carried out by a common technique using a primer of a synthetic DNA of SEQ ID NO. 33, 34 and a template of a cDNA clone containing the entire human trimeric GTP-binding protein γ2 subunit (Gγ2) protein-encoding domain. The obtained 290-bp DNA was subcloned into a vector pCR4Blunt-TOPO (Invitrogen Corporation, Product No. K2875), and a base sequence of SEQ ID NO. 35 (an amino acid sequence of SEQ ID NO. 36) was observed. The resultant was cut by restriction enzymes EcoRI and XhoI, and inserted into the restriction enzyme sites in a vector pFastBac1 of a Bac-to-Bac baculovirus protein expression system (Invitrogen Corporation, Product No. 10359-016), whereby a pFB1-Myc-GNG2 was constructed. Furthermore, a bacmid DNA was prepared from a cultured medium of a transformed *Escherichia coli* DH10Bac strain in accordance with the attached manual. The bacmid DNA was transfected into a silkworm cell line Sf-21 by a lipofection method, to obtain a recombinant virus capable of expressing a Myc-Gγ2 protein having a Myc tag sequence at the amino terminal. The Sf-21 cell was further infected with the virus in accordance with the manual, whereby the virus titer was increased such that a desired amount of the recombinant protein could be obtained. The expression of the desired recombinant protein in the virus-infected cell lysate was detected by a Western blot method using an antibody specific to the Myc tag sequence.

(8) Coexpression of Gβ1 to Gβ5, Myc-Gγ2, and Gαi1-His in Sf21 and Purification Using Ni-NTA Resin Expression and production of a protein in the insect cell line Sf21 was carried out using the Bac-to-Bac baculovirus protein expression system (Invitrogen Corporation, Product No. 10359-016) in accordance with the attached manual (Instruction Manual). Specifically, the titer of a third or fourth virus solution was detected by a plaque assay, and the baculovirus having a Gβ, Myc-Gγ2, or 6×His-Gαi1 gene was incubated at 28° C. for 65 hours under shaking in an SF900IISFM medium (Invitrogen, Product No. 10902-096) having a level of $10^8$ cells/100 ml in a 250-ml conical flask to obtain an MOI of 2.5. As Gβ, the subtypes Gβ1, Gβ2, Gβ3, Gβ4, and Gβ5 were used in incubation, respectively. After the incubation, the cell was collected by centrifugation (1000 rpm, 5 minutes) and washed with 10 ml of Insect Cell PBS (7.3 mM $NaH_2PO_4$ (pH 6.2), 58 mM KCl, 47 mM NaCl, 5 mM $CaCl_2$). The cell was collected by further centrifugation (3000 rpm, 5 minutes) and stored in the frozen state.

A dimer of Gβ2/Myc-Gγ2 (Gβ2γ2-Myc) was purified as follows from each of the obtained Gβ-expressing cells forementioned. The purification was carried out based on a method reported by Davis et al. (Non-Patent Document 15: Davis et al., *Biochemistry*, 44, 10593, (2005)). Thus, $10^8$ cells were suspended in 2 ml of a lysis buffer (50 mM HEPES (pH 8.0), 3 mM $MgCl_2$, 10 mM 2-mercaptoethanol, 10 μM GDP, a protease inhibitor cocktail (Rosch Diagnostics, 11-697-498-001), 1 mM EDTA, 100 mM NaCl) and centrifuged at 100000 g for 20 minutes to obtain a pellet. Then, the pellet was suspended in 2 ml of an extraction buffer (50 mM HEPES (pH 8.0), 3 mM $MgCl_2$, 10 mM 2-mercaptoethanol, 10 μM GDP, a protease inhibitor cocktail, 50 mM NaCl, 1% sodium cholate). The suspension was stirred at 4° C. for 1 hour and centrifuged at 100000 G for 20 minutes, and the supernatant was obtained as an extract solution (2 ml). 8 ml of Buffer A (50 mM HEPES (pH 8.0), 3 mM $MgCl_2$, 10 mM 2-mercaptoethanol, 10 μM GDP, a protease inhibitor cocktail, 100 mM NaCl, 0.5% Lubrol) was added to the extract solution (2 ml), further 200 μl of Ni-NTA agarose (QIAGEN, Product No. 30210) was added thereto, and the mixture was stirred at 4° C. for 1 hour. The Ni-NTA agarose was collected by centrifugation (3000 rpm, 5 minutes) and washed 3 times with 0.5 ml of a buffer prepared by adding 300 mM of NaCl and 5 mM of imidazole to the Buffer A. Furthermore, the Ni-NTA agarose was suspended in an elution buffer (50 mM HEPES (pH 8.0), 53 mM $MgCl_2$, 10 mM 2-mercaptoethanol, 10 μM GDP, a protease inhibitor cocktail, 250 mM NaCl, 5 mM imidazole, 10 mM NaF, 30 μM $AlCl_3$, 1% sodium cholate), and the suspension was stirred at room temperature for 1 hour. The Gβ2/Myc-Gγ2 was eluted, and the Ni-NTA agarose was removed by centrifugation (10000 rpm, 2 minutes), whereby the supernatant was obtained as a Gβ2/Myc-Gγ2 solution.

The purification of the Gβ2/Myc-Gγ2 was checked by an SDS polyacrylamide gel electrophoresis and a Western blot using an anti-Gβ2 antibody. As a result, the recovery rate from the cell extract solution was about 20%.

Example 20

Evaluation of $^3H$ Binding and Gβ Binding Ability of Compound Using Gβ-Expressing Insect Cell Extract Solution Using the frozen insect cell Sf21 expressing the Gβ1, Myc-Gγ2, and Gαi1-His prepared in Example 19 (8), $10^7$ cells were melted and suspended in 1.3 ml of an RBA buffer containing 1% Triton X-100 (75 mM Tris-HCl, 12.5 mM $MgCl_2$, 2 mM EDTA, pH 7.4). The suspension was subjected to sonication to extract protein and centrifugation (15000 rpm, 15 minutes, 4° C.), whereby the supernatant was obtained as a Gβ1γ2-Myc extract solution (1.3 ml).

The inhibitory activity against the binding of the $^3H$-labeled Compound 1 to the Gβ1γ2-Myc was considered to correspond to the activity of the compounds for binding to the Gβ1γ2-Myc. Thus, the activity of each of Compounds 1, 3, and 6 for binding to the Gβ1γ2-Myc was measured using the above extract solution. The activity of the $^3$H-labeled Compound 1 for binding to the protein contained in the extract solution was measured by the PD10 method described in Example 15 (1). Thus, 100 μl of the extract solution, 300 μl of an RBA buffer (75 mM Tris-HCl, 12.5 mM MgCl$_2$, 2 mM EDTA, pH 7.4) containing or not containing the test substance, and 100 μl of an RBA buffer containing 1.25 μM of the $^3$H-labeled Compound 1 were added successively, and the mixture was stirred and left at room temperature for 1 hour. The entire reaction liquid (0.5 ml) was added to a PD10 column sufficiently substituted with the RBA buffer, 2 ml of the RBA buffer was passed through the PD10 column, and further 1.5 ml of the RBA buffer eluate was collected as a high-molecular fraction containing the protein, 15 ml of a liquid scintillator was added thereto, and the amount of the $^3$H-labeled Compound 1 contained in the high-molecular fraction was measured by a scintillation counter.

Figure 8:
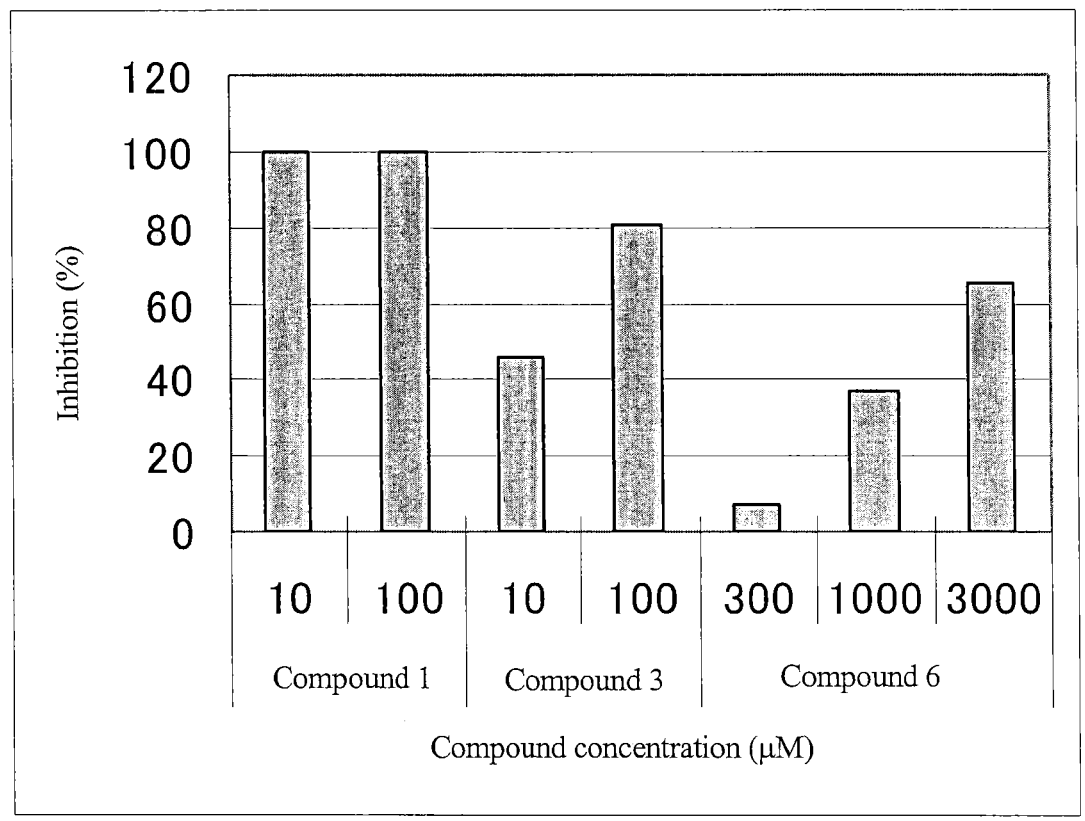
FIG. 8 is a graph showing the evaluation results of the ability of a compound for binding to the Gβ expressed in an insect cell.

The count of the sample not added with the compound was considered to correspond to 0% inhibition, the count of the sample added with the unlabeled Compound 1 at the final concentration of 100 μM was considered to correspond to 100% inhibition, and thus the inhibitory activity of each compound against the binding of the $^3$H-labeled Compound 1 to the Gβγ2-Myc was calculated at each concentration. The results are shown in FIG. 8. Compounds 1, 3, and 6 could be bound to the Gβγ2-Myc, and the binding strength was decreased in the order of Compound 1>Compound 3>Compound 6. Thus, there was a good correlation between the results and the glucose uptake activity described in Example 11 and the Akt phosphorylation activity described in Example 13.

Example 21

$^3$H Binding Assay Using Insect Cell Lysate Expressing Each Subtype of Gβγ2-Myc Using the frozen insect cell Sf21 expressing the subtype Gβ1, Gβ2, Gβ3, Gβ4, or Gβ5 prepared in Example 19 (8), $10^8$ cells were thawed and suspended in 3 ml of a lysis buffer and 2 ml of an RBA buffer (75 mM Tris-HCl, 12.5 mM MgCl$_2$, 2 mM EDTA, pH 7.4) containing 1% Triton X-100. The suspension was stirred at 4° C. for 1 hour to extract protein and centrifuged (100000 G, 20 minutes, 4° C.), whereby the supernatant was obtained as a Gβγ2-Myc extract solution.

In the binding assay of the $^3$H-labeled Compound 1 to each Gβγ2-Myc, an anti-cMyc antibody capable of binding to the Gβγ2-Myc (a monoclonal antibody 9E10) and anti-mouse IgG antibody-immobilized SPA beads (scintillation proximity assay beads, Anti-Mouse PVT SPA Scintillation Beads, GE Healthcare, Product No. RPNQ0017) capable of binding to the anti-cMyc antibody were used. The radioactivity of the $^3$H-labeled Compound 1 bound to the Gβγ2-Myc on the SPA beads was measured by the SPA method.

The forementioned Gβγ2-Myc lysate of each subtype was 2-fold diluted with an RBA buffer. 40 μl of thus diluted solution, 25 μl of an RBA buffer containing 0 or 500 μM of the unlabeled Compound 1, 25 μl of a $^3$H-labeled Compound 1 solution (1.25 μM), 10 μl of a solution containing 200 μg/ml of the anti-cMyc antibody (9E10, SantaCruz, Product No. sc-40), and 25 μl of the SPA beads (20 mg/ml) were added successively to a white 96-well plate. The mixture was shaken for 1 hour and left at room temperature overnight, and the radioactivity was measured by Topcount. The count of the sample added with the unlabeled Compound 1 at the final concentration 100 μM was considered to correspond to the nonspecific binding, and the difference between the nonspecific binding count and the count of the sample not added with the unlabeled Compound 1 was considered to correspond to the specific binding. This method is hereinafter referred to as the SPA method.

Figure 9:
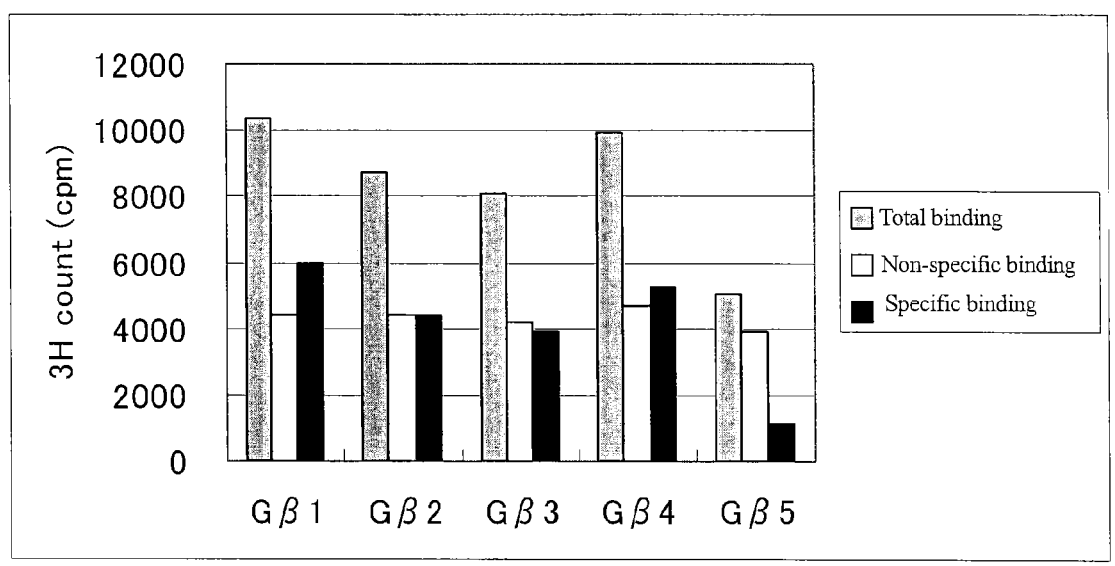
FIG. 9 is a graph showing the binding activity of the $^3$H-labeled Compound 1 to each subtype Gβγ2-Myc.

As shown in FIG. 9, the Gβ1, Gβ2, Gβ3, and Gβ4 exhibited a high specific binding count of the $^3$H-labeled Compound 1, while the Gβ5 exhibited a low binding count.

Example 22

Evaluation of Gβ Binding Activity of Each Compound Using Insect Cell Lysate Expressing Each Subtype Gβγ2-Myc The Gβ binding activity of each of the compounds having the activities described in Examples 11 and 13 (Compounds 1, 3, 5, and 6) and N-deacetylcolchicine in the insect cell lysate expressing each subtype Gβγ2-Myc was evaluated by measuring the inhibitory activity against the binding assay of the $^3$H-labeled Compound 1 in accordance with the method described in Example 21.

The insect cell Sf21 coexpressing the Gβ1, Gβ2, Gβ3, or Gβ4, and Myc-Gγ2 and 6×His-Gαi1 was prepared in the same manner as Example 19 (8) and stored in the frozen state at −80° C. Using the frozen insect cell Sf21 expressing the subtype Gβ1, Gβ2, Gβ3, or Gβ4, 2.5×$10^8$ cells were thawed, suspended in 4 ml of a lysis buffer, and centrifuged (10000 G, 20 minutes, 4° C.) to obtain a pellet. The pellet was suspended in 5 ml of an extraction buffer containing 1% sodium cholate (50 mM HEPES, pH 8.0, 3 mM MgCl$_2$, 1 mM 2-mercaptoethanol, 10 μM GDP, 50 mM NaCl, 1% sodium cholate). The suspension was stirred at 4° C. for 1 hour to extract protein and centrifuged (100000 G, 20 minutes, 4° C.), whereby the supernatant was obtained as a Gβγ2-Myc extract solution.

The binding assay of the $^3$H-labeled Compound 1 to each Gβγ2-Myc was carried out in the same manner as Example 21 except for adding 0.1% Triton X-100 to an RBA buffer and for changing plate size. Thus, 18.7 μl of a mixture solution containing an anti-cMyc antibody (9E10, 54 μg/ml, ZYMED, Product No. 18-0176z) and SPA beads (13.3 mg/ml), 6.25 μl of each subtype Gβγ2-Myc extract solution, 12.5 μl of an RBA buffer (75 mM Tris-HCl, 12.5 mM MgCl$_2$, 2 mM EDTA, pH 7.4) containing or not containing the test substance, and 12.5 μl of a solution containing 1.25 μM of the $^3$H-labeled Compound 1 were added successively to a white 96-well half plate. The mixture was shaken for 1 hour and left at room temperature overnight, and the radioactivity was measured by Topcount. The count of the sample not added with the compound was considered to correspond to 0% inhibition, the count of the sample added with the unlabeled Compound 1 at the final concentration of 50 to 100 μM was considered to correspond to 100% inhibition, and thus the inhibitory activity of each compound against the binding of the $^3$H-labeled Compound 1 to the Gβγ2-Myc was calculated at each concentration. The evaluation results of typical examples using expression proteins corresponding to the Gβ1 and Gβ4 are shown in FIG. 10. Also in the case of using the expression protein corresponding to another subtype Gβ, the same evaluation results were obtained. As shown in FIG. 10, there was a good correlation between the Gβ binding activity and the Akt phosphorylation activity described in Example 13 in Compounds 1, 3, 4, 5, and 6. Thus, it was strongly suggested that the Gβ binding activity resulted in the glucose uptake activity described in Example 11.

Figure 11:
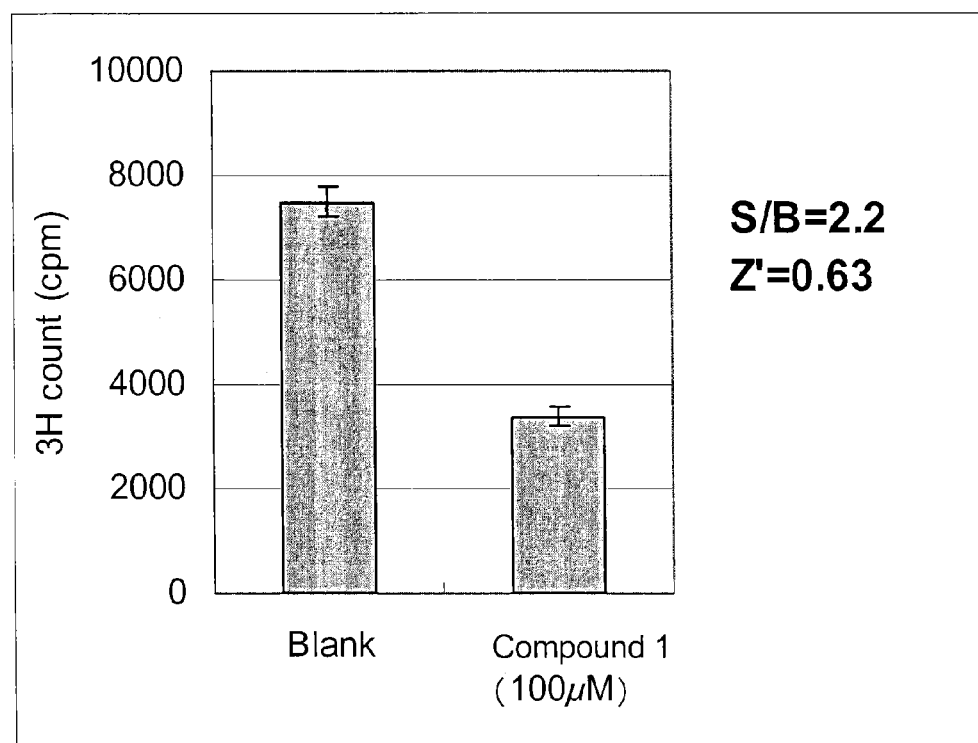
FIG. 11 is a graph showing the results of performance evaluation of a Gβγ2-Myc-binding screening system.

Furthermore, the stability of the screening system using the Gβγ2-Myc was examined by calculating the average value, standard deviation, and Z' value (n=6) in both the case of using the Compound 1 (100 μM) as a test substance and the case of not using the test substance. As a result, the Z' value was 0.63, remarkably larger than 0.5. When the Z' value is more than 0.5, high throughput screening (HTS) can be achieved (Non-Patent Document 16: Zhang et al., *Journal of Biomolecular Screening*, 4, 67, (1999)). Thus, it was clarified that the assay system could be practically used for the HTS (FIG. 11). The screening system can be used for screening a hypoglycemic effect.

Example 23

Measurement of Inhibitory Activity Against Compound 6-Induced Akt Phosphorylation by an Inhibitor Specific to Phosphoinositide 3-Kinase (PI3-Kinase) β and δ

TGX-115, reported as an inhibitor specific to phosphoinositide 3-kinase (PI3-kinase) β and δ by Knight et al. (*Bioorganic & Medicinal Chemistry*, 12, 4749, (2004)), was synthesized. The synthesis was carried out using a method described in a patent publication (Patent Document 5: WO 01/53266).

The inhibitory activity of the inhibitor TGX-115 specific to the phosphoinositide 3-kinase (PI3-kinase) β and δ against Compound 6-induced Akt phosphorylation was measured by using a differentiated 3T3L1 cell converted to a adipocyte as follows. The 3T3L1 cells were seeded in a Dulbecco MEM medium containing 10% fetal calf serum (FCS) in a 60-mm type I Collagen coated dish (IWAKI 4010-010) at a ratio of $1.5 \times 10^4$ cells/dish, cultured therein at 37° C. for 4 days in the presence of 5% $CO_2$, cultured for 2 days in a Dulbecco MEM medium containing 10 μg/ml of insulin (SIGMA 1-9278), 1 μM of dexamethasone (nacalai tesque 109-31), 0.5 mM of IBMX (WAKO 099-03411), and 10% FCS, cultured for 2 days in a Dulbecco MEM medium containing 10 μg/ml of insulin (SIGMA 1-9278) and 10% FCS, and further cultured for 4 days in a Dulbecco MEM medium containing 10% FCS, to obtain the differentiated 3T3L1 cells. The differentiated 3T3L1 cells were seeded in a Dulbecco MEM medium containing 10% FCS in a 96-well plate (Collagen type I coated plate, IWAKI, Product No. 4860-010) at a ratio of $4 \times 10^4$ cells/well, cultured at 37° C. for about 16 hours in the presence of 5% $CO_2$ to achieve sufficient attachment, and the medium was removed by suction. The cells were further cultured for 6 hours in a Dulbecco MEM medium containing 0.1% BSA without serum. The medium was removed by suction, 90 μl of a 0.1% BSA/Dulbecco MEM medium containing TGX-115 was added to the plate, and a pretreatment was carried out at 37° C. for 15 minutes in the presence of 5% $CO_2$. Then, 10 μl of a 0.1% BSA/Dulbecco MEM medium containing 3 mM of Compound 6 was added thereto, and a treatment was carried out at 37° C. for 10 minutes in the presence of 5% $CO_2$. The 96-well plate was placed on ice, the medium was removed by suction, a lysis buffer (containing 1 mM of PMSF) at ice temperature was added to the plate, and the resultant was frozen at −80° C. The lysis buffer was prepared in accordance with the attached package insert of a phosphorylated Akt measurement kit (Cell Signaling Technologies, Product No. 7160, PathScanR Phospho-Akt1 (Ser473) Sandwich ELISA Kit). The frozen 96-well plate was returned to room temperature to thaw the extract solution (the lysate), and the phosphorylated Akt amount was measured using the phosphorylated Akt measurement kit in accordance with the package insert.

Figure 12:
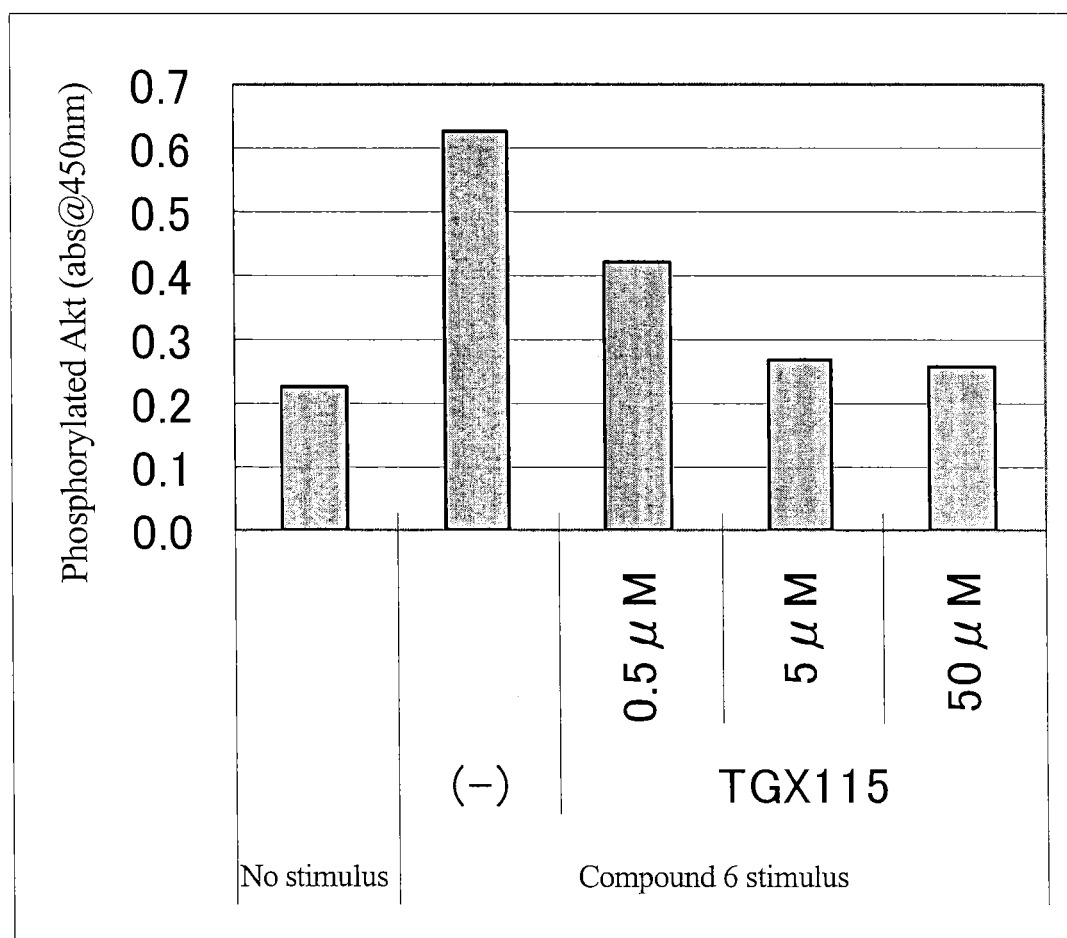
FIG. 12 is a graph showing the inhibition of Compound 6-induced Akt phosphorylation by an inhibitor TGX-115 specific to phosphoinositide 3-kinase (PI3-kinase) β and δ in a differentiated 3T3-L1 adipocyte.

As shown in FIG. 12, the Akt phosphorylation by Compound 6 was clearly inhibited by the inhibitor TGX-115 specific to the phosphoinositide 3-kinase (PI3-kinase) β and δ. Thus, it was strongly suggested that the phosphoinositide 3-kinase (PI3-kinase) β or δ was involved in the Akt phosphorylation and glucose uptake actions of Compound 6.

Example 24

Examination of the Effect of Compounds on Phosphoinositide 3-Kinase (PI3-Kinase) Activity in the Presence of Gβ1γ2-Myc (1) Purification of Gβ1γ2-Myc Using MonoQ Column and Gel Filtration After thawing the frozen insect cell Sf21 expressing the Gβ1, Myc-Gγ2, and Gαi1-His prepared in Example 19 (8), $2.5 \times 10^8$ cells were suspended in 4 ml of a lysis buffer (50 mM HEPES (pH 8.0), 3 mM $MgCl_2$, 10 mM 2-mercaptoethanol, 10 μM GDP, a protease inhibitor cocktail (Rosch Diagnostics, 11-697-498-001), 1 mM EDTA, 100 mM NaCl), and centrifuged (100000 g, 20 minutes) to obtain a pellet. The pellet was suspended in 2 ml of an extraction buffer (50 mM HEPES (pH 8.0), 3 mM $MgCl_2$, 10 mM 2-mercaptoethanol, 10 μM GDP, a protease inhibitor cocktail, 50 mM NaCl, 1% sodium cholate). The suspension was stirred at 4° C. for 1 hour, and subjected to centrifugation (100000 G; 20 minutes), whereby the supernatant was obtained as an extract solution (2 ml). 16 ml of Buffer A (50 mM HEPES (pH 8.0), 3 mM $MgCl_2$, 10 mM 2-mercaptoethanol, 10 μM GDP, a protease inhibitor cocktail, 100 mM NaCl, 0.5% Lubrol) was added to the extract solution (2 ml).

Half the amount of the above solution (10 ml) was adsorbed to the MonoQ (diameter 5 mm, length 100 mm, Amersham Biosciences) at a flow rate of 1 ml/minute. Buffer A (50 mM HEPES (pH 8.0), 0.2 mM 2-mercaptoethanol, 0.2% sodium cholate, 90 mM NaCl) and Buffer B (50 mM HEPES (pH 8.0), 0.2 mM 2-mercaptoethanol, 0.2% sodium cholate, 1 M NaCl) were used as eluants of the MonoQ, and after sufficiently equilibrated by Buffer A, the solution was adsorbed thereto. After the adsorption, the column was washed with Buffer A at 1 ml/minute for about 12 minutes, and eluted under an NaCl concentration gradient (0% to 50% B/20 minutes, 50% to 100% B/5 minutes, 100% B/2 minutes). The eluate fractions were collected every 1 minute after the start of the gradient elution. Each fraction was measured with respect to the binding of the $^3$H-labeled Compound 1 by the SPA method described in Example 21. The fraction Nos. 12 to 15 having high activity were collected, the Gβ therein was detected by a Western blot method using an anti-Gβ antibody (Upstate Biotechnologies, Product No. 06-238), and thus it was confirmed that the Gβ was eluted in the fractions.

The fraction Nos. 12 to 15 were further purified by a gel filtration chromatography. The fractions (4 ml) was concentrated into about 1 ml by ultrafiltration using Centricon-10, and subjected to a gel filtration using Superose 6 10/30 (diameter 10 mm, length 300 mm, Amersham Biosciences). A buffer containing 40 mM of HEPES-Na (pH 7.4), 120 mM of NaCl, 1 mM of EGTA, 2 mM of 2-mercaptoethanol, and 0.2% of sodium cholate was used as the eluent. The gel filtration was carried out at a flow rate of 0.5 ml/minute, and the fractions were collected every 2 minutes immediately after the start of the gel filtration. Each fraction was subjected to the binding activity measurement of the $^3$H-labeled Compound 1 by the SPA method described in Example 21 and a Western blot using an anti-Gβ antibody (Upstate, Product No. 06-238). Thus, the binding activity of the $^3$H-labeled Compound 1 and the Gβ content were observed in the fraction No. 16 (hereinafter referred to as Fr. 16, 1 ml). The Gβ concentration in the Fr. 16 was about 10 μg/ml, which was measured by using a commercially available Gβγ standard (a pure bovine brain-derived product, Calbiochem, Product No. 371768) in the same Western blot method. Thus obtained product is hereinafter referred to as the purified Gβ1γ2-Myc.

(2) Examination of Effects of N-Deacetylcolchicine and Compound 1 on Activity of Subtype (α, β, γ, δ) of Phosphoinositide 3-Kinase (PI3-Kinase) in the Presence of Gβ1γ2-Myc The effects of N-deacetylcolchicine and Compound 1 on the activity of each PI3-kinase subtype (α, β, γ, or δ) in the presence of the Gβ1γ2-Myc were examined using the purified Gβ1γ2-Myc obtained in (1) based on a method reported by Maier et al. (Non-Patent Document 4) and Kerchner et al. (Non-Patent Document 10). The subtypes α (PI3 Kinase (p110α/p85α), active, Upstate, Product No. 14-602), β (PI3 Kinase (p110β/p85α), active, Upstate, Product No. 14-603), γ ((PI3KγHis-GST (Phosphoinositide 3-kinase p110γHis/p101GST) human, Recombinant, Sf9 insect cell, JENA Bioscience, Product No. PR-347S), and δ (PI3 Kinase (p110δ/p85α), active, Upstate, Product No. 14-604) were used as the PI3-kinase subtypes respectively. A PI3K buffer (40 mM HEPES-Na (pH 7.4), 120 mM NaCl, 1 mM EGTA, 1 mM dithiothreitol, 1 mM β glycerophosphoric acid, 10 mM $MgCl_2$, 0.1% BSA) was used as a buffer in the following reactions.

A mixture liquid of phosphatidylethanolamine (0.256 µmol), phosphatidylserine (0.24 µmol), phosphatidylcholine (0.112 µmol), sphingomyelin (0.024 µmol), and phosphatidylinositol-[4,5]-bisphosphate (0.032 µmol) was added to a glass tube and dried by argon gas, and to this was added the PI3K buffer (0.27 ml) at ice temperature. This solution was ultrasonic-treated in ice to prepare a lipid micelle solution. To the lipid micelle solution (125 µl) was added the purified Gβ1γ2-Myc solution (250 µl, 10 µg/ml) obtained in (1), and the resultant solution was stirred and left in ice for 10 minutes. 30 µl of the lipid micelle solution containing the Gβ1γ2-Myc was dispensed into 1.5-ml microtubes, and to these were added 5 µl of a compound solution and 5 µl of each PI3-kinase subtype (α, β, and δ: 5 µg/ml, γ: 2.5 µg/ml) successively. The mixture was left at room temperature for 10 minutes, and a 40-µM ATP solution (10 µl) containing $^{32}$P-γ-ATP was added thereto, to initiate a reaction. The amount of the $^{32}$P-γ-ATP added was about 300 kBq per one reaction. The reaction was carried out at room temperature for 30 minutes, and stopped by adding 80 µl of 1N HCl at ice temperature. 300 µl of a chloroform:methanol (1:1) solution was added thereto, the mixture was stirred to extract the lipid, and the organic layer was washed with 80 µl of 1N HCl twice. The solvent was removed from the residual organic layer under reduced pressure, the residue was dissolved in 20 µl of a chloroform: methanol (4:1) solution, the entire solution was spotted on a TLC plate (Merck, Kieselgel 60), and a TLC was carried out for about 4 hours using a developer of acetic acid:water:1-propanol (4:31:65). The TLC plate was treated with oxalic acid beforehand such that the plate was sufficiently developed by a 40% methanol solution containing 1% of potassium oxalate, dried overnight, and activated at 110° C. for 30 minutes. After the developing, the TLC plate was sufficiently dried and exposed using an imaging plate, and data were obtained by BAS2000 (FUJIFILM Corporation). The data were analyzed by a software of BAS2000, the analysis region was controlled such that spots of phosphatidylinositol-[3,4,5]-trisphosphate (PIP3) in the TLC lanes have the same areas, and the energy (PSL) corresponding to each radioactivity was quantified in the region.

Figure 13:
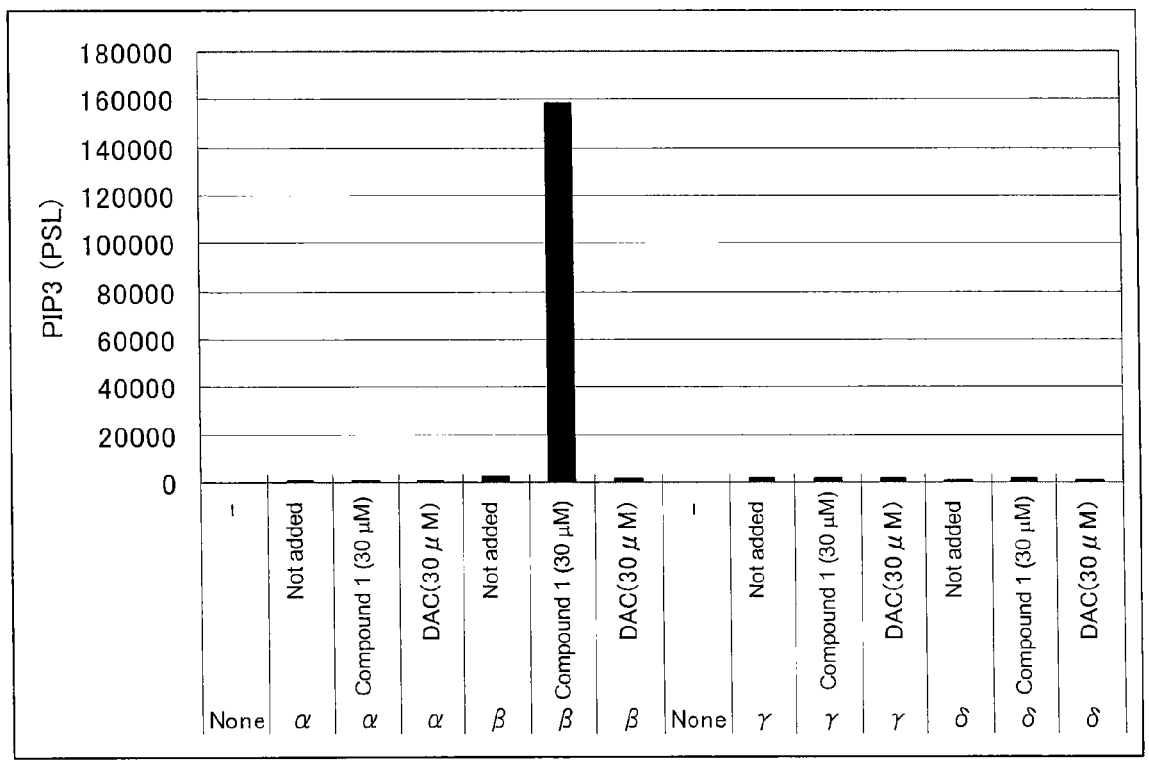
FIG. 13 is a graph showing the effects of N-deacetylcolchicine (DAC) and Compound 1 on the activity of each subtype (α, β, γ, or δ) of phosphoinositide 3-kinase (PI3-kinase) in the presence of Gβ1γ2-Myc.
Figure 1:
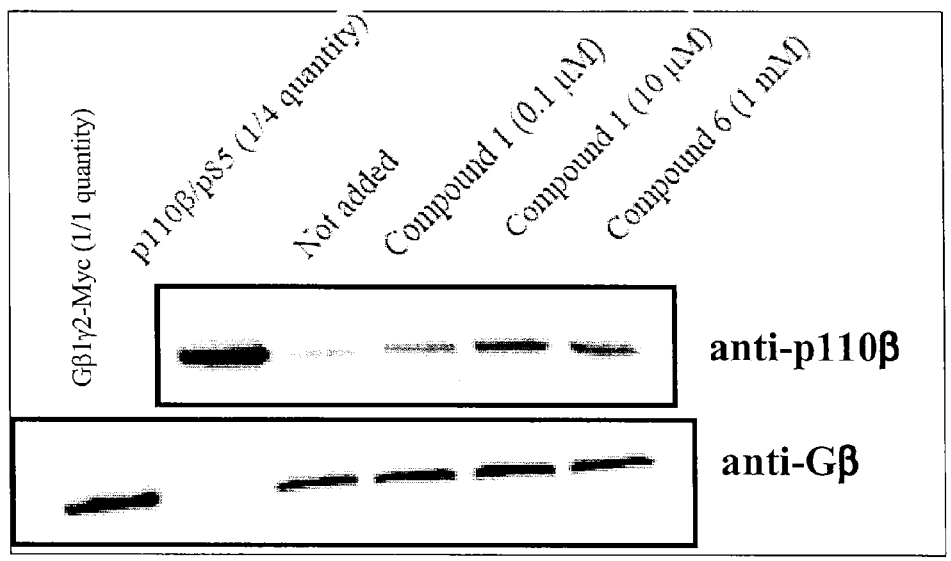
Figure 1:
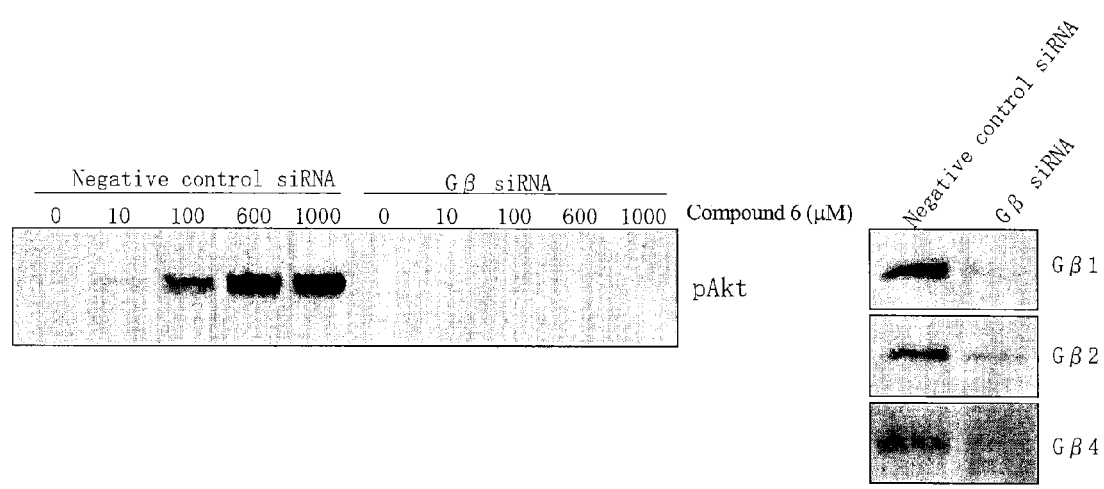

As shown in FIG. 13, Compound 1 (30 µM) had a significant activating effect only on the PI3-kinase β, while the N-deacetylcolchicine (DAC, 30 µM) had no effects on the activities of all the PI3-kinase subtypes.

(3) Measurement of Effect of Compounds 1 and 6 on Enhancing Activity of PI3-Kinase β

Based on the results of (2), the following research was made to examine whether the activation of the PI3-kinase β by Compound 1 depended on the Gβ (Gβ1γ2-Myc), and whether also a Gβ binding substance other than Compound 1 had the same activity.

A lipid micelle solution was prepared in the same manner as (2). To the lipid micelle solution (100 µl) were added the purified Gβ1γ2-Myc solution obtained in (1) (200 µl, 10 µg/ml) or the same buffer without the Gβ1γ2-Myc (100 µl), and the mixture was left in ice for 10 minutes. 30 µl of the lipid micelle solution with or without the Gβ1γ2-Myc was added to a 1.5-ml microtube, and 5 µl of the compound solution and 5 µl of the PI3-kinase β (5 µg/ml) were successively added thereto, and the mixture was left at room temperature for 10 minutes. To the solution was added a 40-µM ATP solution (10 µl) containing $^{32}$P-γ-ATP to initiate the reaction. The amount of the $^{32}$P-γ-ATP added was about 370 kBq per one reaction. The reaction was carried out at room temperature for 15 minutes, the resultant was treated in the same manner as (2), and the amount of the produced PIP3 was measured.

As shown in FIG. 14, Compound 1 had no effects on the PI3-kinase β in the absence of the Gβ (Gβ1γ2-Myc), but it had a significant effect of enhancing the enzymatic activity of the PI3-kinase β in the presence of the Gβ (Gβ1γ2-Myc) in a concentration-dependent manner (0.1, 1, and 10 µM). Also Compound 6 had a significant effect of enhancing the enzymatic activity of the PI3-kinase β in the presence of the Gβ (Gβ1γ2-Myc) in a concentration-dependent manner (100 µM and 1 mM). Thus, it was considered that all the compounds found to be bound to the Gβ in Examples 20 and 22 were effective for enhancing the PI3-kinase β activity in the presence of the Gβ, and thereby had the glucose uptake activity described in Example 11 and the Akt phosphorylation activity described in Example 13 depending on the binding strength.

A hypoglycemic material can be screened such that an appropriate test substance is used instead of Compounds 1 and 6 in the above process, and the effect of enhancing the enzymatic activity is detected.

Example 25

Examination of Effect of Compounds 1 and 6 Against Binding of Gβ1γ2-Myc to Phosphoinositide 3-kinase (PI3-kinase) β

300 µl of a PI3K buffer (40 mM HEPES-Na (pH 7.4), 120 mM NaCl, 1 mM EGTA, 1 mM dithiothreitol, 1 mM β glycerophosphoric acid, 10 mM $MgCl_2$, 0.1% BSA) was added to a 1.5-ml microtube, and to this were added 200 ng of the Gβ1γ2-Myc obtained in Example 20 (1), 160 ng of PI3-kinase β (PI3 Kinase (p110β/p85α), active, Upstate, Product No. 14-603), and a test substance. The mixture was left at room temperature for 30 minutes, to this was added 10 µl of a solution of an anti-cMyc antibody (9E10, 200 µg/ml, SantaCruz, Product No. sc-40), and the resulting mixture was left at room temperature for 2 hours. To the solution was added 25 µl of anti-mouse IgG agarose beads (American Qualex, Product No. 61060) which were washed with the same buffer, stirred at room temperature for 1 hour and centrifuged (10000 rpm, 1 minute) to remove the supernatant. Furthermore, the beads were washed with 0.5 ml of the buffer 3 times, eluted in a boiling SDS-containing buffer, and subjected to an SDS polyacrylamide electrophoresis. Then, the amounts of the p110β and the Gβ adsorbed to the beads were measured by a Western blot method using an anti-p110β antibody (SantaCruz, Product No. sc-602) and an anti-Gβ antibody (SantaCruz, Product No. sc-261).

As shown in FIG. 15, the amount of the Gβ directly bound to the anti-cMyc antibody was approximately constant, while the p110β amount was increased by the presence of Compound 1 and 6. Thus, it was confirmed that the binding between the Gβ and the p110β (PI3-kinase β) was enhanced by Compounds 1 and 6. In addition, Compound 1 (0.1 μM) and Compound 6 (1 mM), which had approximately the same effect of enhancing the PI3-kinase β activity in the presence of the Gβ1γ2-Myc as described in Example 20 (2), had approximately the same effect of enhancing the binding between the Gβ and the p110β (PI3-kinase β), so that it was suggested that the PI3-kinase β activity was enhanced in the presence of the Gβ1γ2-Myc due to the increase of the binding between the Gβ and the p110β (PI3-kinase β) by each compound.

A hypoglycemic material can be screened such that an appropriate test substance is used instead of Compounds 1 and 6 in the above process, and the effect of enhancing the binding between the Gβ and the p110β (PI3-kinase β) is detected.

Example 26

Evaluation of Akt Phosphorylation Activity in Gβ Expression Inhibited Cell

The effect of Gβ expression inhibition by a siRNA method against the Akt phosphorylation activity of Compound 6 in a human liver-derived HLF cell was evaluated as follows.

The HLF cells were seeded in a Dulbecco MEM medium containing 10% FCS in a 24-well dish (IWAKI, Product No. 3820-024) at a ratio of $3.75 \times 10^4$ cells/well. The cells were cultured at 37° C. for 6 hours in the presence of 5% $CO_2$ to achieve sufficient attachment, a siRNA was transfected into the cells at the concentration of 100 nM using Dharmafect 2 (Dharmacon, Product No. T-2002-02), and the resultant cells were cultured at 37° C. for 48 hours in the presence of 5% $CO_2$. Used as the siRNA was a negative control siRNA (Sense: UUCUCCGAACGUGUCACGUdTdT (SEQ ID NO. 37), Antisense: ACGUGACACGUUCGGAGAAdTdT (SEQ ID NO. 38), Qiagen, Product No. 1027310) or a Gβ siRNA containing the same amounts of a Gβ1 siRNA (Sense: GAUCAUUGUUGCACACAAAdTdT (SEQ ID NO. 39), Antisense: UUUGUGUGCAACAAUGAUCdTdG (SEQ ID NO. 40), Qiagen, Product No. SI00428841), a Gβ2 siRNA (Sense: GCCAUGAAUCCGACAUCAAdTdT (SEQ ID NO. 41), Antisense: UUGAUGUCGGAUUCAUGGCdCdG (SEQ ID NO. 42), Qiagen, Product No. SI00428848), and a Gβ4 siRNA (Sense: CCUUAUAUUUGCAGGUGAAdTdT (SEQ ID NO. 43), Antisense: UUCACCUG-CAAAUAUAAGGdTdA (SEQ ID NO. 44), Qiagen, Product No. SI00130746). 48 hours after the siRNA transfection, the medium was replaced by 0.5 ml of a Dulbecco MEM medium containing 10% FCS, the cells were cultured at 37° C. for 20 hours in the presence of 5% $CO_2$, the medium was replaced by 0.5 ml of a Dulbecco MEM medium containing 0.1% BSA, the cells were cultured at 37° C. for 4 hours in the presence of 5% $CO_2$, the medium was replaced by 0.5 ml of a Dulbecco MEM medium containing Compound 6 and 0.1% BSA, and the cells were treated with the medium at 37° C. for 20 minutes in the presence of 5% $CO_2$. Then, the resultant was washed with 0.5 ml of PBS, suspended in 100 μl of a lysis buffer (Cell Signaling Technologies, Product No. 9803, containing 1 mM of PMSF), subjected to ultrasonic homogenization, and centrifuged (14000 rpm, 10 minutes), and the supernatant was obtained as an extract solution. Each of thus obtained extract solution was subjected to protein concentration determination using a protein assay (BioRad, Product No. 500-0006) and BSA as standard, and the protein concentration of the liquids were controlled to the same value. Each solution was subjected to an SDS polyacrylamide electrophoresis, and the phosphorylated Akt amount, the Gβ1 amount, the Gβ2 amount, and the Gβ4 amount were measured by a Western blot method using an anti-phosphorylated Akt antibody (Cell Signaling Technologies, Product No. 9271), an anti-Gβ1 antibody (SantaCruz, Product No. sc-379), an anti-Gβ2 antibody (SantaCruz, Product No. sc-380), and an anti-Gβ4 antibody (SantaCruz, Product No. sc-382). As shown in FIG. 16, the phosphorylated Akt amount was increased depending on the Compound 6 concentration in the case of introducing the negative control siRNA, while the phosphorylated Akt was not detected at any Compound 6 concentration in the case of introducing the Gβ siRNA to inhibit the Gβ expression. Thus, it was clarified that the Akt phosphorylation was caused by Compound 6 via the Gβ.

Example 27

Method for Screening Hypoglycemic Substance by Activating Phosphoinositide 3-Kinase (PI3-Kinase) β in Presence of Gβ1γ2-His (1) Preparation of G Protein βγ (Gβ1γ2-His)

A Gβ1 expression system using an insect cell was prepared in the same manner as Example 19 (2). A 6×His-Gγ$_2$ expression system using an insect cell was constructed as follows.

A PCR was carried out by a common technique using a primer of a synthetic DNA of SEQ ID NOs. 45 and 46 and a template of a cDNA clone containing the entire human Gγ2 protein-encoding domain. The obtained 0.3-kbp DNA was subcloned into a vector pCR4Blunt-TOPO (Invitrogen Corporation, Product No. K2875), and a base sequence of SEQ ID NO. 47 (an amino acid sequence of SEQ ID NO. 48) was observed. The resultant was cut by restriction enzymes EcoRI and XhoI, and inserted into the restriction enzyme sites in a vector pFastBac1 of a Bac-to-Bac baculovirus expression system (Invitrogen Corporation, Cat No. 10359-016), whereby a pFB1-6×His-GNG2 was constructed. Furthermore, a bacmid DNA was prepared from a cultured medium of a transformed Escherichia coli DH10Bac strain in accordance with the attached manual. The bacmid DNA was transfected into a silkworm cell line Sf-21 by a lipofection method, to obtain a recombinant virus capable of expressing the 6×His-Gγ$_2$. The Sf-21 cell was further infected with the virus in accordance with the manual, whereby the virus titer was increased such that a desired amount of the recombinant protein could be obtained. The expression of the desired recombinant protein was detected by a Western blot method using an antibody specific to a 6×His tag sequence in the virus-infected cell lysate.

Production of the Gβ1γ2-His was carried out in the insect cell as follows. Expression and production of the Gβ1γ2-His protein in the insect cell line Sf21 was carried out using the above bacmid DNA containing the Gβ1 or Gγ1-His gene in accordance with the attached manual (Instruction Manual) of the Bac-to-Bac baculovirus protein expression system (Invitrogen Corporation, Product No. 10359-016). Specifically, the baculovirus having the Gβ1 or Gγ1-His gene was incubated at 28° C. for 65 hours under shaking in an SF900IISFM medium (Invitrogen, Product No. 10902-096) having a level of $10^8$ cells/100 ml in a 250-ml conical flask to obtain an MOI of 2 or more. After the incubation, the cell was collected by centrifugation (1000 rpm, 5 minutes) and washed with Insect Cell PBS (7.3 mM $NaH_2PO_4$ (pH 6.2), 58 mM KCl, 47 mM NaCl, 5 mM $CaCl_2$). The cell was collected by further centrifugation (1000 rpm, 5 minutes) and stored in the frozen state.

The Gβ1γ2-His was prepared as follows. Using the above obtained cells, $2.5 \times 10^8$ cells were suspended in 10 ml of a lysis buffer (20 mM HEPES (pH 8.0), 150 mM NaCl, 5 mM 2-mercaptoethanol, a protease inhibitor cocktail (Rosch Diagnostics, 11-697-498-001), 1 mM EDTA), and the suspension was subjected to ultrasonic homogenization and centrifugation (2600 G, 10 minutes) to obtain 12 ml of the supernatant. 3 ml of 5% Lubrol was added to the supernatant, and the resultant 1% Lubrol was stirred at 4° C. for 1 hour and centrifuged (100000 G, 20 minutes), whereby 15 ml of the supernatant was obtained as an extract solution. The extract solution was applied to a column containing 500 µl of an Ni-NTA agarose (QIAGEN, Product No. 30210), washed with 1 ml of a lysis buffer containing 1% of Lubrol, 2 ml of Washing buffer 1 (20 mM HEPES (pH 8.0), 0.4M NaCl, 5 mM 2-mercaptoethanol, 0.5% Lubrol, 0.15% sodium cholate, 10 mM imidazole), 2 ml of Washing buffer 2 (20 mM HEPES (pH 8.0), 0.1 M NaCl, 5 mM 2-mercaptoethanol, 0.25% Lubrol, 0.3% sodium cholate, 10 mM imidazole), and 1 ml of Washing buffer 3 (20 mM HEPES (pH 8.0), 0.1 M NaCl, 5 mM 2-mercaptoethanol, 0.5% sodium cholate, 10 mM imidazole), and eluted with 1 ml of an elution buffer (20 mM HEPES (pH 8.0), 0.01 M NaCl, 5 mM 2-mercaptoethanol, 1% sodium cholate, 50 mM imidazole). The obtained eluate was used as a Gβ1γ2-His solution. The concentration of the Gβ1γ2-His protein was about 100 µg/ml, which was measured by a Western blot method using a commercially available Gβγ standard (a pure bovine brain-derived product, Calbiochem, Product No. 371768). Thus obtained product is hereinafter referred to as the purified Gβ1γ2-His.

(2) Phosphoinositide 3-Kinase (PI3-Kinase) β Activation Assay in the Presence of Gβ1γ2-His A lipid micelle solution was prepared in accordance with a method described in Example 24 (2), to this was added the Gβ1γ2-His prepared in (1) at a concentration of 13.3 µg/ml, and the mixture was left on ice for 10 minutes. To 30 µl of the resultant solution were added 5 µl of a solution containing Compound 1 or 6 and 5 µl of a PI3-kinase β solution (5 µg/ml) successively. A 40 µM ATP solution (10 µl) containing $^{32}$P-γ-ATP was added thereto, and a reaction was carried out at room temperature for 2 hours. The reaction was stopped by addition of 80 µl of 1N HCl, and the lipid was extracted with 300 µl of chloroform:methanol (1:1). The organic layer was washed with 80 µl of 1N HCl twice, 10 ml of a liquid scintillator (Hionic Fluor) was added thereto, and the $^{33}$P was measured by a liquid scintillation counter.

Figure 17:
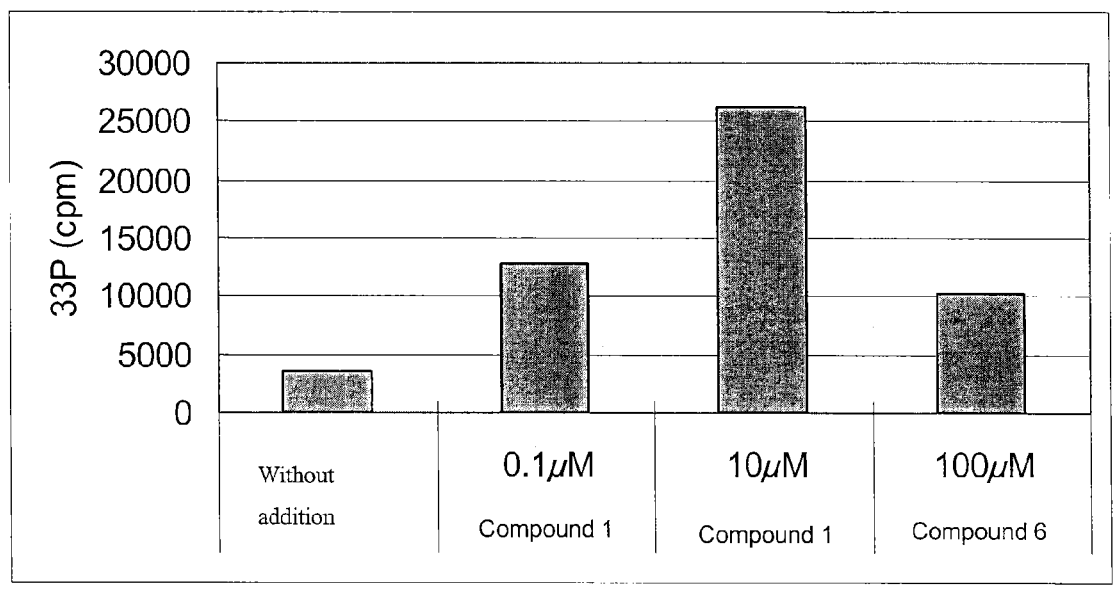
FIG. 17 is a graph showing the effects of Compounds 1 and 6 on enhancing the PI3-kinase β activity in a screening method described in Example 27.

As shown in FIG. 17, the PI3-kinase activity was clearly increased by the addition of Compound 1 (0.1 µM, 10 µM) or Compound 6 (100 µM) as compared with the case without compound. It was clarified that this method could be used as a screening system.

Thus, a hypoglycemic material can be screened by the screening system using this method.

INDUSTRIAL APPLICABILITY

In the present invention, there are provided the compound and the antidiabetic agent having the hypoglycemic effect, the method for screening the compound or the antidiabetic agent, the probe compound usable in the screening method, etc.

The invention claimed is:
1. A compound represented by general formula (I) or a pharmaceutically acceptable salt thereof:

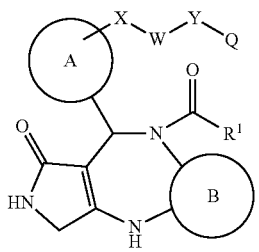

General Formula (I)

wherein
in the general formula (I), A and B may be the same or different and independently represent an optionally substituted aromatic ring, an optionally substituted heterocyclic ring, or an optionally substituted aliphatic ring;
$R^1$ represents a lower alkyl group, a lower alkenyl group, a lower alkynyl group, or a lower alkoxy group, the groups being optionally substituted by 1 to 3 substituents;
—X— and —Y— may be the same or different and independently represent a hydrogen atom, —O—, —$NR^2$—, —S—, —SO—, —$SO_2$—, —$CH_2$—, —$CR^3R^4$—, —COO—, —$CONR^2$—, or —CO—, in which $R^2$ represents a hydrogen atom, an optionally substituted lower alkyl group, an optionally substituted acyl group, an optionally substituted alkoxycarbonyl group, an optionally substituted carbamoyl group, or an optionally substituted sulfonyl group, and $R^3$ and $R^4$ may be the same or different and independently represent a hydrogen atom, a halogen atom, a hydroxyl group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, or a trifluoromethyl group;
—W— represents an optionally substituted alkyl chain having 1 to 20 carbon atoms, and 1 to 10 carbon atoms in the alkyl chain may be replaced by —O—, —$NR^5$—, —S—, —SO—, —$SO_2$—, or —CO—, in which $R^5$ represents a hydrogen atom, an optionally substituted lower alkyl group, an optionally substituted acyl group, an optionally substituted alkoxycarbonyl group, an optionally substituted carbamoyl group, or an optionally substituted sulfonyl group;
Q represents a hydrogen atom, biotin, a fluorophore, a chromophore, a chemiluminescent functional group, an enzyme, a solid phase, a diazo group, or an azido group;
one or more atoms in the formula may be (a) radioisotope(s);
with the proviso that:
i) in the optionally substituted groups, each substituent is selected from the group consisting of halogen atoms, a hydroxyl group, alkyl groups, mercapto groups, alkoxy groups, alkylthio groups, alkylsulfonyl groups, acyl groups, acyloxy groups, amino groups, alkylamino groups, a carboxyl group, alkoxycarbonyl groups, carbamoyl groups, a nitro group, a cyano group, a trifluoromethyl group, aryl groups, heteroaryl groups, diazo groups, and azido groups, and the substituent may be labeled with biotin, a fluorophore, a chromophore, a chemiluminescent moiety, or an enzyme;
ii) when —X— is a hydrogen atom, —W—, —Y—, and Q do not exist;
iii) when —Y— is a hydrogen atom, Q does not exist; and
iv) the compound of the general formula (I) satisfies at least one of the following conditions a) to f):
a) —X— and —Y— are other than a hydrogen atom, and Q is biotin, a fluorophore, a chromophore, a chemiluminescent functional group, or an enzyme;
b) —X— and —Y— are other than a hydrogen atom, and Q is a diazo group or an azido group;
c) —X— and —Y— are other than a hydrogen atom, and Q is a solid phase;
d) labeled with at least one radioisotope atom;
e) substituted with at least one substituent which is labeled with biotin, a fluorophore, a chromophore, a chemiluminescent moiety, or an enzyme; or
f) substituted with at least one diazo group or azido group as a substituent.

2. A compound or a pharmaceutically acceptable salt thereof according to claim 1, wherein —X— and —Y— are other than a hydrogen atom, and Q is biotin, a fluorophore, a chromophore, a chemiluminescent functional group, or an enzyme.

3. A compound or a pharmaceutically acceptable salt thereof according to claim 2, wherein each substituent in the optionally substituted groups is not labeled with biotin, a fluorophore, a chromophore, a chemiluminescent moiety, or an enzyme.

4. A compound or a pharmaceutically acceptable salt thereof according to claim 1, wherein —X— and —Y— are other than a hydrogen atom, and Q is a diazo group or an azido group.

5. A compound or a pharmaceutically acceptable salt thereof according to claim 4, wherein each substituent in the optionally substituted groups is not labeled with biotin, a fluorophore, a chromophore, a chemiluminescent moiety, or an enzyme.

6. A compound or a pharmaceutically acceptable salt thereof according to claim 1, wherein —X— and —Y— are other than a hydrogen atom, and Q is a solid phase.

7. A compound or a pharmaceutically acceptable salt thereof according to claim 1, wherein at least one atom in the general formula (I) is a radioisotope.

8. A compound or a pharmaceutically acceptable salt thereof according to claim 7, wherein X is a hydrogen atom.

9. A compound or a pharmaceutically acceptable salt thereof according to claim 1, wherein the compound has at least one substituent which is labeled with biotin, a fluorophore, a chromophore, a chemiluminescent moiety, or an enzyme.

10. A compound or a pharmaceutically acceptable salt thereof according to claim 1, wherein the compound has at least one diazo group or azido group as a substituent.

* * * * *

SEQUENCE LISTING

```
<160> NUMBER OF SEQ ID NOS: 48

<210> SEQ ID NO 1
<211> LENGTH: 28
<212> TYPE: DNA
<213> ORGANISM: Artificial Sequence
<220> FEATURE:
<223> OTHER INFORMATION: Primer

<400> SEQUENCE: 1
ggaagcttaa gatcggaaga tgagtgag                                     28

<210> SEQ ID NO 2
<211> LENGTH: 28
<212> TYPE: DNA
<213> ORGANISM: Artificial Sequence
<220> FEATURE:
<223> OTHER INFORMATION: Primer

<400> SEQUENCE: 2
gggctcgagg gcgttagttc cagatctt                                     28

<210> SEQ ID NO 3
<211> LENGTH: 1056
<212> TYPE: DNA
<213> ORGANISM: Homo sapiens

<400> SEQUENCE: 3
gggaagctta agatcggaag atgagtgagc ttgaccagtt acggcaggag gccgagcaac      60
ttaagaacca gattcgagac gccaggaaag catgtgcaga tgcaactctc tctcagatca     120
caaacaacat cgacccagtg ggaagaatcc aaatgcgcac gaggaggaca ctgcgggggc     180
acctggccaa gatctacgcc atgcactggg gcacagactc caggcttctc gtcagtgcct     240
cgcaggatgg taaacttatc atctgggaca gctacaccac caacaaggtc cacgccatcc     300
ctctgcgctc ctcctgggtc atgacctgtg catatgcccc ttctgggaac tatgtggcct     360
```

```
gcggtggcct ggataacatt tgctccattt acaatctgaa aactcgtgag gggaacgtgc    420
gcgtgagtcg tgagctggca ggacacacag gttacctgtc ctgctgccga ttcctggatg    480
acaatcagat cgtcaccagc tctggagaca ccacgtgtgc cctgtgggac atcgagaccg    540
gccagcagac gaccacgttt accggacaca ctggagatgt catgagcctt tctcttgctc    600
ctgacaccag actgttcgtc tctggtgctt gtgatgcttc agccaaactc tgggatgtgc    660
gagaaggcat gtgccggcag accttcactg gccacgagtc tgacatcaat gccatttgct    720
tctttccaaa tggcaatgca tttgccactg gctcagacga cgccacctgc aggctgtttg    780
accttcgtgc tgaccaggag ctcatgactt actcccatga caacatcatc tgcgggatca    840
cctctgtctc cttctccaag agcgggcgcc tcctccttgc tgggtacgac gacttcaact    900
gcaacgtctg ggatgcactc aaagccgacc gggcaggtgt cttggctggg catgacaacc    960
gcgtcagctg cctgggcgtg actgacgatg gcatggctgt ggcgacaggg tcctgggata   1020
gcttcctcaa gatctggaac taacgccctc gagccc                              1056

<210> SEQ ID NO 4
<211> LENGTH: 340
<212> TYPE: PRT
<213> ORGANISM: Homo sapiens

<400> SEQUENCE: 4

Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
    130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
    210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255
```

```
Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
            275                 280                 285

Tyr Asp Asp Phe Asn Cys Asn Val Trp Asp Ala Leu Lys Ala Asp Arg
            290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
aagaattcac catggccagc aacaacacc                                     29

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
ttctcgagtt aaaggatggc acagaaaaac ttc                                33

<210> SEQ ID NO 7
<211> LENGTH: 255
<212> TYPE: DNA
<213> ORGANISM: Homo sapiens

<400> SEQUENCE: 7
aagaattcac catggccagc aacaacaccg ccaggccagc aacaacaccg ccagcatagc    60
acaagccagg aagctggtag agcagcttaa gatggaagcc aatatcgaca ggataaaggt   120
gtccaaggca gctgcagatt tgatggccta ctgtgaagca catgccaagg aagaccccct   180
cctgacccct gttccggctt cagaaaaccc gtttagggag aagaagtttt tctgtgccat   240
cctttaactc gagaa                                                    255

<210> SEQ ID NO 8
<211> LENGTH: 71
<212> TYPE: PRT
<213> ORGANISM: Homo sapiens

<400> SEQUENCE: 8

Met Ala Ser Asn Asn Thr Ala Ser Ile Ala Gln Ala Arg Lys Leu Val
1               5                   10                  15

Glu Gln Leu Lys Met Glu Ala Asn Ile Asp Arg Ile Lys Val Ser Lys
            20                  25                  30

Ala Ala Ala Asp Leu Met Ala Tyr Cys Glu Ala His Ala Lys Glu Asp
            35                  40                  45

Pro Leu Leu Thr Pro Val Pro Ala Ser Glu Asn Pro Phe Arg Glu Lys
```

```
                        50                  55                  60
Lys Phe Phe Cys Ala Ile Leu
 65                  70

<210> SEQ ID NO 9
<211> LENGTH: 60
<212> TYPE: DNA
<213> ORGANISM: Artificial Sequence
<220> FEATURE:
<223> OTHER INFORMATION: Primer

<400> SEQUENCE: 9 ggggatccg ccaccatggc ccatcaccat caccatcacg ccggctgcac gctgagcgcc       60

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gggctcgaga acttaaaaga gaccacaatc ttt                                   33

<210> SEQ ID NO 11
<211> LENGTH: 1115
<212> TYPE: DNA
<213> ORGANISM: Homo sapiens

<400> SEQUENCE: 11 ggggatccg ccaccatggc ccatcaccat caccatcacg ccggctgcac gctgagcgcc       60
gaggacaagg cggcggtgga gcggagtaag atgatcgacc gcaacctccg tgaggacggc     120
gagaaggcgg cgcgcgaggt caagctgctg ctgctcggtg ctggtgaatc tggtaaaagt     180
acaattgtga agcagatgaa aattatccat gaagctggtt attcagaaga ggagtgtaaa     240
caatacaaag cagtggtcta cagtaacacc atccagtcaa ttattgctat cattagggct     300
atggggaggt tgaagataga ctttggtgac tcagcccggg cggatgatgc acgccaactc     360
tttgtgctag ctggagctgc tgaagaaggc tttatgactg cagaacttgc tggagttata     420
aagagattgt ggaaagatag tggtgtacaa gcctgtttca acagatcccg agagtaccag     480
cttaatgatt ctgcagcata ctatttgaat gacttggaca gaatagctca accaaattac     540
atcccgactc aacaagatgt tctcagaact agagtgaaaa ctacaggaat tgttgaaacc     600 catttttactt tcaaagatct tcattttaaa atgtttgatg tgggaggtca gagatctgag     660
cggaagaagt ggattcattg cttcgaagga gtgacggcga tcatcttctg tgtagcactg     720
agtgactacg acctggttct agctgaagat gaagaaatga accgaatgca tgaaagcatg     780
aaattgtttg acagcatatg taacaacaag tggtttacag atacatccat tatacttttt     840
ctaaacaaga aggatctctt tgaagaaaaa atcaaaaaga gccctctcac tatatgctat     900
ccagaatatg caggatcaaa cacatatgaa gaggcagctg catatattca atgtcagttt     960
gaagacctca ataaaagaaa ggacacaaag gaaatataca cccacttcac atgtgccaca    1020
gatactaaga atgtgcagtt tgttttgat gctgtaacga atgtcatcat aaaaaataat     1080
ctaaaagatt gtggtctctt ttaagttctc gagcc                               1115

<210> SEQ ID NO 12
<211> LENGTH: 362
<212> TYPE: PRT
```

<213> ORGANISM: Homo sapiens

<400> SEQUENCE: 12

Met Ala His His His His His His Ala Gly Cys Thr Leu Ser Ala Glu
1               5                   10                  15

Asp Lys Ala Ala Val Glu Arg Ser Lys Met Ile Asp Arg Asn Leu Arg
            20                  25                  30

Glu Asp Gly Glu Lys Ala Ala Arg Glu Val Lys Leu Leu Leu Leu Gly
        35                  40                  45

Ala Gly Glu Ser Gly Lys Ser Thr Ile Val Lys Gln Met Lys Ile Ile
    50                  55                  60

His Glu Ala Gly Tyr Ser Glu Glu Cys Lys Gln Tyr Lys Ala Val Val
65                  70                  75                  80

Val Tyr Ser Asn Thr Ile Gln Ser Ile Ile Ala Ile Ile Arg Ala Met
                85                  90                  95

Gly Arg Leu Lys Ile Asp Phe Gly Asp Ser Ala Arg Ala Asp Asp Ala
            100                 105                 110

Arg Gln Leu Phe Val Leu Ala Gly Ala Ala Glu Glu Gly Phe Met Thr
        115                 120                 125

Ala Glu Leu Ala Gly Val Ile Lys Arg Leu Trp Lys Asp Ser Gly Val
    130                 135                 140

Gln Ala Cys Phe Asn Arg Ser Arg Glu Tyr Gln Leu Asn Asp Ser Ala
145                 150                 155                 160

Ala Tyr Tyr Leu Asn Asp Leu Asp Arg Ile Ala Gln Pro Asn Tyr Ile
                165                 170                 175

Pro Thr Gln Gln Asp Val Leu Arg Thr Arg Val Lys Thr Thr Gly Ile
            180                 185                 190

Val Glu Thr His Phe Thr Phe Lys Asp Leu His Phe Lys Met Phe Asp
        195                 200                 205

Val Gly Gly Gln Arg Ser Glu Arg Lys Lys Trp Ile His Cys Phe Glu
    210                 215                 220

Gly Val Thr Ala Ile Ile Phe Cys Val Ala Leu Ser Asp Tyr Asp Leu
225                 230                 235                 240

Val Leu Ala Glu Asp Glu Glu Met Asn Arg Met His Glu Ser Met Lys
                245                 250                 255

Leu Phe Asp Ser Ile Cys Asn Asn Lys Trp Phe Thr Asp Thr Ser Ile
            260                 265                 270

Ile Leu Phe Leu Asn Lys Lys Asp Leu Phe Glu Glu Lys Ile Lys Lys
        275                 280                 285

Ser Pro Leu Thr Ile Cys Tyr Pro Glu Tyr Ala Gly Ser Asn Thr Tyr
    290                 295                 300

Glu Glu Ala Ala Ala Tyr Ile Gln Cys Gln Phe Glu Asp Leu Asn Lys
305                 310                 315                 320

Arg Lys Asp Thr Lys Glu Ile Tyr Thr His Phe Thr Cys Ala Thr Asp
                325                 330                 335

Thr Lys Asn Val Gln Phe Val Phe Asp Ala Val Thr Asp Val Ile Ile
            340                 345                 350

Lys Asn Asn Leu Lys Asp Cys Gly Leu Phe
        355                 360

<210> SEQ ID NO 13
<211> LENGTH: 37
<212> TYPE: DNA
<213> ORGANISM: Artificial Sequence
<220> FEATURE:

<223> OTHER INFORMATION: Primer

<400> SEQUENCE: 13

```
gggggatccg ccaccatgag tgagcttgac cagttac                                37
```

<210> SEQ ID NO 14
<211> LENGTH: 28
<212> TYPE: DNA
<213> ORGANISM: Artificial Sequence
<220> FEATURE:
<223> OTHER INFORMATION: Primer

<400> SEQUENCE: 14

```
gggctcgagg gcgttagttc cagatctt                                          28
```

<210> SEQ ID NO 15
<211> LENGTH: 1051
<212> TYPE: DNA
<213> ORGANISM: Homo sapiens

<400> SEQUENCE: 15

```
gggggatccg ccaccatgag tgagcttgac cagttacggc aggaggccga gcaacttaag       60
aaccagattc gagacgccag gaaagcatgt gcagatgcaa ctctctctca gatcacaaac      120
aacatcgacc cagtgggaag aatccaaatg cgcacgagga ggacactgcg ggggcacctg      180
gccaagatct acgccatgca ctggggcaca gactccaggc ttctcgtcag tgcctcgcag      240
gatggtaaac ttatcatctg gacagctac accaccaaca aggtccacgc catccctctg       300
cgctcctcct gggtcatgac ctgtgcatat gccccttctg gaactatgt ggcctgcggt       360
ggcctggata catttgctc catttacaat ctgaaaactc gtgaggggaa cgtgcgcgtg       420
agtcgtgagc tggcaggaca cacaggttac ctgtcctgct gccgattcct ggatgacaat      480
cagatcgtca ccagctctgg agacaccacg tgtgccctgt gggacatcga gaccggccag      540
cagacgacca cgtttaccgg acacactgga gatgtcatga gcctttctct tgctcctgac      600
accagactgt tcgtctctgg tgcttgtgat gcttcagcca aactctggga tgtgcgagaa      660
ggcatgtgcc ggcagacctt cactggccac gagtctgaca tcaatgccat ttgcttcttt      720
ccaaatggca atgcatttgc cactggctca gacgacgcca cctgcaggct gtttgacctt      780
cgtgctgacc aggagctcat gacttactcc atgacaacaa tcatctgcgg gatcacctct      840
gtctccttct ccaagagcgg gcgcctcctc cttgctgggt acgacgactt caactgcaac      900
gtctgggatg cactcaaagc cgaccgggca ggtgtcttgg ctgggcatga caaccgcgtc      960
agctgcctgg gcgtgactga cgatggcatg gctgtggcga cagggtcctg ggatagcttc     1020
ctcaagatct ggaactaacg ccctcgagcc c                                    1051
```

<210> SEQ ID NO 16
<211> LENGTH: 340
<212> TYPE: PRT
<213> ORGANISM: Homo sapiens

<400> SEQUENCE: 16

```
Met Ser Glu Leu Asp Gln Leu Arg Gln Glu Ala Glu Gln Leu Lys Asn
1               5                   10                  15

Gln Ile Arg Asp Ala Arg Lys Ala Cys Ala Asp Ala Thr Leu Ser Gln
            20                  25                  30

Ile Thr Asn Asn Ile Asp Pro Val Gly Arg Ile Gln Met Arg Thr Arg
        35                  40                  45
```

Arg Thr Leu Arg Gly His Leu Ala Lys Ile Tyr Ala Met His Trp Gly
 50                  55                  60

Thr Asp Ser Arg Leu Leu Val Ser Ala Ser Gln Asp Gly Lys Leu Ile
 65                  70                  75                  80

Ile Trp Asp Ser Tyr Thr Thr Asn Lys Val His Ala Ile Pro Leu Arg
                 85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Ala Gly His Thr Gly
130                 135                 140

Tyr Leu Ser Cys Cys Arg Phe Leu Asp Asp Asn Gln Ile Val Thr Ser
145                 150                 155                 160

Ser Gly Asp Thr Thr Cys Ala Leu Trp Asp Ile Glu Thr Gly Gln Gln
                165                 170                 175

Thr Thr Thr Phe Thr Gly His Thr Gly Asp Val Met Ser Leu Ser Leu
            180                 185                 190

Ala Pro Asp Thr Arg Leu Phe Val Ser Gly Ala Cys Asp Ala Ser Ala
        195                 200                 205

Lys Leu Trp Asp Val Arg Glu Gly Met Cys Arg Gln Thr Phe Thr Gly
210                 215                 220

His Glu Ser Asp Ile Asn Ala Ile Cys Phe Phe Pro Asn Gly Asn Ala
225                 230                 235                 240

Phe Ala Thr Gly Ser Asp Asp Ala Thr Cys Arg Leu Phe Asp Leu Arg
                245                 250                 255

Ala Asp Gln Glu Leu Met Thr Tyr Ser His Asp Asn Ile Ile Cys Gly
            260                 265                 270

Ile Thr Ser Val Ser Phe Ser Lys Ser Gly Arg Leu Leu Leu Ala Gly
        275                 280                 285

Tyr Asp Asp Phe Asn Cys Asn Val Trp Asp Ala Leu Lys Ala Asp Arg
290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 17
<211> LENGTH: 27
<212> TYPE: DNA
<213> ORGANISM: Artificial Sequence
<220> FEATURE:
<223> OTHER INFORMATION: Primer

<400> SEQUENCE: 17
gggggatccg gcgccatgag tgagctg                                      27

<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18

```
gggctcgaga ttagttccag atcttgagga a                                   31
```

<210> SEQ ID NO 19
<211> LENGTH: 1048
<212> TYPE: DNA
<213> ORGANISM: Homo sapiens

<400> SEQUENCE: 19

```
gggggatccg cgccatgag tgagctggag caactgagac aggaggccga gcagctccgg     60
aaccagatcc gggatgcccg aaaagcatgt ggggactcaa cactgaccca gatcacagct   120
gggctggacc cagtggggag aatccagatg aggacccgga ggaccctccg tgggcacctg   180
gcaaagatct atgccatgca ctgggggacc gactcaaggc tgctggtcag cgcctcccag   240
gatgggaagc tcatcatctg gacagctac accaccaaca aggtccacgc catcccgctg    300
cgctcctcct gggtaatgac ctgtgcctac gcgccctcag gaactttgt ggcctgtggg    360
gggttggaca catctgctc catctacagc ctcaagaccc gcgagggcaa cgtcagggtc    420
agccgggagc tgcctggcca cactgggtac ctgtcgtgtt gccgcttcct ggatgacaac   480
caaatcatca ccagctctgg ggataccacc tgtgccctgt gggacattga cacaggccag   540
cagacagtgg gttttgctgg acacagtggg gatgtgatgt ccctgtccct ggcccccgat   600
ggccgcacgt ttgtgtcagg cgcctgtgat gcctctatca agctgtggga cgtgcgggat   660
tccatgtgcc gacagacctt catcggccat gaatccgaca tcaatgcagt ggctttcttc   720
cccaacggct acgccttcac caccggctct gacgacgcca cgtgccgcct cttcgacctg   780
cgggccgatc aggagctcct catgtactcc catgacaaca tcatctgtgg catcacctct   840
gttgccttct cgcgcagcgg acggctgctg ctcgctggct acgacgactt caactgcaac   900
atctgggatg ccatgaaggg cgaccgtgca ggagtcctcg ctggccacga caaccgcgtg   960
agctgcctcg gggtcaccga cgatggcatg gctgtggcca cgggctcctg ggactccttc  1020
ctcaagatct ggaactaatc tcgagccc                                     1048
```

<210> SEQ ID NO 20
<211> LENGTH: 340
<212> TYPE: PRT
<213> ORGANISM: Homo sapiens

<400> SEQUENCE: 20

```
Met Ser Glu Leu Glu Gln Leu Arg Gln Glu Ala Glu Gln Leu Arg Asn
 1               5                  10                  15

Gln Ile Arg Asp Ala Arg Lys Ala Cys Gly Asp Ser Thr Leu Thr Gln
            20                  25                  30

Ile Thr Ala Gly Leu Asp Pro Val Gly Arg Ile Gln Met Arg Thr Arg
        35                  40                  45

Arg Thr Leu Arg Gly His Leu Ala Lys Ile Tyr Ala Met His Trp Gly
    50                  55                  60

Thr Asp Ser Arg Leu Leu Val Ser Ala Ser Gln Asp Gly Lys Leu Ile
65                  70                  75                  80

Ile Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110

Ala Cys Gly Gly Leu Asp Asn Ile Cys Ser Ile Tyr Ser Leu Lys Thr
        115                 120                 125

Arg Glu Gly Asn Val Arg Val Ser Arg Glu Leu Pro Gly His Thr Gly
```

```
              130                 135                 140
Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                165                 170                 175

Thr Val Gly Phe Ala Gly His Ser Gly Asp Val Met Ser Leu Ser Leu
            180                 185                 190

Ala Pro Asp Gly Arg Thr Phe Val Ser Gly Ala Cys Asp Ala Ser Ile
        195                 200                 205

Lys Leu Trp Asp Val Arg Asp Ser Met Cys Arg Gln Thr Phe Ile Gly
    210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
                245                 250                 255

Ala Asp Gln Glu Leu Leu Met Tyr Ser His Asp Asn Ile Ile Cys Gly
            260                 265                 270

Ile Thr Ser Val Ala Phe Ser Arg Ser Gly Arg Leu Leu Leu Ala Gly
        275                 280                 285

Tyr Asp Asp Phe Asn Cys Asn Ile Trp Asp Ala Met Lys Gly Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21
gggggatcca gagtgacccc tcgacctgt                                         29

<210> SEQ ID NO 22
<211> LENGTH: 29
<212> TYPE: DNA
<213> ORGANISM: Artificial Sequence
<220> FEATURE:
<223> OTHER INFORMATION: Primer

<400> SEQUENCE: 22
gggctcgagt ctccagcctc ctcagttcc                                         29

<210> SEQ ID NO 23
<211> LENGTH: 1078
<212> TYPE: DNA
<213> ORGANISM: Homo sapiens

<400> SEQUENCE: 23
gggggatcca gagtgacccc tcgacctgtc agccatgggg gagatggagc aactgcgtca      60
ggaagcggag cagctcaaga agcagattgc agatgccagg aaagcctgtg ctgacgttac     120
tctggcagag ctggtgtctg gcctagaggt ggtgggacga gtccagatgc ggacgcggcg     180
```

```
gacgttaagg ggacacctgg ccaagattta cgccatgcac tgggccactg attctaagct      240
gctggtaagt gcctcgcaag atgggaagct gatcgtgtgg gacagctaca ccaccaacaa      300
ggtgcacgcc atcccactgc gctcctcctg ggtcatgacc tgtgcctatg ccccatcagg      360
gaactttgtg gcatgtgggg ggctggacaa catgtgttcc atctacaacc tcaaatcccg      420
tgagggcaat gtcaaggtca gccgggagct ttctgctcac acaggttatc tctcctgctg      480
ccgcttcctg gatgacaaca atattgtgac cagctcgggg gacaccacgt gtgccttgtg      540
ggacattgag actgggcagc agaagactgt atttgtggga cacacgggtg actgcatgag      600
cctggctgtg tctcctgact caatctctt catttcgggg gcctgtgatg ccagtgccaa      660
gctctgggat gtgcgagagg ggacctgccg tcagactttc actggccacg agtcggacat      720
caacgccatc tgtttcttcc ccaatggaga ggccatctgc acgggctcgg atgacgcttc      780
ctgccgcttg tttgacctgc gggcagacca ggagctgatc tgcttctccc acgagagcat      840
catctgcggc atcacgtccg tggccttctc cctcagtggc cgcctactat tcgctggcta      900
cgacgacttc aactgcaatg tctgggactc catgaagtct gagcgtgtgg gcatcctctc      960
tggccacgat aacagggtga gctgcctggg agtcacagct gacgggatgg ctgtggccac     1020
aggttcctgg gacagcttcc tcaaaatctg gaactgagga ggctggagac tcgagccc      1078

<210> SEQ ID NO 24
<211> LENGTH: 340
<212> TYPE: PRT
<213> ORGANISM: Homo sapiens

<400> SEQUENCE: 24

Met Gly Glu Met Glu Gln Leu Arg Gln Glu Ala Glu Gln Leu Lys Lys
1               5                   10                  15

Gln Ile Ala Asp Ala Arg Lys Ala Cys Ala Asp Val Thr Leu Ala Glu
            20                  25                  30

Leu Val Ser Gly Leu Glu Val Val Gly Arg Val Gln Met Arg Thr Arg
        35                  40                  45

Arg Thr Leu Arg Gly His Leu Ala Lys Ile Tyr Ala Met His Trp Ala
    50                  55                  60

Thr Asp Ser Lys Leu Leu Val Ser Ala Ser Gln Asp Gly Lys Leu Ile
65                  70                  75                  80

Val Trp Asp Ser Tyr Thr Thr Asn Lys Val His Ala Ile Pro Leu Arg
                85                  90                  95

Ser Ser Trp Val Met Thr Cys Ala Tyr Ala Pro Ser Gly Asn Phe Val
            100                 105                 110

Ala Cys Gly Gly Leu Asp Asn Met Cys Ser Ile Tyr Asn Leu Lys Ser
        115                 120                 125

Arg Glu Gly Asn Val Lys Val Ser Arg Glu Leu Ser Ala His Thr Gly
    130                 135                 140

Tyr Leu Ser Cys Cys Arg Phe Leu Asp Asp Asn Ile Val Thr Ser
145                 150                 155                 160

Ser Gly Asp Thr Thr Cys Ala Leu Trp Asp Ile Glu Thr Gly Gln Gln
                165                 170                 175

Lys Thr Val Phe Val Gly His Thr Gly Asp Cys Met Ser Leu Ala Val
            180                 185                 190

Ser Pro Asp Phe Asn Leu Phe Ile Ser Gly Ala Cys Asp Ala Ser Ala
        195                 200                 205

Lys Leu Trp Asp Val Arg Glu Gly Thr Cys Arg Gln Thr Phe Thr Gly
    210                 215                 220
```

```
His Glu Ser Asp Ile Asn Ala Ile Cys Phe Phe Pro Asn Gly Glu Ala
225                 230                 235                 240

Ile Cys Thr Gly Ser Asp Ala Ser Cys Arg Leu Phe Asp Leu Arg
            245                 250                 255

Ala Asp Gln Glu Leu Ile Cys Phe Ser His Glu Ser Ile Ile Cys Gly
            260                 265                 270

Ile Thr Ser Val Ala Phe Ser Leu Ser Gly Arg Leu Leu Phe Ala Gly
        275                 280                 285

Tyr Asp Asp Phe Asn Cys Asn Val Trp Asp Ser Met Lys Ser Glu Arg
        290                 295                 300

Val Gly Ile Leu Ser Gly His Asp Asn Arg Val Ser Cys Leu Gly Val
305                 310                 315                 320

Thr Ala Asp Gly Met Ala Val Ala Thr Gly Ser Trp Asp Ser Phe Leu
                325                 330                 335

Lys Ile Trp Asn
            340

<210> SEQ ID NO 25
<211> LENGTH: 37
<212> TYPE: DNA
<213> ORGANISM: Artificial Sequence
<220> FEATURE:
<223> OTHER INFORMATION: Primer

<400> SEQUENCE: 25
gggggatcca ccgccatgag cgaactggaa cagttga                              37

<210> SEQ ID NO 26
<211> LENGTH: 33
<212> TYPE: DNA
<213> ORGANISM: Artificial Sequence
<220> FEATURE:
<223> OTHER INFORMATION: Primer

<400> SEQUENCE: 26
gggctcgagt gacactgtta attccagatt cta                                  33

<210> SEQ ID NO 27
<211> LENGTH: 1055
<212> TYPE: DNA
<213> ORGANISM: Homo sapiens

<400> SEQUENCE: 27
gggggatcca ccgccatgag cgaactggaa cagttgaggc aagaagcaga acaactgcgg     60
aatcagattc aggatgctcg gaaagcatgt aatgatgcaa cgcttgttca gattacatca    120
aatatggact ctgtgggtcg aatacaaatg cgaacaagac gtacactgag ggccaccta    180 gctaaaatct atgctatgca ttggggatac gattccaggc tgctagtcag tgcttctcaa    240 gatgaaaat taattatttg ggatagctat acaacaaata agatgcatgc tattcctttg    300
aggtcctcct gggtgatgac ctgtgcttat gctccctctg gtaattatgt tgcctgtgga    360
ggcttggaca acatctgctc tatatataac ttaaagacca gagagggaaa tgtgagagta    420
agccgagagt tgccaggtca cacagggtac ttgtcctgct gtcgtttttt agatgacagc    480
caaattgtta caagttcagg agatacaact tgtgctttat gggacatcga aactgcccag    540
cagaccacca cattcactgg gcattctgga gatgtgatga gtctttcttt gagtcctgac    600
atgaggactt tgtttctgg tgcttgtgat gcctcttcca aattatggga tattcgagat    660
```

```
ggaatgtgta gacagtcttt cacgggacat gtctcagata tcaatgctgt cagttttttc    720
ccaaatggat atgccttcgc cactggctct gatgatgcca cttgccggct ctttgacctt    780
cgtgcagatc aagagttatt attgtattct catgacaata tcatctgtgg aatcacttct    840
gtagccttct caaaaagtgg gcgtctcttg ttggctggtt acgatgactt taattgtaat    900
gtatgggaca cgctaaaagg agatcgtgca ggtgtccttg ctggtcatga caaccgtgtg    960
agctgcttag gtgtaactga tgatggcatg gctgtggcaa caggctcttg ggacagtttt   1020
cttagaatct ggaattaaca gtgtcactcg agccc                              1055
```

<210> SEQ ID NO 28
<211> LENGTH: 340
<212> TYPE: PRT
<213> ORGANISM: Homo sapiens

<400> SEQUENCE: 28

```
Met Ser Glu Leu Glu Gln Leu Arg Gln Glu Ala Glu Gln Leu Arg Asn
1               5                   10                  15

Gln Ile Gln Asp Ala Arg Lys Ala Cys Asn Asp Ala Thr Leu Val Gln
                20                  25                  30

Ile Thr Ser Asn Met Asp Ser Val Gly Arg Ile Gln Met Arg Thr Arg
            35                  40                  45

Arg Thr Leu Arg Gly His Leu Ala Lys Ile Tyr Ala Met His Trp Gly
        50                  55                  60

Tyr Asp Ser Arg Leu Leu Val Ser Ala Ser Gln Asp Gly Lys Leu Ile
65                  70                  75                  80

Ile Trp Asp Ser Tyr Thr Thr Asn Lys Met His Ala Ile Pro Leu Arg
                85                  90                  95

Ser Ser Trp Val Met Thr Cys Ala Tyr Ala Pro Ser Gly Asn Tyr Val
            100                 105                 110

Ala Cys Gly Gly Leu Asp Asn Ile Cys Ser Ile Tyr Asn Leu Lys Thr
        115                 120                 125

Arg Glu Gly Asn Val Arg Val Ser Arg Glu Leu Pro Gly His Thr Gly
    130                 135                 140

Tyr Leu Ser Cys Cys Arg Phe Leu Asp Asp Ser Gln Ile Val Thr Ser
145                 150                 155                 160

Ser Gly Asp Thr Thr Cys Ala Leu Trp Asp Ile Glu Thr Ala Gln Gln
                165                 170                 175

Thr Thr Thr Phe Thr Gly His Ser Gly Asp Val Met Ser Leu Ser Leu
            180                 185                 190

Ser Pro Asp Met Arg Thr Phe Val Ser Gly Ala Cys Asp Ala Ser Ser
        195                 200                 205

Lys Leu Trp Asp Ile Arg Asp Gly Met Cys Arg Gln Ser Phe Thr Gly
    210                 215                 220

His Val Ser Asp Ile Asn Ala Val Ser Phe Phe Pro Asn Gly Tyr Ala
225                 230                 235                 240

Phe Ala Thr Gly Ser Asp Asp Ala Thr Cys Arg Leu Phe Asp Leu Arg
                245                 250                 255

Ala Asp Gln Glu Leu Leu Leu Tyr Ser His Asp Asn Ile Ile Cys Gly
            260                 265                 270

Ile Thr Ser Val Ala Phe Ser Lys Ser Gly Arg Leu Leu Leu Ala Gly
        275                 280                 285

Tyr Asp Asp Phe Asn Cys Asn Val Trp Asp Thr Leu Lys Gly Asp Arg
    290                 295                 300
```

```
Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Arg Ile Trp Asn
            340

<210> SEQ ID NO 29
<211> LENGTH: 34
<212> TYPE: DNA
<213> ORGANISM: Artificial Sequence
<220> FEATURE:
<223> OTHER INFORMATION: Primer

<400> SEQUENCE: 29
gggggatcca ccgccatggc aaccgagggg ctgc                              34

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
gggctcgaga agatgattag gcccagactc t                                 31

<210> SEQ ID NO 31
<211> LENGTH: 1093
<212> TYPE: DNA
<213> ORGANISM: Homo sapiens

<400> SEQUENCE: 31
gggggatcca ccgccatggc aaccgagggg ctgcacgaga cgagacgct ggcgtcgctg     60 aagagcgagg ccgagagcct caagggcaag ctggaggagg agcgagccaa gctgcacgat   120
gtggagctgc accaggtggc ggagcgggtg gaggccctgg ggcagtttgt catgaagacc   180
agaaggaccc tcaaaggcca cgggaacaaa gtcctgtgca tggactggtg caaagataag   240
aggaggatcg tgagctcgtc acaggatggg aaggtgatcg tgtgggattc cttcaccaca   300
aacaaggagc acgcggtcac catgcccctgc acgtgggtga tggcatgtgc ttatgcccca   360 tcggatgtg ccattgcttg tggtggtttg gataataagt gttctgtgta ccccttgacg   420
tttgacaaaa atgaaaacat ggctgccaaa aagaagtctg ttgctatgca caccaactac   480
ctgtcggcct gcagcttcac caactctgac atgcagatcc tgacagcgag cggcgatggc   540
acatgtgccc tgtgggacgt ggagagcggg cagctgctgc agagcttcca cggacatggg   600
gctgacgtcc tctgcttgga cctggccccc tcagaaactg gaaacacctt cgtgtctggg   660
ggatgtgaca gaaaagccat ggtgtgggac atgcgctccg gccagtgcgt gcaggccttt   720
gaaacacatg aatctgacat caacagtgtc cggtactacc ccagtggaga tgcctttgct   780
tcagggtcag atgacgctac gtgtcgcctc tatgacctgc gggcagatag ggaggttgcc   840
atctattcca aagaaagcat catatttgga gcatccagcg tggacttctc cctcagtggt   900
cgcctgctgt ttgctggata caatgattac actatcaacg tctgggatgt ctcaaaggg   960 tccccgggtct ccatcctgtt tggacatgaa aaccgcgtta gcactctacg agtttccccc  1020
gatgggactg ctttctgctc tggatcatgg gatcataccc tcagagtctg ggcctaatca  1080
tcttctcgag ccc                                                    1093
```

```
<210> SEQ ID NO 32
<211> LENGTH: 353
<212> TYPE: PRT
<213> ORGANISM: Homo sapiens

<400> SEQUENCE: 32

Met Ala Thr Glu Gly Leu His Glu Asn Glu Thr Leu Ala Ser Leu Lys
1               5                   10                  15

Ser Glu Ala Glu Ser Leu Lys Gly Lys Leu Glu Glu Arg Ala Lys
            20                  25                  30

Leu His Asp Val Glu Leu His Gln Val Ala Glu Arg Val Glu Ala Leu
            35                  40                  45

Gly Gln Phe Val Met Lys Thr Arg Arg Thr Leu Lys Gly His Gly Asn
        50                  55                  60

Lys Val Leu Cys Met Asp Trp Cys Lys Asp Lys Arg Ile Val Ser
65                  70                  75                  80

Ser Ser Gln Asp Gly Lys Val Ile Val Trp Asp Ser Phe Thr Thr Asn
                85                  90                  95

Lys Glu His Ala Val Thr Met Pro Cys Thr Trp Val Met Ala Cys Ala
            100                 105                 110

Tyr Ala Pro Ser Gly Cys Ala Ile Ala Cys Gly Gly Leu Asp Asn Lys
        115                 120                 125

Cys Ser Val Tyr Pro Leu Thr Phe Asp Lys Asn Glu Asn Met Ala Ala
    130                 135                 140

Lys Lys Lys Ser Val Ala Met His Thr Asn Tyr Leu Ser Ala Cys Ser
145                 150                 155                 160

Phe Thr Asn Ser Asp Met Gln Ile Leu Thr Ala Ser Gly Asp Gly Thr
                165                 170                 175

Cys Ala Leu Trp Asp Val Glu Ser Gly Gln Leu Leu Gln Ser Phe His
            180                 185                 190

Gly His Gly Ala Asp Val Leu Cys Leu Asp Leu Ala Pro Ser Glu Thr
        195                 200                 205

Gly Asn Thr Phe Val Ser Gly Gly Cys Asp Lys Lys Ala Met Val Trp
    210                 215                 220

Asp Met Arg Ser Gly Gln Cys Val Gln Ala Phe Glu Thr His Glu Ser
225                 230                 235                 240

Asp Ile Asn Ser Val Arg Tyr Tyr Pro Ser Gly Asp Ala Phe Ala Ser
                245                 250                 255

Gly Ser Asp Asp Ala Thr Cys Arg Leu Tyr Asp Leu Arg Ala Asp Arg
            260                 265                 270

Glu Val Ala Ile Tyr Ser Lys Glu Ser Ile Ile Phe Gly Ala Ser Ser
        275                 280                 285

Val Asp Phe Ser Leu Ser Gly Arg Leu Leu Phe Ala Gly Tyr Asn Asp
    290                 295                 300

Tyr Thr Ile Asn Val Trp Asp Val Leu Lys Gly Ser Arg Val Ser Ile
305                 310                 315                 320

Leu Phe Gly His Glu Asn Arg Val Ser Thr Leu Arg Val Ser Pro Asp
                325                 330                 335

Gly Thr Ala Phe Cys Ser Gly Ser Trp Asp His Thr Leu Arg Val Trp
            340                 345                 350

Ala

<210> SEQ ID NO 33
<211> LENGTH: 68
```

```
<212> TYPE: DNA
<213> ORGANISM: Artificial Sequence
<220> FEATURE:
<223> OTHER INFORMATION: Primer

<400> SEQUENCE: 33
gggggatccg ccaccatgga gcagaaactc atctctgaag aggatctggc cagcaacaac    60
accgccag                                                             68

<210> SEQ ID NO 34
<211> LENGTH: 33
<212> TYPE: DNA
<213> ORGANISM: Artificial Sequence
<220> FEATURE:
<223> OTHER INFORMATION: Primer

<400> SEQUENCE: 34
gggctcgagt taaaggatgg cacagaaaaa ctt                                 33

<210> SEQ ID NO 35
<211> LENGTH: 290
<212> TYPE: DNA
<213> ORGANISM: Homo sapiens

<400> SEQUENCE: 35
gggggatccg ccaccatgga gcagaaactc atctctgaag aggatctggc cagcaacaac    60
accgccaggc cagcaacaac accgccagca tagcacaagc caggaagctg gtagagcagc   120
ttaagatgga agccaatatc gacaggataa aggtgtccaa ggcagctgca gatttgatgg   180
cctactgtga agcacatgcc aaggaagacc ccctcctgac ccctgttccg gcttcagaaa   240
acccgtttag ggagaagaag ttttcttgtg ccatccttta actcgagccc              290

<210> SEQ ID NO 36
<211> LENGTH: 80
<212> TYPE: PRT
<213> ORGANISM: Human adenovirus type 1

<400> SEQUENCE: 36

Met Glu Gln Lys Leu Ile Ser Glu Glu Asp Ala Ser Asn Asn Thr Ala
1               5                   10                  15

Ser Ile Ala Gln Ala Arg Lys Leu Val Glu Gln Leu Lys Met Glu Ala
            20                  25                  30

Asn Ile Asp Arg Ile Lys Val Ser Lys Ala Ala Ala Asp Leu Met Ala
        35                  40                  45

Tyr Cys Glu Ala His Ala Lys Glu Asp Pro Leu Leu Thr Pro Val Pro
    50                  55                  60

Ala Ser Glu Asn Pro Phe Arg Glu Lys Lys Phe Phe Cys Ala Ile Leu
65                  70                  75                  80

<210> SEQ ID NO 37
<211> LENGTH: 19
<212> TYPE: RNA
<213> ORGANISM: Artificial Sequence
<220> FEATURE:
<223> OTHER INFORMATION: sense strand of negative control siRNA

<400> SEQUENCE: 37
uucuccgaac gugucacgu                                                 19

<210> SEQ ID NO 38
<211> LENGTH: 19
```

```
<212> TYPE: RNA
<213> ORGANISM: Artificial Sequence
<220> FEATURE:
<223> OTHER INFORMATION: antisense strand of negative control siRNA

<400> SEQUENCE: 38
acgugacacg uucggagaa                                                       19

<210> SEQ ID NO 39
<211> LENGTH: 19
<212> TYPE: RNA
<213> ORGANISM: Artificial Sequence
<220> FEATURE:
<223> OTHER INFORMATION: sense strand of G beta 1 siRNA

<400> SEQUENCE: 39
gaucauuguu gcacacaaa                                                       19

<210> SEQ ID NO 40
<211> LENGTH: 19
<212> TYPE: RNA
<213> ORGANISM: Artificial Sequence
<220> FEATURE:
<223> OTHER INFORMATION: antisense strand of G beta 1 siRNA

<400> SEQUENCE: 40
uuugugugca acaaugauc                                                       19

<210> SEQ ID NO 41
<211> LENGTH: 19
<212> TYPE: RNA
<213> ORGANISM: Artificial Sequence
<220> FEATURE:
<223> OTHER INFORMATION: sense strand of G beta 2 siRNA

<400> SEQUENCE: 41
gccaugaauc cgacaucaa                                                       19

<210> SEQ ID NO 42
<211> LENGTH: 19
<212> TYPE: RNA
<213> ORGANISM: Artificial Sequence
<220> FEATURE:
<223> OTHER INFORMATION: antisense strand of G beta 2 siRNA

<400> SEQUENCE: 42
uugaugucgg auucauggc                                                       19

<210> SEQ ID NO 43
<211> LENGTH: 19
<212> TYPE: RNA
<213> ORGANISM: Artificial Sequence
<220> FEATURE:
<223> OTHER INFORMATION: sense strand of G beta 4 siRNA

<400> SEQUENCE: 43
ccuuauauuu gcaggugaa                                                       19

<210> SEQ ID NO 44
<211> LENGTH: 19
<212> TYPE: RNA
<213> ORGANISM: Artificial Sequence
<220> FEATURE:
<223> OTHER INFORMATION: antisense strand of G beta 4 siRNA

<400> SEQUENCE: 44
```
uucaccugca aauauaagg                                                    19

<210> SEQ ID NO 45
<211> LENGTH: 62
<212> TYPE: DNA
<213> ORGANISM: Artificial Sequence
<220> FEATURE:
<223> OTHER INFORMATION: Primer

<400> SEQUENCE: 45
gggggatccg ccaccatggc ccatcaccat caccatcacg ccgccagcaa caacaccgcc     60
ag                                                                    62

<210> SEQ ID NO 46
<211> LENGTH: 33
<212> TYPE: DNA
<213> ORGANISM: Artificial Sequence
<220> FEATURE:
<223> OTHER INFORMATION: Primer

<400> SEQUENCE: 46
ttctcgagtt aaaggatggc acagaaaaac ttc                                  33

<210> SEQ ID NO 47
<211> LENGTH: 257
<212> TYPE: DNA
<213> ORGANISM: Homo sapiens

<400> SEQUENCE: 47
gggggatccg ccaccatggc ccatcaccat cacgccgcca gcaacaacac cgccagcata     60
gcacaagcca ggaagctggt agagcagctt aagatggaag ccaatatcga caggataaag    120
gtgtccaagg cagctgcaga tttgatggcc tactgtgaag cacatgccaa ggagacccc     180 ctcctgaccc ctgttccggc ttcagaaaac ccgtttaggg agaagaagtt tttctgtgcc    240
atcctttaac tcgagaa                                                   257

<210> SEQ ID NO 48
<211> LENGTH: 79
<212> TYPE: PRT
<213> ORGANISM: Homo sapiens

<400> SEQUENCE: 48

Met Ala His His His His His His Ala Ala Ser Asn Asn Thr Ala Ser
1               5                   10                  15

Ile Ala Gln Ala Arg Lys Leu Val Glu Gln Leu Lys Met Glu Ala Asn
            20                  25                  30

Ile Asp Arg Ile Lys Val Ser Lys Ala Ala Ala Asp Leu Met Ala Tyr
        35                  40                  45

Cys Glu Ala His Ala Lys Glu Asp Pro Leu Leu Thr Pro Val Pro Ala
    50                  55                  60

Ser Glu Asn Pro Phe Arg Glu Lys Lys Phe Phe Cys Ala Ile Leu
65                  70                  75